United States Patent [19]

Reppert et al.

[11] Patent Number: 5,856,124
[45] Date of Patent: Jan. 5, 1999

[54] DNA ENCODING HIGH-AFFINITY MELATONIN RECEPTORS

[75] Inventors: Steven M. Reppert, Newton, Mass.; Takashi Ebisawa, Tokyo, Japan

[73] Assignee: The General Hospital Corporation, Boston, Mass.

[21] Appl. No.: 466,103

[22] Filed: Jun. 6, 1995

Related U.S. Application Data

[63] Continuation-in-part of Ser. No. 319,887, Oct. 7, 1994, abandoned, which is a continuation-in-part of Ser. No. 261,857, Jun. 17, 1994, abandoned.

[51] Int. Cl.$^6$ ............................ C12N 15/12; C12N 15/63; C12N 5/10
[52] U.S. Cl. .................... 435/69.1; 536/23.5; 435/320.1; 435/325
[58] Field of Search ................................ 536/23.1, 23.5; 435/320.1, 325

[56] References Cited

U.S. PATENT DOCUMENTS 5,508,164   4/1996   Kausch et al. ............................... 435/6

OTHER PUBLICATIONS

Fraser et al., "Melatonin Receptor mRNA Expression in *Xenopus Oocytes*: inhibition of G–Protein–activated Response", Neuroscience Letters, 124:242–245 (1991).

George et al. (1988) Macromolecular Sequencing and Synthesis Selected Methods and Application Ced. by D.H. Schlesinger), Alan R. Liss Inc., New York, pp. 127–149.

Wallace et al. (1987) Methods in Enzymology 152: 432–442.

Masu et al. (1987) Nature 329: 836–838, Oct. 1987.

Watson et al. (1994) The G–Protein Linked Receptor Facts Book, Academic Press, San Diego, pp. 2–6, 8–9, 1994.

Bowie et al. (1990) Science 247:1306–1310, Mar. 1990.

Bagnara, J.T. and Hadley, M.E., "Endocrinology of the Amphibian Pineal", *Am. Zoologist* (1970) 10:201–216.

Bartness, T.J. and Goldman, B.D., "Mammalian pineal melatonin:A clock for all seasons", *Experientia* (1989) 45:939–945.

Bittman, E. L. and Weaver, D. Dr., "The distribution of melatonin binding sites in neuroendocrine tissues of the ewe", *Biology of Reproduction*, (1990) 43:986–993.

Carlson, L.L. et al., "Melatonin Signal Transduction in Hamster Brain:Inhibition of Adenylyl Cyclase by a Petussis Toxin–Sensitive G Protein", *Endocrinology* (1989) 125:2670–2676.

Dubocovich, M.L. and Takahashi, J.S., "Use of 2–[$^{125}$I] iodomelatonin to characterize melatonin binding sites in chicken retina",*Proc. Natl. Sci. USA* (1987) 84:3916–3920.

Ebisawa, T. et al., "Expression cloning of a high–affinity melatonin receptor from Xenopus dermal melanophores", *Proc. Natl. Acad. Sci. USA,* (1994) 91:6133–6137.

Geissler, E.N. et al., "Stem Cell Factor (SCF), a Novel Hematopoietic Growth Factor and Ligand for c–kit Tyrosine Kinase Receptor, Maps on Human Chromosome 12 between 12q14.3 and 12qter", *Somatic Cell and Molecular Genetics,* (1991) 17(2):207–214.

Glaser, T., Housman, D., Lewis, W.H., Gerhard, D. & Jones C. "A Fine–Structure Deletion Map of Human Chromosome 11p: Analysis of J1 Series Hybrids" *Somat.Cell. Mol.Genet,* (1980) 15:477–501, Fig. 23.

Karne, S. et al., "Cloning and Characterization of an Endothelin–3 Specific Receptor (ET$_c$ Receptor) from *Xenopus laevis* Dermal Melanophores", *J. Biol. Chem.* (1993) 268:19126–19133.

Karsch, F.J. et al., "Neuroendocrine Basis of Seasonal Reproduction", *Recent Prog. Horm. Res.* (1984) 40:185–232.

Kozak, M., "An analysis of 5'–noncoding sequences from 699 vertebrate messenger RNAs", *Nucleic Acids Res.* (1987) 15:8125–8148.

Kyte, J. and Doolittle, R.F., "A Simple Method for Displaying the Hydropathic Character of a Protein", *J. Mol. Biol.* (1982) 157:105–132.

Laitinen, J.T. and Saavedra, J.M., "Characterization of Melatonin Receptors in the Rat Suprachiasmatic Nuclei:Modulation of Affinity with Cations and Guanine Nucleotides", *Endocrinology* (1990) 126:2110–2115.

Morgan, P.J. et al., "Guanine Nucleotides Regulate the Affinity of Melatonin Receptors on the Ovine *Pars tuberalis*", *Neuroendocrinology* (1989) 50:359–362.

Munson, P.J. and Rodbard, D., "Ligand: A Versatile Computerized Approach for Characterization of Ligand–Binding Systems", *Anal. Biochem.* (1980) 107:220–239.

Pelletier, J. et al., "Short Communication—Assignment of Two of the Translation Initiation Factor 4E (EIF4EL1 and EIF4EL2) Genes to Human Chromosomes 4 and 20", *Genomics* (1991) 10(4):1079–1082.

(List continued on next page.)

*Primary Examiner*—Lila Feisee
*Assistant Examiner*—Michael Pak
*Attorney, Agent, or Firm*—Fish & Richardson P.C.

[57] ABSTRACT

Disclosed are cDNAs and DNAs encoding high-affinity melatonin 1a and 1b receptors and the recombinant polypeptides expressed from such cDNAs. The recombinant receptor polypeptides, receptor fragments and analogs expressed on the surface of cells are used in methods of screening candidate compounds for their ability to act as agonists or antagonists to the effects of interaction between melatonin and high-affinity melatonin receptor. Agonists are used as therapeutics to reentrain endogenous melatonin rhythms as a means of treating circadian rhythm disorders in humans and control reproductive cycles in seasonally breeding animals. Antagonists are used as therapeutics to control the initiation or timing of puberty in humans. Antibodies specific for a high-affinity melatonin receptor (or receptor fragment or analog) and their use as a therapeutic are also disclosed.

19 Claims, 34 Drawing Sheets

OTHER PUBLICATIONS

Reppert, S.M. et al., "Putative Melatonin Receptors in a Human Biological Clock", *Science* (1988) 242:78–81.

Reppert, S.M. et al., "Cloning and Characterization of a Mammalian Melatonin Receptor That Mediates Reproductive and Circadian Responses", *Neuron* (1994) 13:1177–1185.

Rivkees, S.A. et al., "Guanine nucleotide–binding protein regulation of melatonin receptors in lizard brain", *Proc. Natl. Acad. Sci. USA* (1989) 86:3882–3886.

Vanecek, J., "Melatonin Binding Sites", *J. Neurochem.* (1988) 51:1436–1440.

Weaver, D.R. et al., "Localization of Melatonin Receptors in Mammalian Brain" in *Suprachiasmatic nucleus*: the mind's clock, Klein, D.C. Moore, R.Y., and Reppert, S.M. (1991) eds. New York: Oxford University Press: pp. 289–308.

Weaver, D.R. et al., "Localization and Characterization of Melatonin Receptors in Rodents Brain by in vitro Autoradiography", *The Journal of Neuroscience* (1989) 9(7):2581–2590.

```
     tGCCTATCTCCCTTTGCCAGGGGGCAGAGAAATGATGgagGTGAATAGCACTTGCTTGGA
   1 ---------+---------+---------+---------+---------+---------+ 60
     aCGGATAGAGGGAAACGGTCCCCCGTCTCTTTACTACCtcCACTTATCGTGAACGAACCT
``` b                M   M   E   V   N   S   T   C   L   D -

```
     TTGCAGGACACCTGGTACCATACGAACAGAGCAGGATGCACAGGACAGCGCATCTCAGGG
  61 ---------+---------+---------+---------+---------+---------+ 120
     AACGTCCTGTGGACCATGGTATGCTTGTCTCGTCCTACGTGTCCTGTCGCGTAGAGTCCC
``` b    C   R   T   P   G   T   I   R   T   E   Q   D   A   Q   D   S   A   S   Q   G -

```
     ACTCACCTCTGCCCTGGCGGTGGTTCTTATATTCACCATTGTTGTGGATGTCCTGGGCaa
 121 ---------+---------+---------+---------+---------+---------+ 180
     TGAGTGGAGACGGGACCGCCACCAAGAATATAAGTGGTAACAACACCTACAGGACCCGtt
``` b    L   T   S   A   L   A   V   V   L   I   F   T   I   V   V   D   V   L   G   N -

```
   - tatattggtcatttgtctgtcctgaggaacaagaagctgcagaatgctggaaatctctt
 181 ---------+---------+---------+---------+---------+---------+ 240
     ataaccagtaaaacagacaggactccttgttcttcgacgtcttacgaccttagagaa
``` b    I   L   V   I   L   S   V   L   R   N   K   K   L   Q   N   A   G   N   L   F -

```
     tgttgtcagtttgtctattgccgatCTGGTTGTTGCTGTGTATCCCTATCCGGTCATTCT
 241 ---------+---------+---------+---------+---------+---------+ 300
     acaacagtcaaacagataacggctaGACCAACAACGACACATAGGGATAGGCCAGTAAGA
``` b    V   V   S   L   S   I   A   D   L   V   V   A   V   Y   P   Y   P   V   I   L -

```
     CATAGCTATTTTCCAGAATGGATGGACGCTTGGAAATATCCATTGTCAGATCAGTGGCTT
 301 ---------+---------+---------+---------+---------+---------+ 360
     GTATCGATAAAAGGTCTTACCTACCTGCGAACCTTTATAGGTAACAGTCTAGTCACCGAA
``` b    I   A   I   F   Q   N   G   W   T   L   G   N   I   H   C   Q   I   S   G   F -

FIG. 1a

```
        CCTGATGGGACTCAGCGTTATTGGATCAGTCTTCAACATAACAGCCATAGCTATCAACAG
   361  ---------+---------+---------+---------+---------+---------+ 420
        GGACTACCCTGAGTCGCAATAACCTAGTCAGAAGTTGTATTGTCGGTATCGATAGTTGTC
``` b      L   M   G   L   S   V   I   G   S   V   F   N   I   T   A   I   A   I   N   R   -

```
        GTATTGCTACATCTGCCACAGCCTGAGATATGACAAGCTTTATAATCAAAGAAGCACCTG
   421  ---------+---------+---------+---------+---------+---------+ 480
        CATAACGATGTAGACGGTGTCGGACTCTATACTGTTCGAAATATTAGTTTCTTCGTGGAC
``` b      Y   C   Y   I   C   H   S   L   R   Y   D   K   L   Y   N   Q   R   S   T   W   -

```
        GTGCTACCTTGGCCTGACATGGATACTAACTATAATTGCAATCGTGCCAAACTTTTTTGT
   481  ---------+---------+---------+---------+---------+---------+ 540
        CACGATGGAACCGGACTGTACCTATGATTGATATTAACGTTAGCACGGTTTGAAAAAACA
``` b      C   Y   L   G   L   T   W   I   L   T   I   I   A   I   V   P   N   F   F   V   -

```
        TGGATCACTACAGTATGACCCCAGGATTTTTTCTTGCACATTTGCGCAGACAGTGAGTTC
   541  ---------+---------+---------+---------+---------+---------+ 600
        ACCTAGTGATGTCATACTGGGGTCCTAAAAAAGAACGTGTAAACGCGTCTGTCACTCAAG
``` b      G   S   L   Q   Y   D   P   R   I   F   S   C   T   F   A   Q   T   V   S   S   -

```
        CTCATACACCATAACAGTAGTGGTGGTGCATTTTATAGTCCCTCTTAGTGTTGTGACATT
   601  ---------+---------+---------+---------+---------+---------+ 660
        GAGTATGTGGTATTGTCATCACCACCACGTAAAATATCAGGGAGAATCACAACACTGTAA
``` b      S   Y   T   I   T   V   V   V   H   F   I   V   P   L   S   V   V   T   F   -

```
        CTGTTACTTAAGAATATGGGTTTTAGTGATCCAAGTCAAACACAGAGTTAGACAAGACTT
   661  ---------+---------+---------+---------+---------+---------+ 720
        GACAATGAATTCTTATACCCAAAATCACTAGGTTCAGTTTGTGTCTCAATCTGTTCTGAA
``` b      C   Y   L   R   I   W   V   L   V   I   Q   V   K   H   R   V   R   Q   D   F   -

FIG. 1b

```
            CAAGCAAAAGTTGACACAAACAGACTTGAGAAATTTCTTGACCATGTTTGTGGTCTTTGT
    721     ---------+---------+---------+---------+---------+---------+  780
            GTTCGTTTTCAACTGTGTTTGTCTGAACTCTTTAAAGAACTGGTACAAACACCAGAAACA b         K  Q  K  L  T  Q  T  D  L  R  N  F  L  T  M  F  V  V  F  V  -

ACTTTTTGCAGTTTGCTGGGCCCCCTTAAACTTTATCGGCCTTGCTGTGGCCATTAATCC
    781     ---------+---------+---------+---------+---------+---------+  840
            TGAAAAACGTCAAACGACCCGGGGGAATTTGAAATAGCCGGAACGACACCGGTAATTAGG b         L  F  A  V  C  W  A  P  L  N  F  I  G  L  A  V  A  I  N  P  -

GTTTCATGTGGCACCAAAGATTCCAGAATGGCTGTTTGTTTTAAGCTATTTCATGGCCTA
    841     ---------+---------+---------+---------+---------+---------+  900
            CAAAGTACACCGTGGTTTCTAAGGTCTTACCGACAAACAAAATTCGATAAAGTACCGGAT b         F  H  V  A  P  K  I  P  E  W  L  F  V  L  S  Y  F  M  A  Y  -

TTTTAACAGTTGTCTCAATGCTGTTATATATGGTGTGCTAAATCAAAACTTCCGCAAGGA
    901     ---------+---------+---------+---------+---------+---------+  960
            AAAATTGTCAACAGAGTTACGACAATATATACCACACGATTTAGTTTTGAAGGCGTTCCT b         F  N  S  C  L  N  A  V  I  Y  G  V  L  N  Q  N  F  R  K  E  -

GTACAAAAGAATACTGATGTCCTTATTGACTCCAAGACTGTTGTTTCTTGACACATCTAG
    961     ---------+---------+---------+---------+---------+---------+ 1020
            CATGTTTTCTTATGACTACAGGAATAACTGAGGTTCTGACAACAAAGAACTGTGTAGATC b         Y  K  R  I  L  M  S  L  L  T  P  R  L  L  F  L  D  T  S  R  -

AGGAGGAACTGAGGGATTGAAAAGTAAGCCTTCGCCAGCTGTAACCAACAACAATCAAGC
   1021     ---------+---------+---------+---------+---------+---------+ 1080
            TCCTCCTTGACTCCCTAACTTTTCATTCGGAAGCGGTCGACATTGGTTGTTGTTAGTTCG b         G  G  T  E  G  L  K  S  K  P  S  P  A  V  T  N  N  Q  A  -
```

FIG. 1c

```
              AGATATGCTAGGAGAAGCAAGGTCACTGTGGCTGAGCAGGAGAAATGGTGCGAAAATGGT
     1081    ---------+---------+---------+---------+---------+---------+ 1140
              TCTATACGATCCTCTTCGTTCCAGTGACACCGACTCGTCCTCTTTACCACGCTTTTACCA b              D   M   L   G   E   A   R   S   L   W   L   S   R   R   N   G   A   K   M   V   -

GATCATCATCAGGCCAAGAAAAGCACAAATTGCAATCATCCATCAAATATTCTGGCCTCA
     1141    ---------+---------+---------+---------+---------+---------+ 1200
              CTAGTAGTAGTCCGGTTCTTTTCGTGTTTAACGTTAGTAGGTAGTTTATAAGACCGGAGT b              I   I   I   R   P   R   K   A   Q   I   A   I   I   H   Q   I   F   W   P   Q   -

GAGTTCATGGGCAACATGCCGTCAAGACACAAAGATTACCGGAGAAGAAGATGGCTGCCG
     1201    ---------+---------+---------+---------+---------+---------+ 1260
              CTCAAGTACCCGTTGTACGGCAGTTCTGTGTTTCTAATGGCCTCTTCTTCTACCGACGGC b              S   S   W   A   T   C   R   Q   D   T   K   I   T   G   E   E   D   G   C   R   -

TGAACTGTGCAAGGACGGGATTTCCCAAAGGTGAGACCCAATGCACTATATCCACATTAT  SEQ ID NO: 1
     1261    ---------+---------+---------+---------+---------+---------+ 1320
              ACTTGACACGTTCCTGCCCTAAAGGGTTTCCACTCTGGGTTACGTGATATAGGTGTAATA b              E   L   C   K   D   G   I   S   Q   R   *   SEQ ID NO: 2
```

FIG. 1d

```
      GGGAGCTCGACGCTCTGGGGATCCACCGGCGCCGGCCCTGCCAGCGCGATGGCGGGGCGG
   1  ---------+---------+---------+---------+---------+---------+ 60
      CCCTCGAGCTGCGAGACCCCTAGGTGGCCGCGGCCGGGACGGTCGCGCTACCGCCCCGCC a                                                        M  A  G  R    -

CTGTGGGGCTCGCCGGGCGGGACCCCCAAGGGCAACGGCAGCAGCGCGCTGCTCAACGTC
  61  ---------+---------+---------+---------+---------+---------+ 120
      GACACCCCGAGCGGCCCGCCCTGGGGGTTCCCGTTGCCGTCGTCGCGCGACGAGTTGCAG a      L  W  G  S  P  G  G  T  P  K  G  N  G  S  S  A  L  L  N  V   -

TCGCAGGCGGCGCCCGGCGCCGGGGACGGTGTGCGGCCGCGGCCCTCGTGGCTGGCCGCC
 121  ---------+---------+---------+---------+---------+---------+ 180
      AGCGTCCGCCGCGGGCCGCGGCCCCTGCCACACGCCGGCGCCGGGAGCACCGACCGGCGG a      S  Q  A  A  P  G  A  G  D  G  V  R  P  R  P  S  W  L  A  A   -

ACCCTCGCCTCCATCCTCATCTTCACCATCGTGGTGGACATCGTGGGCAACCTCCTGGTG
 181  ---------+---------+---------+---------+---------+---------+ 240
      TGGGAGCGGAGGTAGGAGTAGAAGTGGTAGCACCACCTGTAGCACCCGTTGGAGGACCAC a      T  L  A  S  I  L  I  F  T  I  V  V  D  I  V  G  N  L  L  V   -

GTCCTGTCCGTGTATCGGAACAAGAAGCTGAGGAACGCAGGGAATGTGTTTGTGGTGAGC
 241  ---------+---------+---------+---------+---------+---------+ 300
      CAGGACAGGCACATAGCCTTGTTCTTCGACTCCTTGCGTCCCTTACACAAACACCACTCG a      V  L  S  V  Y  R  N  K  K  L  R  N  A  G  N  V  F  V  V  S   -

CTGGCAGTTGCAGACCTGCTGGTGGCCGTGTATCCGTACCCCTTGGCGCTGGCGTCTATA
 301  ---------+---------+---------+---------+---------+---------+ 360
      GACCGTCAACGTCTGGACGACCACCGGCACATAGGCATGGGGAACCGCGACCGCAGATAT a      L  A  V  A  D  L  L  V  A  V  Y  P  Y  P  L  A  L  A  S  I   -

GTTAACAATGGGTGGAGCCTGAGCTCCCTGCATTGCCAACTTAGTGGCTTCCTGATGGGC
 361  ---------+---------+---------+---------+---------+---------+ 420
      CAATTGTTACCCACCTCGGACTCGAGGGACGTAACGGTTGAATCACCGAAGGACTACCCG a      V  N  N  G  W  S  L  S  S  L  H  C  Q  L  S  G  F  L  M  G   -
```

FIG. 2a

```
             TTGAGCGTCATCGGGTCCGTTTTCAGCATCACGGGAATTGCCATCAACCGCTATTGCTGC
         421 ---------+---------+---------+---------+---------+---------+ 480
             AACTCGCAGTAGCCCAGGCAAAAGTCGTAGTGCCCTTAACGGTAGTTGGCGATAACGACG a        L  S  V  I  G  S  V  F  S  I  T  G  I  A  I  N  R  Y  C  C   -

ATCTGCCACAGCCTCAGATACGGCAAGCTGTATAGCGGCACGAATTCCCTCTGCTACGTG
         481 ---------+---------+---------+---------+---------+---------+ 540
             TAGACGGTGTCGGAGTCTATGCCGTTCGACATATCGCCGTGCTTAAGGGAGACGATGCAC a        I  C  H  S  L  R  Y  G  K  L  Y  S  G  T  N  S  L  C  Y  V   -

TTCCTGATCTGGACGCTGACGCTCGTGGCGATCGTGCCCAACCTGTGTGTGGGGACCCTG
         541 ---------+---------+---------+---------+---------+---------+ 600
             AAGGACTAGACCTGCGACTGCGAGCACCGCTAGCACGGGTTGGACACACACCCCTGGGAC a        F  L  I  W  T  L  T  L  V  A  I  V  P  N  L  C  V  G  T  L   -

CAGTACGACCCGAGGATCTATTCCTGTACCTTCACGCAGTCCGTCAGCTCAGCCTACACG
         601 ---------+---------+---------+---------+---------+---------+ 660
             GTCATGCTGGGCTCCTAGATAAGGACATGGAAGTGCGTCAGGCAGTCGAGTCGGATGTGC a        Q  Y  D  P  R  I  Y  S  C  T  F  T  Q  S  V  S  S  A  Y  T   -

ATCGCCGTGGTGGTGTTCCATTTCATAGTTCCGATGCTCGTAGTCGTCTTCTGTTACCTG
         661 ---------+---------+---------+---------+---------+---------+ 720
             TAGCGGCACCACCACAAGGTAAAGTATCAAGGCTACGAGCATCAGCAGAAGACAATGGAC a        I  A  V  V  V  F  H  F  I  V  P  M  L  V  V  V  F  C  Y  L   -

AGAATCTGGGCCCTGGTTCTTCAGGTCAGATGGAAGGTGAAACCGGACAACAAACCGAAA
         721 ---------+---------+---------+---------+---------+---------+ 780
             TCTTAGACCCGGGACCAAGAAGTCCAGTCTACCTTCCACTTTGGCCTGTTGTTTGGCTTT a        R  I  W  A  L  V  L  Q  V  R  W  K  V  K  P  D  N  K  P  K   -

CTGAAGCCCCAGGACTTCAGGAATTTTGTCACCATGTTTGTGGTTTTTGTCCTCTTTGCC
         781 ---------+---------+---------+---------+---------+---------+ 840
             GACTTCGGGGTCCTGAAGTCCTTAAAACAGTGGTACAAACACCAAAAACAGGAGAAACGG a        L  K  P  Q  D  F  R  N  F  V  T  M  F  V  V  F  V  L  F  A   -

ATTTGCTGGGCTCCTCTGAACTTCATTGGTCTCGTTGTGGCCTCGGACCCCGCCAGCATG
         841 ---------+---------+---------+---------+---------+---------+ 900
             TAAACGACCCGAGGAGACTTGAAGTAACCAGAGCAACACCGGAGCCTGGGGCGGTCGTAC a        I  C  W  A  P  L  N  F  I  G  L  V  V  A  S  D  P  A  S  M   -
```

FIG. 2b

```
       GCACCCAGGATCCCCGAGTGGCTGTTTGTGGCTAGTTACTATATGGCATATTTCAACAGC
   901 ---------+---------+---------+---------+---------+---------+ 960
       CGTGGGTCCTAGGGGCTCACCGACAAACACCGATCAATGATATACCGTATAAAGTTGTCG a      A  P  R  I  P  E  W  L  F  V  A  S  Y  Y  M  A  Y  F  N  S  -

TGCCTCAATGCGATCATATATGGACTACTGAACCAAAATTTCAGGCAGGAATACAGAAAA
   961 ---------+---------+---------+---------+---------+---------+ 1020
       ACGGAGTTACGCTAGTATATACCTGATGACTTGGTTTTAAAGTCCGTCCTTATGTCTTTT a      C  L  N  A  I  I  Y  G  L  L  N  Q  N  F  R  Q  E  Y  R  K  -

ATTATAGTCTCATTGTGTACCACCAAGATGTTCTTTGTGGATAGCTCCAATCATGTAGCA
  1021 ---------+---------+---------+---------+---------+---------+ 1080
       TAATATCAGAGTAACACATGGTGGTTCTACAAGAAACACCTATCGAGGTTAGTACATCGT a      I  I  V  S  L  C  T  T  K  M  F  F  V  D  S  S  N  H  V  A  -

GATAGAATTAAACGCAAACCCTCTCCATTAATAGCCAACCATAACCTAATAAAGGTGGAC
  1081 ---------+---------+---------+---------+---------+---------+ 1140
       CTATCTTAATTTGCGTTTGGGAGAGGTAATTATCGGTTGGTATTGGATTATTTCCACCTG a      D  R  I  K  R  K  P  S  P  L  I  A  N  H  N  L  I  K  V  D  -

TCCGTTTAA  SEQ ID NO:3
  1141 ---------  1149
       AGGCAAATT a      S  V  *   -   SEQ ID NO:4
```

FIG. 2c

```
      ATGAAGGGCAATGTCAGCGAGCTGCTCAATGCCACTCAGCAGGCTCCAGGCGGCGGGGAG
  1   ------------+----------+----------+----------+----------+----------+  60
      TACTTCCCGTTACAGTCGCTCGACGAGTTACGGTGAGTCGTCCGAGGTCCGCCGCCCCTC a     M   K   G   N   V   S   E   L   L   N   A   T   Q   Q   A   P   G   G   G   E   -

GGAGCGAGACCACGACCGTCCTGGATGGCCTCTACACTGGCCTTCATCCTCATCTTTACC
 61   ------------+----------+----------+----------+----------+----------+ 120
      CCTCCCTCTGGTGCTGGCAGGACCTACCGGAGATGTGACCGGAAGTAGGAGTAGAAATGG a     G   G   R   P   R   P   S   W   M   A   S   T   L   A   F   I   L   I   F   T   -

ATCGTGGTGGACATTCTGGGCAACCTGCTCGTCATCCTGTCTGTGTACCGCAACAAGAAG
121   ------------+----------+----------+----------+----------+----------+ 180
      TAGCACCACCTGTAAGACCCGTTGGACGACCAGTAGGACAGACACATGGCGTTGTTCTTC a     I   V   V   D   I   L   G   N   L   L   V   I   L   S   V   Y   R   N   K   K   -

CTCACGAACTCAGGGAATATATTTGTGGTGAGTTTAGCTGTGGCAGACCTCGTGGTGGCT
181   ------------+----------+----------+----------+----------+----------+ 240
      GAGTCCTTGAGTCCCTTATATAAACACCACTCAAATCGACACCGTCTGGAGCACCACCGA a     L   R   N   S   G   N   I   F   V   V   S   L   A   V   A   D   L   V   V   A   -

GTTTACCCTTATCCCTTGGTGCTGACATCTATCCTTAACAACGGATGGAATCTGGGATAT
241   ------------+----------+----------+----------+----------+----------+ 300
      CAAATGGGAATAGGGAACCACGACTGTAGATAGGAATTGTTGCCTACCTTAGACCCTATA a     V   Y   P   Y   P   L   V   L   T   S   I   L   N   N   G   W   N   L   G   Y   -

CTACACTGTCAAGTCAGCGCATTTCTAATGGGCTTGAGTGTCATCGGCTCGATATTGAAC
301   ------------+----------+----------+----------+----------+----------+ 360
      GATGTGACAGTTCAGTCGCGTAAAGATTACCCGAACTCACAGTAGCCGAGCTATAACTTG a     L   H   C   Q   V   S   A   F   L   M   G   L   S   V   I   G   S   I   L   N   -

ATCACGGGGATCGCTATGAACCGTTACTGCTACATTTGCCACAGCCTCAAGTACGACAAA
361   ------------+----------+----------+----------+----------+----------+ 420
      TAGTGCCCCTAGCGATACTTGGCAATGACGATGTAAACGGTGTCGGAGTTCATGCTGTTT a     I   T   G   I   A   M   N   R   Y   C   Y   I   C   H   S   L   K   Y   D   K   -

ATATACAGTAACAAGAACTCGCTCTGCTACGTGTTCCTCATATGGATGCTGACACTCATC
421   ------------+----------+----------+----------+----------+----------+ 480
      TATATGTCATTGTTCTTGAGCGAGACGATGCACAAGGACTATACCTACGACTGTGAGTAG a     I   Y   S   N   K   N   S   L   C   Y   V   F   L   I   W   M   L   T   L   I   -
```

FIG. 3a

```
          GCCATCATGCCCAACCTGCAAACCGGAACACTCCAGTACGATCCCCGGATCTACTCCTGT
    481   ------------+----------+----------+----------+----------+----------+ 540
          CGGTAGTACGGGTTGGACGTTTGGCCTTGTGAGGTCATGCTAGGGGCCTAGATGAGGACA a         A  I  M  P  N  L  Q  T  G  T  L  Q  Y  D  P  R  I  Y  S  C  -

ACCTTCACCCAGTCTGTCAGCTCAGCGTACACGATAGCAGTGGTGGTTTTCCATTTCATC
    541   ------------+----------+----------+----------+----------+----------+ 600
          TGGAAGTGGGTCAGACAGTCGAGTCGCATGTGCTATCGTCACCACCAAAAGGTAAAGTAG a         T  F  T  Q  S  V  S  S  A  Y  T  I  A  V  V  F  H  F  I  -

GTGCCTATGATTATTGTCATCTTCTGCTACTTAAGGATATGGGTCCTGGTCCTTCAGGTC
    601   ------------+----------+----------+----------+----------+----------+ 660
          CACGGATACTAATAACAGTAGAAGACGATGAATTCCTATACCCAGGACCAGGAAGTCCAG a         V  P  M  I  I  V  I  F  C  Y  L  R  I  W  V  L  V  L  Q  V  -

AGACGGAGGGTGAAACCCGACAACAAGCCCAAACTGAAGCCCCAGGACTTCAGGAACTTT
    661   ------------+----------+----------+----------+----------+----------+ 720
          TCTGCCTCCCACTTTGGGCTGTTGTTCGGGTTTGACTTCGGGGTCCTGAAGTCCTTGAAA a         R  R  R  V  K  P  D  N  K  P  K  L  K  P  Q  D  F  R  N  F  -

GTCACCATGTTCGTAGTTTTTGTACTTTTTGCCATTTGTTGGGCCCCACTCAACCTCATA
    721   ------------+----------+----------+----------+----------+----------+ 780
          CAGTGGTACAAGCATCAAAAACATGAAAAACGGTAAACAACCCGGGGTGAGTTGGAGTAT a         V  T  M  F  V  V  F  V  L  F  A  I  C  W  A  P  L  N  L  I  -

GGTCTTATTGTGGCCTCAGACCCTGCCACCATGGTCCCCAGGATCCCAGAGTGGCTGTTC
    781   ------------+----------+----------+----------+----------+----------+ 840
          CCAGAATAACACCGGAGTCTGGGACGGTGGTACCAGGGGTCCTAGGGTCTCACCGACAAG a         G  L  I  V  A  S  D  P  A  T  M  V  P  R  I  P  E  W  L  F  -

GTGGCTAGTTACTACCTGGCGTACTTCAACAGCTGCCTCAACGCAATTATATACGGACTA
    841   ------------+----------+----------+----------+----------+----------+ 900
          CACCGATCAATGATGGACCGCATGAAGTTGTCGACGGAGTTGCGTTAATATATGCCTGAT a         V  A  S  Y  Y  L  A  Y  F  N  S  C  L  N  A  I  I  Y  G  L  -

CTGAATCAGAATTTCAGAAAGGAATACAAAAAGATTATTGTCTCGTTGTGCACAGCCAAG
    901   ------------+----------+----------+----------+----------+----------+ 960
          GACTTAGTCTTAAAGTCTTTCCTTATGTTTTTCTAATAACAGAGCAACACGTGTCGGTTC a         L  N  Q  N  F  R  K  E  Y  K  K  I  I  V  S  L  C  T  A  K  -
```

FIG. 3b

```
     ATGTTCTTTGTGGAGAGTTCAAATGAAGAAGCAGATAAGATTAAATGTAAGCCCTCTCCA
961  ----------+---------+---------+---------+---------+---------+ 1020
     TACAAGAAACACCTCTCAAGTTTACTTCTTCGTCTATTCTAATTTACATTCGGGAGAGGT a     M  F  F  V  E  S  S  N  E  E  A  D  K  I  K  C  K  P  S  P  -

CTAATACCCAATAATAACTTCCTCCCGGTGGACTCTGTTTAA
1021 ----------+---------+---------+---------+--    (SEQ ID NO.13)
     GATTATGGGTTATTATTGAAGGAGGGCCACCTGAGACAAATT a     L  I  P  N  N  F  L  P  V  D  S  V  *         (SEQ ID NO:14)
```

FIG. 3c

```
          ggaaacatctttgtggtgagcttagcggtggcagacctggtggtggccatttatccgtac
     1    ----------+---------+---------+---------+---------+---------+   60
          cctttgtagaaacaccactcgaatcgccaccgtctggaccaccaccggtaaataggcatg a       G  N  I  F  V  V  S  L  A  V  A  D  L  V  V  A  I  Y  P  Y   - ccgttggtgctgatgtcgatatttaacaacgggtggaacctgggctatctgcactgccaa
    61    ----------+---------+---------+---------+---------+---------+  120
          ggcaaccacgactacagctataaattgttgcccaccttggacccgatagacgtgacggtt a       P  L  V  L  M  S  I  F  N  N  G  W  N  L  G  Y  L  H  C  Q   - gtcagtgggttcctgatgggcctgagcgtcatcggctccatattcaacatcaccggcatc
   121    ----------+---------+---------+---------+---------+---------+  180
          cagtcacccaaggactacccggactcgcagtagccgaggtataagttgtagtggccgtag a       V  S  G  F  L  M  G  L  S  V  I  G  S  I  F  N  I  T  G  I   -
                                                                          -
                                                                          - gccatcaaccgctacTGTTACATCTGCCACAGTCTCAAGTGCGACAAACTGTACAGCAGC
   181    ----------+---------+---------+---------+---------+---------+  240
          cggtagttggcgatgACAATGTAGACGGTGTCAGAGTTCACGCTGTTTGACATGTCGTCG a       A  I  N  R  Y  C  Y  I  C  H  S  L  K  C  D  K  L  Y  S  S   -

AAGAACTCCCTCTGCTACGTGCTCCTCATATGGCTCCTGACGGCGGCCGTCCTGCCCAAC
   241    ----------+---------+---------+---------+---------+---------+  300
          TTCTTGAGGGAGACGATGCACGAGGAGTATACCGAGGACTGCCGCCGGCAGGACGGGTTG a       K  N  S  L  C  Y  V  L  L  I  W  L  L  T  A  A  V  L  P  N   -

CTCCGTCGTGGGACTCTCCAGTACGAGCCGAGGATCTACTCGTGCACCTTCGCCCAGTCC
   301    ----------+---------+---------+---------+---------+---------+  360
          GAGGCAGCACCCTGAGAGGTCATGCTCGGCTCCTAGATGAGCACGTGGAAGCGGGTCAGG a       L  R  R  G  T  L  Q  Y  E  P  R  I  Y  S  C  T  F  A  Q  S   -

GTCAGCTCCGCCTACACCATCGCCGTGGTGGTTTTCCACTTCCTCGTCCCCATGATCATA
   361    ----------+---------+---------+---------+---------+---------+  420
          CAGTCGAGGCGGATGTGGTAGCGGCACCACCAAAAGGTGAAGGAGCAGGGGTACTAGTAT a       V  S  S  A  Y  T  I  A  V  V  V  F  H  F  L  V  P  M  I  I   -

GTCATCTTCTGTTACCTGAGAATATGGATCCTGGTTCTCCAGGTCAGACAGAGGGTGAAA
   421    ----------+---------+---------+---------+---------+---------+  480
          CAGTAGAAGACAATGGACTCTTATACCTAGGACCAAGAGGTCCAGTCTGTCTCCCACTTT a       V  I  F  C  Y  L  R  I  W  I  L  V  L  Q  V  R  Q  R  V  K   -
```

FIG. 4a

```
     CCTGACCGCAAACCCAAACTGAAACCACACGACTTCAGGAATTTTTGTCACCATGTTTGTG
481  ---------+---------+---------+---------+---------+---------+ 540
     GGACTGGCGTTTGGGTTTGACTTTGGTGTGCTGAAGTCCTTAAAACAGTGGTACAAACAC a    P  D  R  K  P  K  L  K  P  H  D  F  R  N  F  V  T  M  F  V   -

GTTTTTGTCCTTTTTGCCATTTGCTGGGCTCCTCTGAACTTCATTGGCCTGGCCGTGGCC
541  ---------+---------+---------+---------+---------+---------+ 600
     CAAAAACAGGAAAAACGGTAAACGACCCGAGGAGACTTGAAGTAACCGGACCGGCACCGG a    V  F  V  L  F  A  I  C  W  A  P  L  N  F  I  G  L  A  V  A   -

TCTGACCCCGCCAGCATGGTGCCTAGGATCCCAGAGTGGCTGTTTGTGGCCAGTTACTAC
601  ---------+---------+---------+---------+---------+---------+ 660
     AGACTGGGGCGGTCGTACCACGGATCCTAGGGTCTCACCGACAAACACCGGTCAATGATG a    S  D  P  A  S  M  V  P  R  I  P  E  W  L  F  V  A  S  Y  Y   -

ATGGCGTATTTCAACAGCTGCCTCAATGCCATTATATCGGGCTACTGGAACCAAAATTTC
661  ---------+---------+---------+---------+---------+---------+ 720
     TACCGCATAAAGTTGTCGACGGAGTTACGGTAATATAGCCCGATGACCTTGGTTTTAAAG a    M  A  Y  F  N  S  C  L  N  A  I  I  S  G  Y  W  N  Q  N  F   -

AGGAAGGAATACAGGAGAATTATAGTCTCGCTCGTGACAGCCAGGGTGTTCTTTGTGGAC
721  ---------+---------+---------+---------+---------+---------+ 780
     TCCTTCCTTATGTCCTCTTAATATCAGAGCGAGCACTGTCGGTCCCACAAGAAACACCTG a    R  K  E  Y  R  R  I  I  V  S  L  V  T  A  R  V  F  F  V  D   -

AGCTCTAACGACGTGGCCGATAGGGTTAAATGGAAACCGTCTCCACTGATGACCAACAAT
781  ---------+---------+---------+---------+---------+---------+ 840
     TCGAGATTGCTGCACCGGCTATCCCAATTTACCTTTGGCAGAGGTGACTACTGGTTGTTA a    S  S  N  D  V  A  D  R  V  K  W  K  P  S  P  L  M  T  N  N   -

AATGTAGTAAAGGTGGACTCCGTTTAA   SEQ ID NO:5
841  ---------+---------+------- 867
     TTACATCATTTCCACCTGAGGCAAATT a    N  V  V  K  V  D  S  V  *   -  SEQ ID NO:6
```

FIG. 4b

```
     ATGGCCCTGCGGCCGGGACGCGAACAGGGACCATGCAGGGCAACGGCAGCGCGCTGCCCA
  1  ------------------------------------------------------------  60
     TACCGGGACGCCGGCCCTGCGCTTGTCCCTGGTACGTCCCGTTGCCGTCGCGCGACGGGT

M  Q  G  N  G  S  A  L  P  N -

ACGCCTCCCAGCCCGTGCTCCGCGGGGACGGCGCGCGGCCCTCGTGGCTGGCGTCCGCCC
 61  ------------------------------------------------------------ 120
     TGCGGAGGGTCGGGCACGAGGCGCCCCTGCCGCGCGCCGGGAGCACCGACCGCAGGCGGG

A  S  Q  P  V  L  R  G  D  G  A  R  P  S  W  L  A  S  A  L -

TAGCCTGCGTCCTCATCTTCACCATCGTGGTGGACATCCTGGGCAACCTCCTGGTCATCC
121  ------------------------------------------------------------ 180
     ATCGGACGCAGGAGTAGAAGTGGTAGCACCACCTGTAGGACCCGTTGGAGGACCAGTAGG

A  C  V  L  I  F  T  I  V  V  D  I  L  G  N  L  L  V  I  L -

TGTCGGTGTATCGGAACAAGAAGCTCAGGAACGCAggaaacatctttgtggtgagcttag
181  ------------------------------------------------------------ 240
     ACAGCCACATAGCCTTGTTCTTCGAGTCCTTGCGTcctttgtagaaacaccactcgaatc

S  V  Y  R  N  K  K  L  R  N  A  G  N  I  F  V  V  S  L  A - cggtggcagacctggtggtggccatttatccgtacccgttggtgctgatgtcgatattta
241  ------------------------------------------------------------ 300
     gccaccgtctggaccaccaccggtaaataggcatgggcaaccacgactacagctataaat

V  A  D  L  V  V  A  I  Y  P  Y  P  L  V  L  M  S  I  F  N - acaacgggtggaacctgggctatctgcactgccaagtcagtgggttcctgatgggcctga
301  ------------------------------------------------------------ 360
     tgttgcccaccttggacccgatagacgtgacggttcagtcacccaaggactacccggact

```
      gcgtcatcggctccatattcaacatcaccggcatcgccatcaaccgctacTGCTACATCT
361   ------------+----------+----------+----------+----------+----------+ 420
      cgcagtagccgaggtataagttgtagtggccgtagcggtagttggcgatgACGATGTAGA
``` c     V  I  G  S  I  F  N  I  T  G  I  A  I  N  R  Y  C  Y  I  C -

```
      GCCACAGTCTCAAGTACGACAAACTGTACAGCAGCAAGAACTCCCTCTGCTACGTGCTCC
421   ------------+----------+----------+----------+----------+----------+ 480
      CGGTGTCAGAGTTCATGCTGTTTGACATGTCGTCGTTCTTGAGGGAGACGATGCACGAGG
``` c     H  S  L  K  Y  D  K  L  Y  S  S  K  N  S  L  C  Y  V  L  L -

```
      TCATATGGCTCCTGACGCTGGCGGCCGTCCTGCCCAACCTCCGTGCAGGGACTCTCCAGT
481   ------------+----------+----------+----------+----------+----------+ 540
      AGTATACCGAGGACTGCGACCGCCGGCAGGACGGGTTGGAGGCACGTCCCTGAGAGGTCA
``` c     I  W  L  L  T  L  A  A  V  L  P  N  L  R  A  G  T  L  Q  Y -

```
      ACGACCCGAGGATCTACTCGTGCACCTTCGCCCAGTCCGTCAGCTCCGCCTACACCATCG
541   ------------+----------+----------+----------+----------+----------+ 600
      TGCTGGGCTCCTAGATGAGCACGTGGAAGCGGGTCAGGCAGTCGAGGCGGATGTGGTAGC
``` c     D  P  R  I  Y  S  C  T  F  A  Q  S  V  S  S  A  Y  T  I  A -

```
      CCGTGGTGGTTTTCCACTTCCTCGTCCCCATGATCATAGTCATCTTCTGTTACCTGAGAA
601   ------------+----------+----------+----------+----------+----------+ 660
      GGCACCACCAAAAGGTGAAGGAGCAGGGGTACTAGTATCAGTAGAAGACAATGGACTCTT
``` c     V  V  V  F  H  F  L  V  P  M  I  I  V  I  F  C  Y  L  R  I -

```
      TATGGATCCTGGTTCTCCAGGTCAGACAGAGGGTGAAACCTGACCGCAAACCCAAACTGA
661   ------------+----------+----------+----------+----------+----------+ 720
      ATACCTAGGACCAAGAGGTCCAGTCTGTCTCCCACTTTGGACTGGCGTTTGGGTTTGACT
``` c     W  I  L  V  L  Q  V  R  Q  R  V  K  P  D  R  K  P  K  L  K -

FIG. 5b

```
     AACCACAGGACTTCAGGAATTTTGTCACCATGTTTGTGGTTTTTGTCCTCTTTGCCATTT
721  ------------------------------------------------------------ 780
     TTGGTGTCCTGAAGTCCTTAAAACAGTGGTACAAACACCAAAAACAGGAGAAACGGTAAA
``` c       P  Q  D  F  R  N  F  V  T  M  F  V  V  F  V  L  F  A  I  C  -

```
     GCTGGGCTCCTCTGAACTTCATTGGCCTGGCCGTGGCCTCTGACCCCGCCAGCATGGTGC
781  ------------------------------------------------------------ 840
     CGACCCGAGGAGACTTGAAGTAACCGGACCGGCACCGGAGACTGGGGCGGTCGTACCACG
``` c       W  A  P  L  N  F  I  G  L  A  V  A  S  D  P  A  S  M  V  P  -

```
     CTAGGATCCCAGAGTGGCTGTTTGTGGCCAGTTACTACATGGCGTATTTCAACAGCTGCC
841  ------------------------------------------------------------ 900
     GATCCTAGGGTCTCACCGACAAACACCGGTCAATGATGTACCGCATAAAGTTGTCGACGG
``` c       R  I  P  E  W  L  F  V  A  S  Y  Y  M  A  Y  F  N  S  C  L  -

```
     TCAATGCCATTATATACGGGCTACTGAACCAAAATTTCAGGAAGGAATACAGGAGAATTA
901  ------------------------------------------------------------ 960
     AGTTACGGTAATATATGCCCGATGACTTGGTTTTAAAGTCCTTCCTTATGTCCTCTTAAT
``` c       N  A  I  I  Y  G  L  L  N  Q  N  F  R  K  E  Y  R  R  I  I  -

```
     TAGTCTCGCTCTGTACAGCCAGGGTGTTCTTTGTGGACAGCTCTAACGACGTGGCCGATA
961  ------------------------------------------------------------ 1020
     ATCAGAGCGAGACATGTCGGTCCCACAAGAAACACCTGTCGAGATTGCTGCACCGGCTAT
``` c       V  S  L  C  T  A  R  V  F  F  V  D  S  S  N  D  V  A  D  R  -

```
      GGGTTAAATGGAAACCGTCTCCACTGATGACCAACAATAATGTAGTAAAGGTGGACTCCG
1021  ------------------------------------------------------------ 1080
      CCCAATTTACCTTTGGCAGAGGTGACTACTGGTTGTTATTACATCATTTCCACCTGAGGC
``` c       V  K  W  K  P  S  P  L  M  T  N  N  N  V  V  K  V  D  S  V  -
        (SEQ ID NO:12)

```
      TTTAA
1081  ----- 1085 (SEQ ID NO:11)
      AAATT
``` c       *  -

FIG. 5c

```
     GGAGAGTCTGCGATGTCAGAGAACGGCTCCTTCGCCAACTGCTGCGAGGCGGGCGGGTGG
  1  ------------+---------+---------+---------+---------+---------+  60
     CCTCTCAGACGCTACAGTCTCTTGCCGAGGAAGCGGTTGACGACGCTCCGCCCGCCCACC a              M   S   E   N   G   S   F   A   N   C   C   E   A   G   G   W      -

GCAGTGCGCCCGGGCTGGTCGGGGGCTGGCAGCGCGCGGCCCTCCAGGACCCCTCGACCT
 61  ------------+---------+---------+---------+---------+---------+  120
     CGTCACGCGGGCCCGACCAGCCCCCGACCGTCGCGCGCCGGGAGGTCCTGGGGAGCTGGA a    A   V   R   P   G   W   S   G   A   G   S   A   R   P   S   R   T   P   R   P      -

CCCTGGGTGGCTCCAGCGCTGTCCGCGGTGCTCATCGTCACCACCGCCGTGGACGTCGTG
121  ------------+---------+---------+---------+---------+---------+  180
     GGGACCCACCGAGGTCGCGACAGGCGCCACGAGTAGCAGTGGTGGCGGCACCTGCAGCAC a    P   W   V   A   P   A   L   S   A   V   L   I   V   T   T   A   V   D   V   V      -

GGCAACCTCCTGGTGATCCTCTCCGTGCTCAGGAACCGCAAGCTCCGGAACGCAGGTAAT
181  ------------+---------+---------+---------+---------+---------+  240
     CCGTTGGAGGACCACTAGGAGAGGCACGAGTCCTTGGCGTTCGAGGCCTTGCGTCCATTA a    G   N   L   L   V   I   L   S   V   L   R   N   R   K   L   R   N   A   G   N      -

TTGTTCTTGGTGAGTCTGGCATTGGCTGACCTGGTGGTGGCCTTCTACCCCTACCCGCTA
241  ------------+---------+---------+---------+---------+---------+  300
     AACAAGAACCACTCAGACCGTAACCGACTGGACCACCACCGGAAGATGGGGATGGGCGAT a    L   F   L   V   S   L   A   L   A   D   L   V   V   A   F   Y   P   Y   P   L      -

ATCCTCGTGGCCATCTTCTATGACGGCTGGGCCCTGGGGGAGGAGCACTGCAAGGCCAGC
301  ------------+---------+---------+---------+---------+---------+  360
     TAGGAGCACCGGTAGAAGATACTGCCGACCCGGGACCCCCTCCTCGTGACGTTCCGGTCG a    I   L   V   A   I   F   Y   D   G   W   A   L   G   E   E   H   C   K   A   S      -

GCCTTTGTGATGGGCCTGAGCGTCATCGGCTCTGTCTTCAATATCACTGCCATCGCCATT
361  ------------+---------+---------+---------+---------+---------+  420
     CGGAAACACTACCCGGACTCGCAGTAGCCGAGACAGAAGTTATAGTGACGGTAGCGGTAA a    A   F   V   M   G   L   S   V   I   G   S   V   F   N   I   T   A   I   A   I      -

AACCGCTACTGCTACATCTGCCACAGCATGGCCTACCACCGAATCTACCGGCGCTGGCAC
421  ------------+---------+---------+---------+---------+---------+  480
     TTGGCGATGACGATGTAGACGGTGTCGTACCGGATGGTGGCTTAGATGGCCGCGACCGTG a    N   R   Y   C   Y   I   C   H   S   M   A   Y   H   R   I   Y   R   R   W   H      -
```

FIG. 6a

```
        ACCCCTCTGCACATCTGCCTCATCTGGCTCCTCACCGTGGTGGCCTTGCTGCCCAACTTC
481     ------------+---------+---------+---------+---------+---------+ 540
        TGGGGAGACGTGTAGACGGAGTAGACCGAGGAGTGGCACCACCGGAACGACGGGTTGAAG a       T  P  L  H  I  C  L  I  W  L  L  T  V  V  A  L  L  P  N  F   -

TTTGTGGGGTCCCTGGAGTACGACCCACGCATCTATTCCTGCACCTTCATCCAGACCGCC
541     ------------+---------+---------+---------+---------+---------+ 600
        AAACACCCCAGGGACCTCATGCTGGGTGCGTAGATAAGGACGTGGAAGTAGGTCTGGCGG a       F  V  G  S  L  E  Y  D  P  R  I  Y  S  C  T  F  I  Q  T  A   -

AGCACCCAGTACACGGCGGCAGTGGTGGTCATCCACTTCCTCCTCCCTATCGCTGTCGTG
601     ------------+---------+---------+---------+---------+---------+ 660
        TCGTGGGTCATGTGCCGCCGTCACCACCAGTAGGTGAAGGAGGAGGGATAGCGACAGCAC a       S  T  Q  Y  T  A  A  V  V  V  I  H  F  L  L  P  I  A  V  V   -

TCCTTCTGCTACCTGCGCATCTGGGTGCTGGTGCTTCAGGCCCGCAGGAAAGCCAAGCCA
661     ------------+---------+---------+---------+---------+---------+ 720
        AGGAAGACGATGGACGCGTAGACCCACGACCACGAAGTCCGGGCGTCCTTTCGGTTCGGT a       S  F  C  Y  L  R  I  W  V  L  V  L  Q  A  R  R  K  A  K  P   -

GAGAGCAGGCTGTGCCTGAAGCCCAGCGACTTGCGGAGCTTTCTAACCATGTTTGTGGTG
721     ------------+---------+---------+---------+---------+---------+ 780
        CTCTCGTCCGACACGGACTTCGGGTCGCTGAACGCCTCGAAAGATTGGTACAAACACCAC a       E  S  R  L  C  L  K  P  S  D  L  R  S  F  L  T  M  F  V  V   -

TTTGTGATCTTTGCCATCTGCTGGGCTCCACTTAACTGCATCGGCCTCGCTGTGGCCATC
781     ------------+---------+---------+---------+---------+---------+ 840
        AAACACTAGAAACGGTAGACGACCCGAGGTGAATTGACGTAGCCGGAGCGACACCGGTAG a       F  V  I  F  A  I  C  W  A  P  L  N  C  I  G  L  A  V  A  I   -

AACCCCCAAGAAATGGCTCCCCAGATCCCTGAGGGGCTATTTGTCACTAGCTACTTACTG
841     ------------+---------+---------+---------+---------+---------+ 900
        TTGGGGGTTCTTTACCGAGGGGTCTAGGGACTCCCCGATAAACAGTGATCGATGAATGAC a       N  P  Q  E  M  A  P  Q  I  P  E  G  L  F  V  T  S  Y  L  L   -
```

FIG. 6b

```
      GCTTATTTCAACAGCTGCCTGAATGCCATTGTCTATgggCTCTTGAACCAAAACTTCCGC
  901 ---------+---------+---------+---------+---------+---------+ 960
      CGAATAAAGTTGTCGACGGACTTACGGTAACAGATAcccGAGAACTTGGTTTTGAAGGCG a     A  Y  F  N  S  C  L  N  A  I  V  Y  G  L  L  N  Q  N  F  R   -

AGGGAATACAAGAGGATCCTCTTGGCCCTTTGGAACCCACGGCACTGCATTCAAGATGCT
  961 ---------+---------+---------+---------+---------+---------+ 1020
      TCCCTTATGTTCTCCTAGGAGAACCGGGAAACCTTGGGTGCCGTGACGTAAGTTCTACGA a     R  E  Y  K  R  I  L  L  A  L  W  N  P  R  H  C  I  Q  D  A   -

TCCAAGGGCAGCCACGCGGAGGGGCTGCAGAGCCCAGCTCCACCCATCATTGGTGTGCAG
 1021 ---------+---------+---------+---------+---------+---------+ 1080
      AGGTTCCCGTCGGTGCGCCTCCCCGACGTCTCGGGTCGAGGTGGGTAGTAACCACACGTC a     S  K  G  S  H  A  E  G  L  Q  S  P  A  P  P  I  I  G  V  Q   -

CACCAGGCAGATGCTCTCTAGCCTG    (SEQ ID NO:15)
 1081 ---------+---------+----- 1105
      GTGGTCCGTCTACGAGAGATCGGAC a     H  Q  A  D  A  L  *         (SEQ ID NO:16)
```

FIG. 6c

```
xmr                 MMEVNSTCLDCRTPGTIRTEQDAQDSASQG.......LT
ov         MAGRLWGSPGGTPKGNGSSALLNVSQAAPGAGDGVRPRPSWLA
```

```
             I                              II
xmr  SALAVVLIFTIVVDVLGNILVILSV LRNKKLQNAGN LFVVSLSIADLVVAVYPYPVILI
ov   ATLASILIFTIVVDIVGNLLVVLSV YRNKKLRNAGN VFVVSLAVADLLVAVYPYPLALA
hum                                     GN IFVVSLAVADLVVAIYPYPLVLM
                           III
xmr  AI FQNGWTLGNIHCQI SGFLMGLSVIGSVFNITAI AINRYCYICHSLRYDKLYNQRSTW
ov   SI VNNGWSLSSLHCQL SGFLMGLSVIGSVFSITGI AINRYCCICHSLRYGKLYSGTNSL
hum  SI FNNGWNLGYLHCQV SGFLMGLSVIGSIFNITGI AINRYCYICHSLKCDKLYSSKNSL
            IV                                        V
xmr  C YLGLTWILTIIAIVPNFFVG SLQYDPRIFSCTFAQTVSSSYT ITVVVVHFIVPLSVVT
ov   C YVFLIWTLTLVAIVPNLCVG TLQYDPRIYSCTFTQSVSSAYT IAVVVFHFIVPMLVVV
hum  C YVLLIWLLTA.AVLPNLRRG TLQYEPRIYSCTFAQSVSSAYT IAVVVFHFLVPMIIVI
                                                  VI
xmr  FCYLRIWVLVI QVKHRVRQDFKQKLTQTDLRNFL TMFVVFVLFAVCWAPLNFIGLAVAI
ov   FCYLRIWALVL QVRWKVKPDNKPKLKPQDFRNFV TMFVVFVLFAICWAPLNFIGLVVAS
hum  FCYLRIWILVL QVRQRVKPDRKPKLKPHDFRNFV TMFVVFVLFAICWAPLNFIGLAVAS
                   VII
xmr  NPFHVAPKIPE WLFVLSYFMAYFNSCLNAVIYG VLNQNFRKEYKRILMSLLTPRLLFLD
ov   DPASMAPRIPE WLFVASYYMAYFNSCLNAIIYG LLNQNFRQEYRKIIVSLCTTKMFFVD
hum  DPASMVPRIPE WLFVASYYMAYFNSCLNAIISG YWNQNFRKEYRRIIVSLVTARVFFVD
```

```
xmr  TSRGGTEGLKSKPSPAVTNNNQADMLGEARSLWLSRRNGAKMVIIIRPRKAQIAIIHQIF
ov   SSNHVADRIKRKPSPLIANHNLIKVDSV*     SEQ ID NO:4
hum  SSNDVARDVKWKPSPLMTNNNVVKVDSV*     SEQ ID NO:6 xmr  WPQSSWATCRQDTKITGEEDGCRELCKDGISQR    SEQ ID NO:2
```

FIG. 7

```
                         I
Sheep     MAGRLWGSPGGTPKGNGSSALLNVSQAAPGAGDGVRPRPSWLAATLASILIFTIVVDIVGNLLVVLSVYPNKKLRNAGN    79
Human                   MQGNGSALPNASQPVLRGDGA...RPSWLASALACVLIFTIVVDILGNLLVILSVYRNKKLRNAGN    63
Xenopus         MMEVNSICDCRTPGTIRTEQDAQDSASQG.....LTSALAVLIFTIVVDVLGNILVILSVLRNKKLQNAGN    68
Consensus       ---------------------------------L---L---LIFTIVVD--GN-LV-LSV-RNKKL-NAGN II                                III
Sheep     VFVVSLAVADLLVAVYPYPLALASIVNNGWSLSSLHCQLSGFLMGLSVIGSVFSITGIAINRYCCICHSLRYGKLYSGT   158
Human     :FVVSLAVADLLVAIYPYPLVLMSIFNNGWNLGYLHCQVSGFLMGLSVIGSIFNITGIAINRYCYICHSLKYDKLYSSK   142
Xenopus   LFVVSLSIADLVVAVYPYPVILAIFQNGWTLGNIHCQISGFLMGLSVIGSVFNITAIAINRYCYICHSLRYDKLYNQR    147
Consensus -FVVSL--ADL-VA-YPYP-L--I---NGW-L---HCQ-SGFLMGLSVIGS-F--IT-IAINRYC--ICHSL-Y-KLY---

IV                                      V
Sheep     NSLCVVFLIWTLTLVAIVPNLCVGTLQYDPRIYSCTFTQSVSSAYTIAVVVFHFIVPMLVVVFCYLRIWALVLQVRWKV   237
Human     NSLCVVLLIWLILTLAAVLPNLRAGTLQYDPRIYSCTFAQSVSSAYTIAVVVFHFLVPMIVIFCYLRIWILVLQVRQRV   221
Xenopus   STWCYLGLTWILTIIAIVPNFFVGSLQYDPRIFSCTFAQTVSSSYTITVVVHFIVPLSVVTFCYLRIWIVLVIQVKHRV   225
Consensus ---CY--L--W-LT--A--PN---G-LQYDPRI-SCTF-Q-VSS-YTI-VVV-HF-VP----V-FCYLRIW-LV-QV---V VI                                       VII
Sheep     KPDNKPKLKPQDFRNFVTMFVVFVLFAICWAPLNFIGLVVASDPASMAPRIPEWLFVASYYMAYFNSCLNAIIYGLLNQ   315
Human     KPDRKPKLKPQDFRNFVTMFVVFVLFAICWAPLNFIGLAVASDPASMVPRIPEWLFVASYYMAYFNSCLNAIIYGLLNQ   300
Xenopus   RQDFKQKLTQTDLRNFLTMFVVFVLFAVCWAPLNFIGLAVAINPFHVAPKIPEWLFVLSYFMAYFNSCLNAVIYGVLNQ   305
Consensus --D-K--KL-P-D-RNF-TMFVVFVLFA-CWAPLNFIGL-VA--P----P-IPEWLFV-SY-MAYFNSCLNA-IYG-LNQ Sheep     NFRQEYRKIIVSLCTTKMFFVDSSNHVADRIKRKPSPLIANHNLIKVDSV        366   (SEQ ID NO:4)
Human     NFRKEYRRIIVSLCTARVFFVDSSNDVADRVKWKPSPLMTNNNVVKVDSV        350   (SEQ ID NO:12)
Xenopus   NFRKEYKRILMSLLTPRLLFLDTSRGTEGLKSKPSPAVTNNNQADMLGEARSLWLSRRNGAKMVIIRPRKAQIAIEH    384
Consensus NFR-EY---I--SL-T----F-D-S-------KPSP---N-N-------

Xenopus   QIFWPQSSWATCRQDTKITGEEDGCRELCKDGISQR    420    (SEQ ID NO:2)
```

FIG. 8

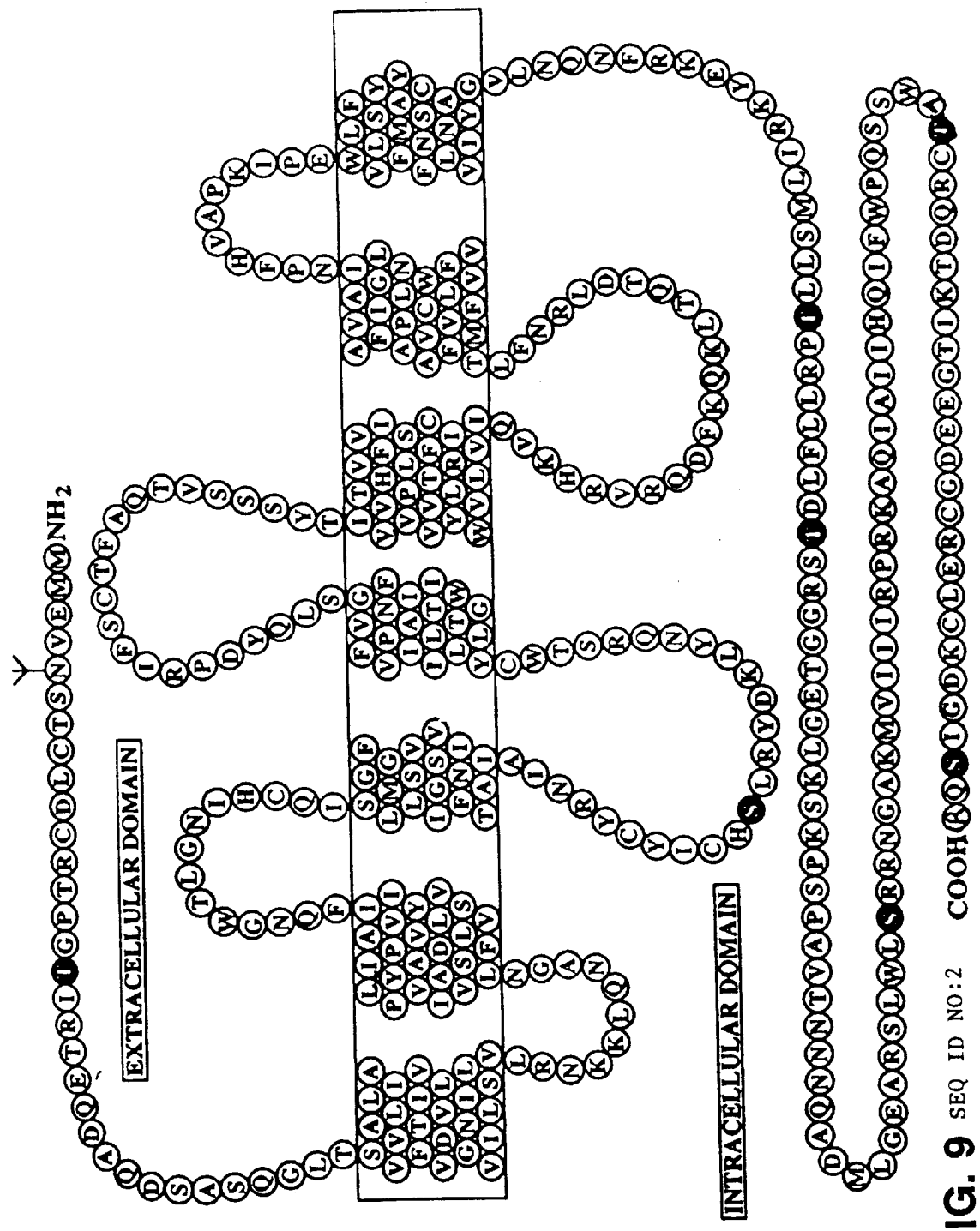
FIG. 9 SEQ ID NO:2

FIG. 18b

DNA ENCODING HIGH-AFFINITY MELATONIN RECEPTORS

CROSS-REFERENCE TO RELATED APPLICATIONS

This application is a continuation-in-part of our earlier filed U.S. application Ser. No. 08/319,887 filed Oct. 7, 1994 now abandoned, which application is a continuation-in-part of our earlier filed U.S. application Ser. No. 08/261,857 filed Jun. 17, 1994 now abandoned, which application is incorporated herein by reference in its entirety and to which application we claim priority under 35 USC §120.

STATEMENT AS TO FEDERALLY SPONSORED RESEARCH

This invention was made at least in part with funds from the Federal government, and the government therefore has rights in the invention.

BACKGROUND OF THE INVENTION

The invention relates to nucleic acids and their encoded high-affinity melatonin receptor proteins.

The high-affinity melatonin receptor is a membrane protein that is coupled to guanine nucleotide binding proteins (G proteins). G proteins, in turn, communicate ligand-activated receptor signals to the appropriate intracellular effector system(s). The hormone, melatonin, inhibits adenylyl cyclase causing a decrease in intracellular cyclic AMP (cAMP) concentration.

Melatonin, the principal hormone of the vertebrate pineal gland, elicits potent neurobiological effects. Melatonin influences circadian rhythm and mediates the effects of photoperiod on reproductive function in seasonally breeding mammals. In humans, melatonin administration has been shown to alleviate the symptoms of jet lag after air travel across several time zones. The hormone also has potent sedative effects in humans and may be a useful hypnotic agent.

Melatonin exerts its photoperiodic and circadian effects through pharmacologically specific, high-affinity receptors (Dubocovich, M. L. and Takahashi, J., P.N.A.S. USA (1987) 84:3916–3920; Vanecek, J., J. Neurochem. (1988) 51:1436–1440; Reppert et al., (1988) supra). In seasonally breeding mammals, pineal melatonin secretion regulates seasonal responses to changes in day length (Bartness, T. J. and Goldman, B. D., Experientia (1989) 45:939–945; Karsch et al., Recent Prog. Horm. Res. (1984) 40:185–232). The only site containing melatonin 1a receptors in all photoperiodic species examined to date (Weaver, et al., Suprachiasmatic nucleus: the mind's clock. Klein, D. C., Moore, R. Y, and Reppert, S. M., eds. New York: Oxford University Press; (1991) pp. 289–308) is the pars tuberalis (PT), a portion of the pituitary gland. In contrast to other species, in humans melatonin 1a receptors are not consistently present in the PT.

High-affinity melatonin-1a (Mel-1a) receptors are located in discrete regions of the vertebrate central nervous system of several mammalian species, including humans. Binding studies using the ligand 2-[$^{125}$I]-iodomelatonin ($^{125}$I-melatonin or [$^{125}$I]MEL) have identified high-affinity melatonin 1a receptors ($K_d$<$2\times10^{-10}$M) in sites such as the suprachiasmatic nuclei (SCN), the site of a biological clock that regulates numerous circadian rhythms (Reppert et al., Science (1988) 242:78–81). To date, high-affinity melatonin receptors have not been identified in central nervous system tissues other than brain.

Receptor affinity is sensitive to guanine nucleotides and activation of the receptors consistently leads to the inhibition of adenylyl cyclase through a pertussis toxin-sensitive mechanism (Rivkees, S. A. et al., P.N.A.S. USA (1989) 86:3883–3886; Carlson, L. L. et al., Endocrinology (1989) 125:2670–2676; Morgan, P. J. et al., Neuroendocrinology (1989) 50:358–362; Morgan, P. J. et al., J. Neuroendocrinol. (1990) 2:773–776; Laitinen, J. T. and Saavedra, J. M., Endocrinology (1990) 126:2110–2115). High-affinity melatonin receptors thus appear to belong to the superfamily of G protein-coupled receptors.

SUMMARY OF THE INVENTION

In general, the invention features substantially pure DNA (cDNA or genomic DNA) encoding a high-affinity melatonin 1a receptor in brain and melatonin 1b receptor in retina. The invention also features substantially pure high-affinity melatonin 1a and 1b receptor polypeptides. In preferred embodiments, the receptor includes an amino acid sequence substantially identical to the amino acid sequence shown in FIG. 1 (SEQ ID NO:2); FIG. 2 (SEQ ID NO:4); FIG. 3 (SEQ ID NO:14); FIG. 5 (SEQ ID NO:12) or comprising the amino acid sequence of FIG. 4 (SEQ ID NO:6) for melatonin-1a receptors.

The invention also features a new class of melatonin receptor designated melatonin-1b (Mel-1b) distinguished by its tissue distribution and binding characteristics. In preferred embodiments, the Mel-1b receptor includes an amino acid sequence substantially identical to the amino acid sequence shown in FIG. 6 (SEQ ID NO:16).

The invention includes a polypeptide having an amino acid sequence which includes a domain capable of binding melatonin and bringing about a decrease in intracellular cAMP concentration, and which is at least 80% identical to the amino acid sequence shown in FIGS. 1–6. The invention also features a substantially pure polypeptide which is a fragment or analog of a high-affinity melatonin-1a or melatonin-1b receptor and which includes a domain capable of binding melatonin and bringing about a decrease in intracellular cAMP concentration.

In various preferred embodiments, the receptor or receptor fragment is derived from a vertebrate animal, preferably, human, sheep, mouse, or Xenopus laevis.

By "high-affinity melatonin receptor polypeptide" is meant all or part of a vertebrate cell surface protein which specifically binds melatonin and signals the appropriate melatonin-mediated cascade of biological events (e.g., a decrease in intracellular cAMP) concentration. The polypeptide is characterized as having the ligand binding properties (including the agonist and antagonist binding properties) and tissue distribution described herein.

By a "polypeptide" is meant any chain of amino acids, regardless of length or post-translational modification (e.g., glycosylation).

By "substantially pure" is meant that the high-affinity melatonin receptor polypeptide provided by the invention is at least 60%, by weight, free from the proteins and naturally-occurring organic molecules with which it is naturally associated. Preferably, the preparation is at least 75%, more preferably at least 90%, and most preferably at least 99%, by weight, high-affinity melatonin receptor polypeptide. A substantially pure high-affinity melatonin receptor polypeptide may be obtained, for example, by extraction from a natural source; by expression of a recombinant nucleic acid encoding a high-affinity melatonin receptor polypeptide, or by chemically synthesizing the protein. Purity can be measured by any appropriate method, e.g., column chromatography, polyacrylamide gel electrophoresis, or HPLC analysis.

By a "substantially identical" amino acid sequence is meant an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the biological activity of the receptor. Such equivalent receptors can be isolated by extraction from the tissues or cells of any animal which naturally produce such a receptor or which can be induced to do so, using the methods described below, or their equivalent; or can be isolated by chemical synthesis; or can be isolated by standard techniques of recombinant DNA technology, e.g., by isolation of cDNA or genomic DNA encoding such a receptor.

By "derived from" is meant encoded by the genome of that organism and present on the surface of a subset of that organism's cells.

In another related aspect, the invention features isolated DNA which encodes a high-affinity melatonin-1a or melatonin-1b receptor (or receptor fragment or analog thereof) described above. Preferably, the purified DNA is cDNA; is cDNA which encodes a *Xenopus laevis* high-affinity melatonin receptor; is cDNA which encodes a sheep high-affinity melatonin-1a receptor; and is cDNA which encodes a human high-affinity melatonin-1a; and is cDNA which encodes a human high-affinity melatonin-1b receptor.

By "isolated DNA" is meant a DNA that is not immediately contiguous with (i.e., covalently linked to) both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

In other related aspects, the invention features vectors which contain such isolated DNA and which are preferably capable of directing expression of the protein encoded by the DNA in a vector-containing cell; and cells containing such vectors (preferably eukaryotic cells, e.g., CHO cells (ATCC; Cat. No. CCL 61 or COS-7 cells (ATCC; Cat. No. CRL 1651). Preferably, such cells are stably transfected with such isolated DNA.

By "transformed cell" is meant a cell into which (or into an ancestor of which) has been introduced, by means of genetic engineering, a DNA molecule encoding a high-affinity melatonin receptor (or a fragment or analog, thereof). Such a DNA molecule is "positioned for expression" meaning that the DNA molecule is positioned adjacent to a DNA sequence which directs transcription and translation of the sequence (i.e., facilitates the production of the high-affinity melatonin receptor protein, or fragment or analog, thereof).

By "specifically binds", as used herein, is meant an agent, such as melatonin, a melatonin analog or other chemical agent including polypeptides such as an antibody, which binds high-affinity melatonin receptor, receptor polypeptide or a fragment or analog thereof, but which does not substantially bind other molecules in a sample, e.g., a biological sample, which naturally includes a high-affinity melatonin receptor polypeptide. Preferably, the agent activates or inhibits the biological activity in vivo of the protein to which it binds. By "biological activity" is meant the ability of the high-affinity melatonin receptor to bind melatonin and signal the appropriate cascade of biological events (as described herein).

In yet another aspect, the invention features a method of screening candidate compounds for their ability to act as an agonist of a high-affinity melatonin-1a or melatonin-1b receptor ligand. The method involves:

a) contacting a candidate agonist compound with a recombinant high-affinity melatonin receptor (or melatonin-binding fragment or analog);

b) measuring binding of the ligand to the receptor, the receptor polypeptide or the receptor fragment or analog; and c) identifying agonist compounds as those which bind the recombinant receptor and trigger a decrease in intracellular cAMP concentration.

By an "agonist" is meant a molecule which mimics a particular activity, in this case, the ability of a high-affinity melatonin receptor ligand to bind a high-affinity melatonin receptor and to trigger the biological events resulting from such an interaction (e.g., decreased intracellular cAMP concentration). An agonist may possess greater activity than the naturally-occurring high-affinity melatonin receptor ligand.

In yet another aspect, the invention features a method of screening a candidate compound for its ability to antagonize interaction between melatonin and a high-affinity melatonin receptor. The method involves:

a) contacting a candidate antagonist compound with a first compound which includes a recombinant high-affinity melatonin receptor (or melatonin-binding fragment or analog) on the one hand and with a second compound which includes melatonin on the other hand;

b) determining whether the first and second compounds bind; and c) identifying antagonistic compounds as those which interfere with the binding of the first compound to the second compound and which reduce melatonin-mediated decreases in intracellular cAMP concentration.

By an "antagonist" is meant a molecule which inhibits a particular activity, in this case, the ability of melatonin to interact with a high-affinity melatonin receptor and to trigger the biological events resulting from such an interaction (e.g., decreased intracellular cAMP concentration.)

In preferred embodiments of both screening methods, the recombinant high-affinity melatonin receptor is stably expressed by a mammalian cell which normally presents substantially no high-affinity melatonin receptor on its surface (i.e., a cell which does not exhibit any significant melatonin-mediated decrease in intracellular cAMP concentration); the mammalian cell is a CHO cell or a COS-7 cell; and the candidate antagonist or candidate agonist is a melatonin analog or other chemical agent including a polypeptide such as an antibody.

The receptor proteins of the invention are likely involved in the control of vertebrate circadian rhythm. Such proteins are therefore useful to develop therapeutics to treat such conditions as jet lag, facilitate reentrainment of some endogenous melatonin rhythms, synchronize the disturbed sleep-wake cycle of blind people, alleviate sleep disorders in shift workers, facilitate the emergence of a diurnal sleep-wake pattern in neonates, regulate ovarian cyclicity in human females, control the initiation and timing of puberty in humans, and alter the mating cycle in seasonally breeding animals, such as sheep. Preferred therapeutics include 1) agonists, e.g., melatonin analogs or other compounds which mimic the action of melatonin upon interaction with the high affinity melatonin receptor; and 2) antagonists, e.g., melatonin analogs, antibodies, or other compounds, which block melatonin or high-affinity melatonin receptor function by interfering with the melatonin:receptor interaction.

A "transgenic animal" as used herein denotes an animmal (such as a non-human mammal) bearing in some or all of its nucleated cells one or more genes derived from a different species (exogenous); if the cells bearing the exogenous gene include cells of the animal's germline, the gene may be transmissible to the animal's offspring. As used herein, genes derived from a different species of animal are exogenous genes. Preferably the exogenous genes include nucleotide sequences which effect expression of the gene in its endogenous tissue distribution.

Because the receptor component may now be produced by recombinant techniques and because candidate agonists and antagonists may be screened using transformed, cultured cells, the instant invention provides a simple and rapid approach to the identification of useful therapeutics. Such an approach was previously difficult because of the localization of the receptor to a few discrete regions in the central nervous system of most mammals. Isolation of the high-affinity melatonin receptor gene (as cDNA) allows its expression in a cell type which does not normally bear high-affinity melatonin receptors on its surface, providing a system for assaying a melatonin:receptor interaction.

Other features and advantages of the invention will be apparent from the following description of the preferred embodiments thereof, and from the claims.

DETAILED DESCRIPTION

The drawings will first briefly be described.
Drawings

FIG. 1 is the complete nucleotide and amino acid sequences (SEQ ID NO:1 and SEQ ID NO:2, respectively) of the *Xenopus laevis* high-affinity melatonin receptor gene coding region cDNA. The deduced amino acid sequence of the receptor is provided below the nucleotide sequence (reading frame b) and contains 420 amino acids. The deduced amino acid sequence begins at nucleotides 32, 33, 34 (ATG=Met) and ends with nucleotides 1292, 1293, 1294 (TGA=stop).

FIG. 2 is the complete nucleotide and amino acid sequences (SEQ ID NO:3 and SEQ ID NO:4, respectively) of the sheep high-affinity melatonin-1a receptor gene coding region which is a genetic fusion of genomic DNA from the 5' region and cDNA from the 3' region as described below. The deduced amino acid sequence of the receptor is provided below the nucleotide sequence and contains (reading fame a) 366 amino acids. The deduced amino acid sequence begins at nucleotides 49, 50, 51 (ATG=Met) and ends at nucleotides 1147, 1148, 1149 (TAA=stop).

FIG. 3 is the complete nucleotide and amino acid sequences (SEQ ID NO:13 and SEQ ID NO:14, respectively) of the mouse high-affinity melatonin-1a receptor gene coding region. The deduced amino acid sequence of the receptor is provided below the nucleotide sequence and contains (reading frame a) 353 amino acids. The deduced amino acid sequence begins at nucleotides 1–3 (ATG=Met) and ends at nucleotides 1060–1062 (TAA=stop).

FIG. 4 is the nucleotide and deduced amino acid sequences (SEQ ID NO:5 and SEQ ID NO:6, respectively) of a fragment of the human high-affinity melatonin receptor gene coding region genomic DNA. The coding sequence corresponds to the region downstream (3') of the first intron. From the sequenced portion of the receptor DNA, the deduced amino acid sequence is provided below the nucleotide sequence (reading frame a) and contains 288 amino acids. The coding region of the partial sequence begins at nucleotides 1, 2, 3 (GGA=Gly) and ends at nucleotides 865, 866, 867 (TAA=stop).

FIG. 5 is the complete nucleotide and amino acid sequences (SEQ ID NO:11 and SEQ ID NO:12, respectively) of the human high-affinity melatonin receptor cDNA. The deduced amino acid sequence of the receptor is provided below the nucleotide sequence (reading frame c) beginning at nucleotides 33–35 (ATG=Met) and contains 350 amino acids ending at nucleotides 1083–1085 (TAA=stop).

FIG. 6 is the complete nucleotide and amino acid sequences (SEQ ID NO:15 and SEQ ID NO:16, respectively) of the human high-affinity melatonin-1b receptor cDNA. The deduced amino acid sequence of the receptor is provided below the nucleotide sequence (reading frame a) beginning at nucleotides 13–15 (ATG=Met), ending at nucleotides 1096–1098 (TAA=stop) and contains amino 362 acids.

FIG. 7 shows the alignment of the deduced amino acid sequences (SEQ ID NO:2, SEQ ID NO:4, and SEQ ID NO:6, respectively) and the hydrophobic regions (boxes I–VII) of the entire Xenopus and sheep, and partial human high-affinity melatonin receptors.

FIG. 8 shows the alignment of the deduced amino acid sequences (SEQ ID NO:2, SEQ ID NO:4, and SEQ ID NO:12, respectively) and the hydrophobic regions (presumed transmembrane domains I–VII highlighted by solid bars) of the entire Xenopus, sheep, and human high affinity melatonin receptors. To indicate homology, gaps (represented by dots) have been introduced into the three sequences.

FIG. 9 is the proposed structure of the Xenopus high-affinity melatonin receptor in the cell membrane. The deduced amino acid sequence (SEQ ID NO:2) is depicted. Y, potential N-linked glycosylation site. Solid circles represent consensus sites for protein kinase C phosphorylation.

Figure 10A:
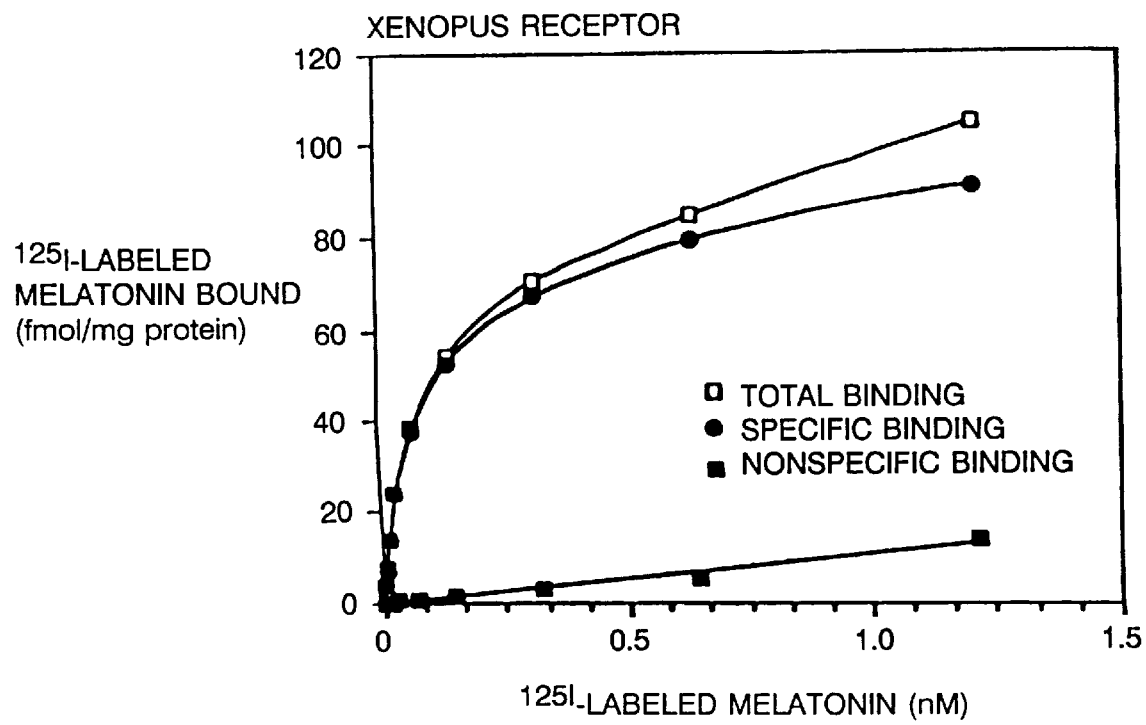
Figure 10B:
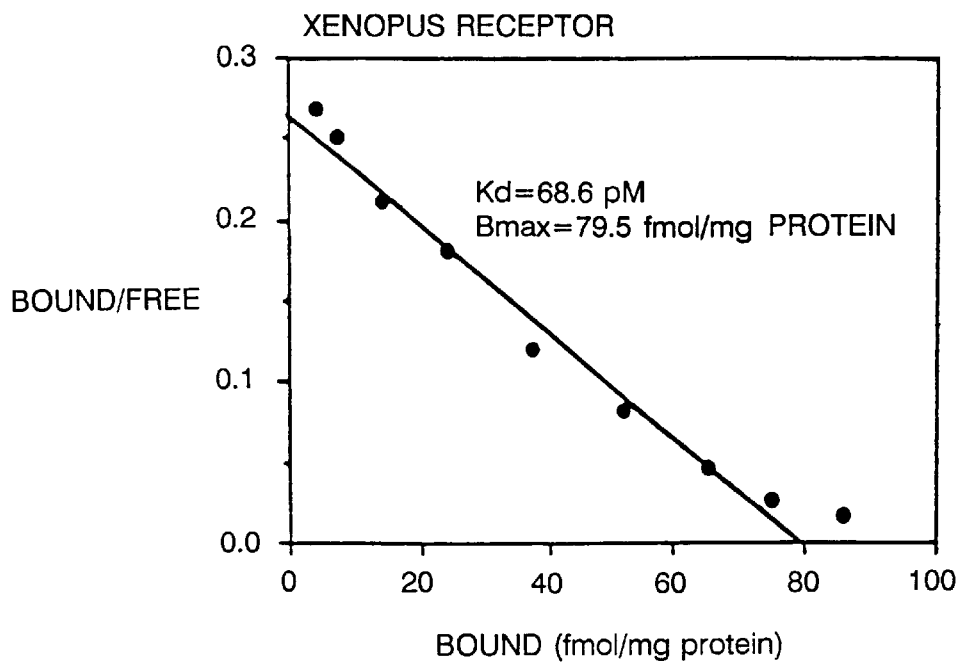

FIGS. 10a and 10b show $^{125}$I-melatonin binding assay results from COS-7 cells containing Xenopus melatonin receptor cDNA. FIG. 11a shows a saturation curve. Nonspecific binding was determined using 10 $\mu$M melatonin. FIG. 11b shows a single representative Scatchard plot of the saturation data for determining the relative $^{125}$I-melatonin binding constants for the transfected high-affinity melatonin receptor gene from Xenopus.

Figure 11:
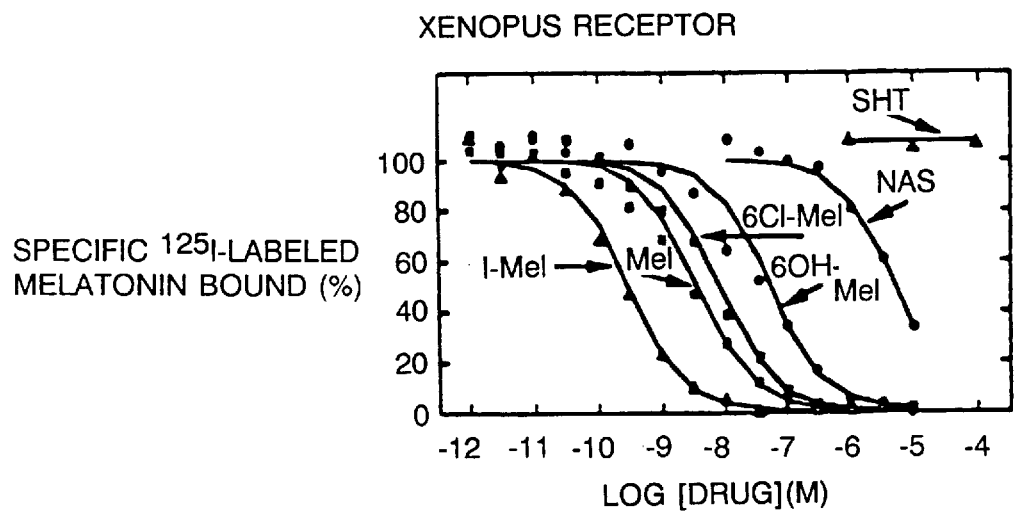

FIG. 11 shows competition by various ligands for $^{125}$I-melatonin binding in COS-7 cells transfected with the melatonin receptor cDNA from Xenopus. Cells were incubated with 100 pM $^{125}$I-melatonin and various concentrations of 2-iodomelatonin (I-MEL), melatonin (MEL), 6-chloromelatonin (6Cl-MEL), 6-hydroxymelatonin (6OH-MEL), N-acetyl-5-hydroxytryptamine (NAS), or 5-hydroxytryptamine (5HT). Nonspecific binding was determined in the presence of 10 $\mu$M melatonin. $K_i$ values are: I-MEL, $1.1\times10^{-10}$M; MEL, $1.3\times10^{-9}$M; 6Cl-MEL, $3.0\times10^{-9}$M; 6OH-MEL, $2.0\times10^{-8}$M; NAS, $2.0\times10^{-6}$M; 5HT, $>1.0\times10^{-4}$M. The data are representative of three experiments.

Figure 12:
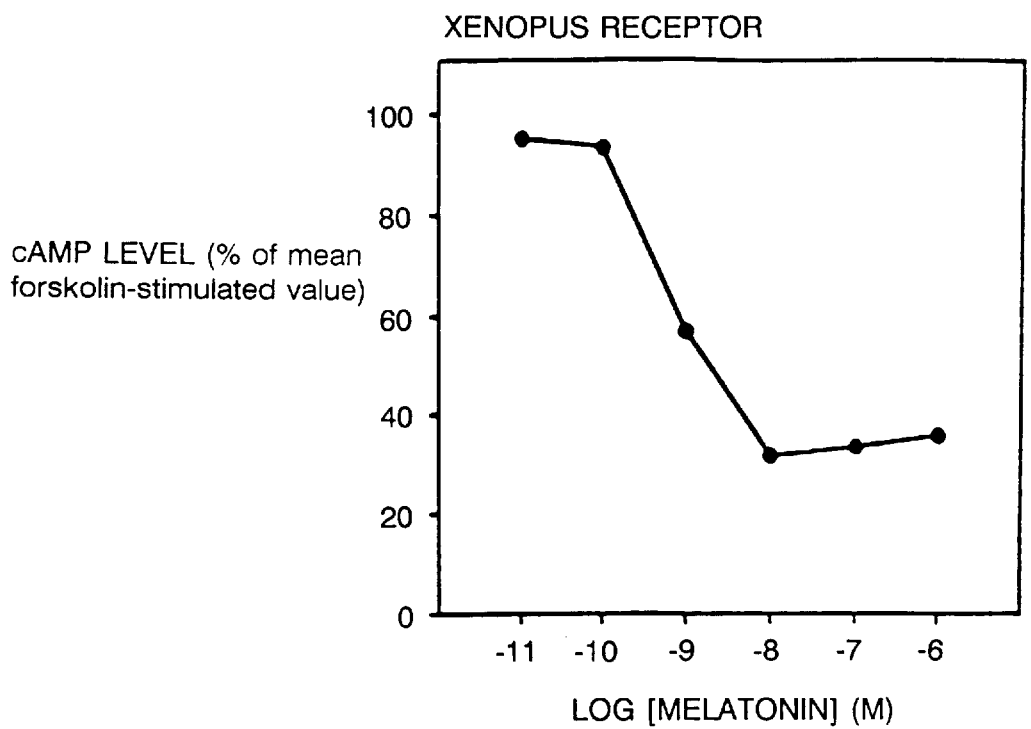

FIG. 12 shows melatonin inhibition of forskolin-stimulated cAMP accumulation in CHO cells stably transfected with the melatonin receptor cDNA from Xenopus. The 100% value is the mean cAMP value induced with 10 μM forskolin. The data are representative of three experiments.

Figure 13:
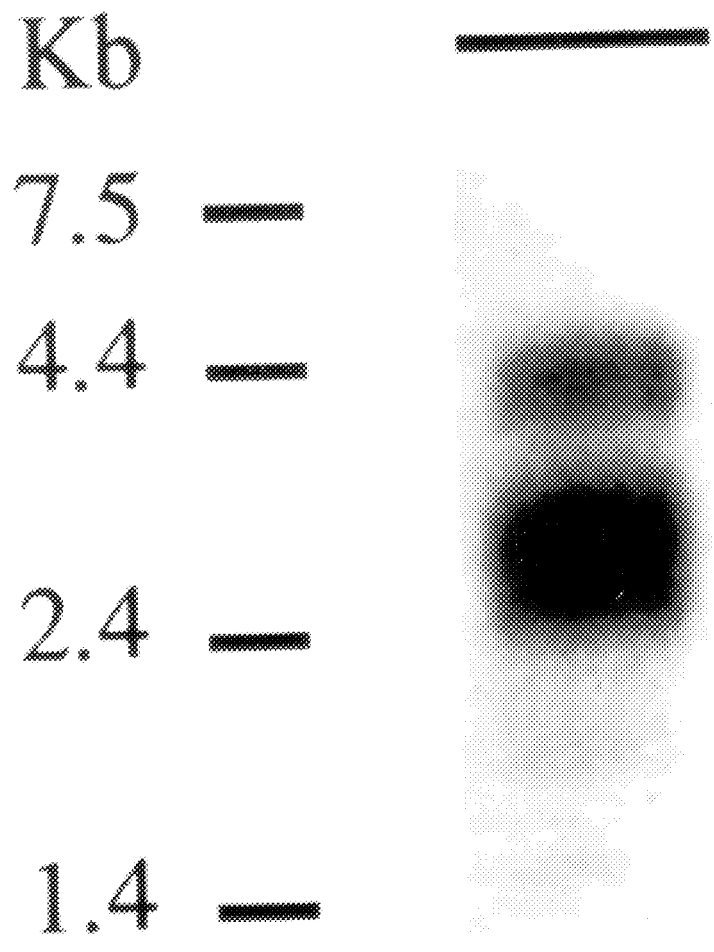

FIG. 13 is a Northern blot of melatonin receptor transcripts in Xenopus derived melanophores. Locations of RNA size markers (Life Technologies, Bethesda, Md.) are indicated. The blot was exposed to X-ray film overnight.

Figure 14A:
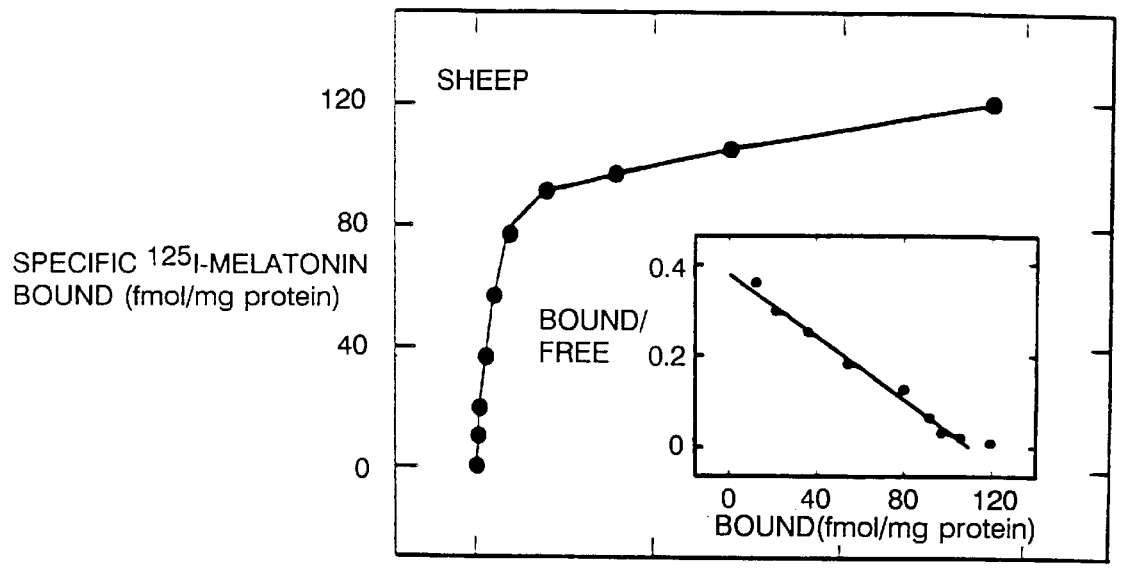
Figure 14B:
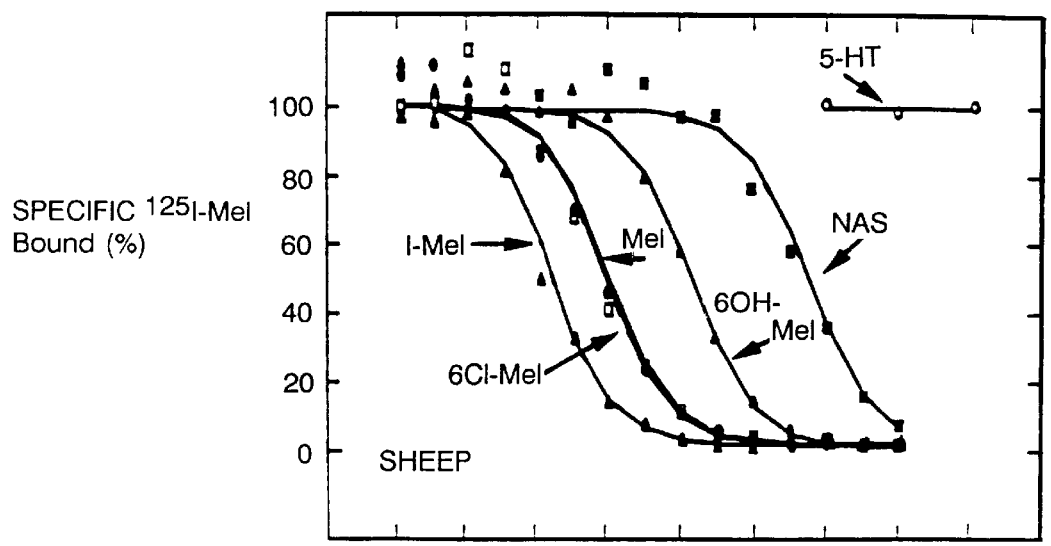

FIG. 14 shows $^{125}$I-melatonin binding assay results from COS-7 cells containing sheep melatonin receptor cDNA. FIG. 14a shows a saturation curve. Nonspecific binding was determined using 10 μM melatonin. FIG. 14a (inset) shows a Scatchard plot of the saturation data for determining the relative $^{125}$I-melatonin binding constants for the transfected high-affinity melatonin receptor gene from sheep. The $K_d$ value for the sheep melatonin high-affinity receptor is 3.6× $10^{-11}$M and the $B_{max}$ value is 104 fmol/mg protein. Nonspecific binding was determined using 10 μM melatonin. Data shown are representative of three experiments. FIG. 14b is a plot of competition by various ligands for $^{125}$I-Mel binding in COS-7 cells transfected with the sheep melatonin receptor cDNA (SEQ ID NO:3). Cells were incubated with 100 pM $^{125}$I-Mel and various concentrations of 2-iodomelatonin (I-Mel), melatonin (Mel), 6-chloromelatonin (6Cl-Mel), 6-hydroxymelatonin (6OH-Mel), N-acetyl-5-hydroxytryptamine (NAS), or 5-hydroxytryptamine (5-HT). Nonspecific binding was determined in the presence of 10 μM melatonin. $K_i$ values for the sheep receptor are: I-Mel, 3.7×$10^{-11}$M; Mel, 2.4× $10^{-10}$M; 6Cl-Mel, 2.5×$10^{-10}$M; 6OH-Mel, 3.0×$10^{-9}$M; NAS, 1.4×$10^{-7}$M; 5HT, >1.0×$10^{-4}$M. Inhibition curves were generated by LIGAND (Munson, P. L. and Rodbard, D. Anal. Biochem. (1980) 107:220–239) using a one-site model. The data shown are representative of at least three experiments. 2-Iodomelatonin is available from Research Biochemicals Inc., Natick, Mass.; 6-chloromelatonin is available from Ely Lily, Indianapolis, Ind.; all other drugs used herein are available from Sigma, St. Louis, Mo.

Figure 15A:
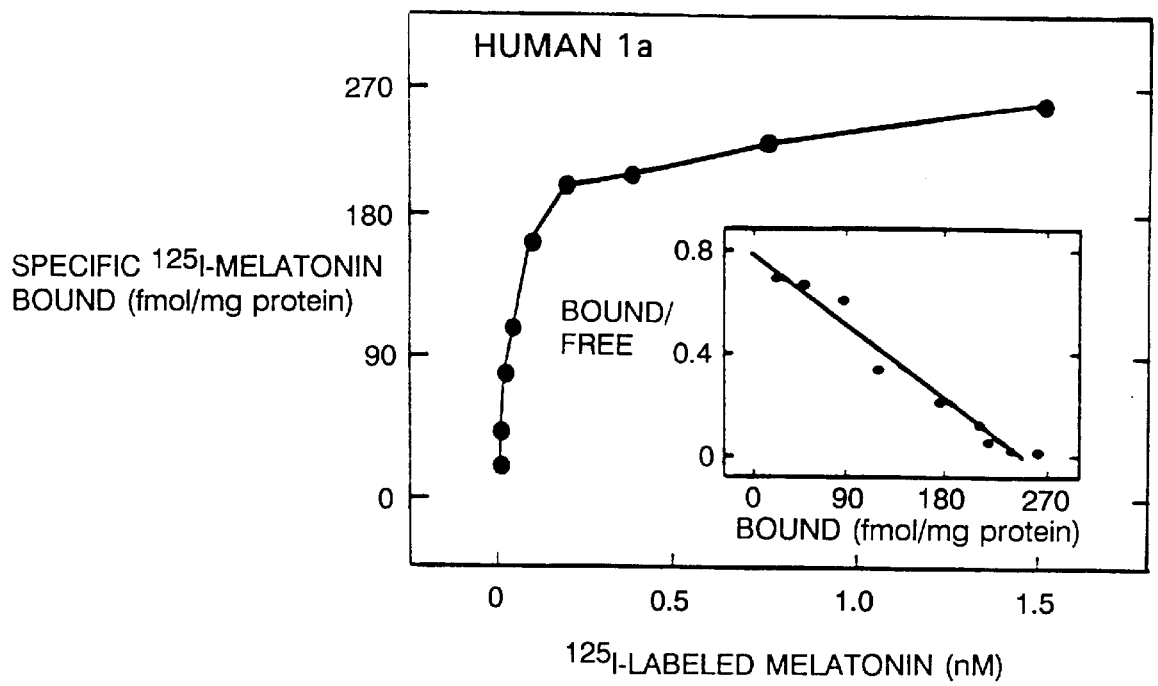
Figure 15B:
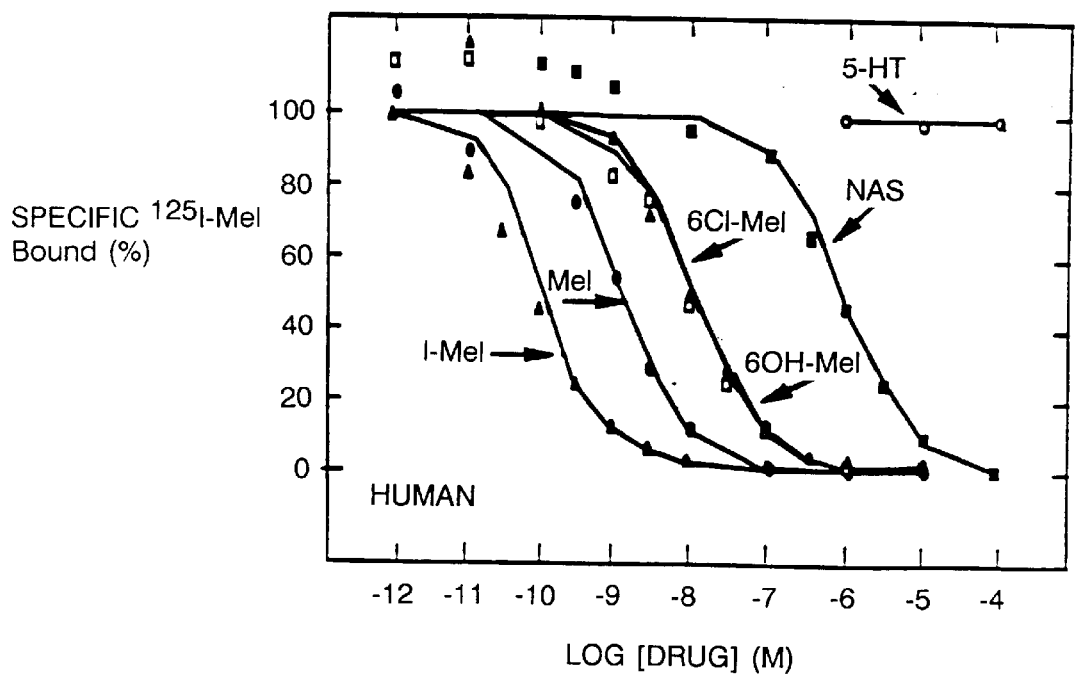

FIG. 15 shows $^{125}$I-melatonin binding assay results from COS-7 cells containing the complete human melatonin 1a receptor cDNA (SEQ ID NO:11). FIG. 15a shows a saturation curve. FIG. 15a (inset) shows Scatchard plot of the saturation data for determining the relative $^{125}$I-melatonin binding constants for the transfected high-affinity melatonin receptor gene from human. The $K_d$ value for the human high-affinity melatonin 1a receptor is 2.6×$10^{-11}$M and the $B_{max}$ value is 220 fmol/mg protein. Nonspecific binding was determined using 10 μM melatonin. Data shown are representative of three experiments. FIG. 15b is a plot of competition by various ligands for $^{125}$I-Mel binding in COS-7 cells transfected with the human melatonin receptor cDNA (SEQ ID NO:11). Cells were incubated with 100 pM $^{125}$I-Mel and various concentrations of 2-iodomelatonin (I-Mel), melatonin (Mel), 6-chloromelatonin (6Cl-Mel), 6-hydroxymelatonin (6OH-Mel), N-acetyl-5-hydroxytryptamine (NAS), or 5-hydroxytryptamine (5-HT). Nonspecific binding was determined in the presence of 10 μM melatonin. $K_i$ values for the human receptor are: I-Mel, 1.8×$10^{-11}$M; Mel, 2.3×$10^{-10}$M; 6Cl-Mel, 2.0×$10^{-9}$M; 6OH-Mel, 2.0×$10^{-9}$M; NAS, 1.7×$10^{-7}$M; 5HT, >1.0×$10^{-4}$M. Inhibition curves were generated by LIGAND (Munson and Rodbard (1980), supra) using a one-site model. The data shown are representative of at least three experiments.

Figure 16A:
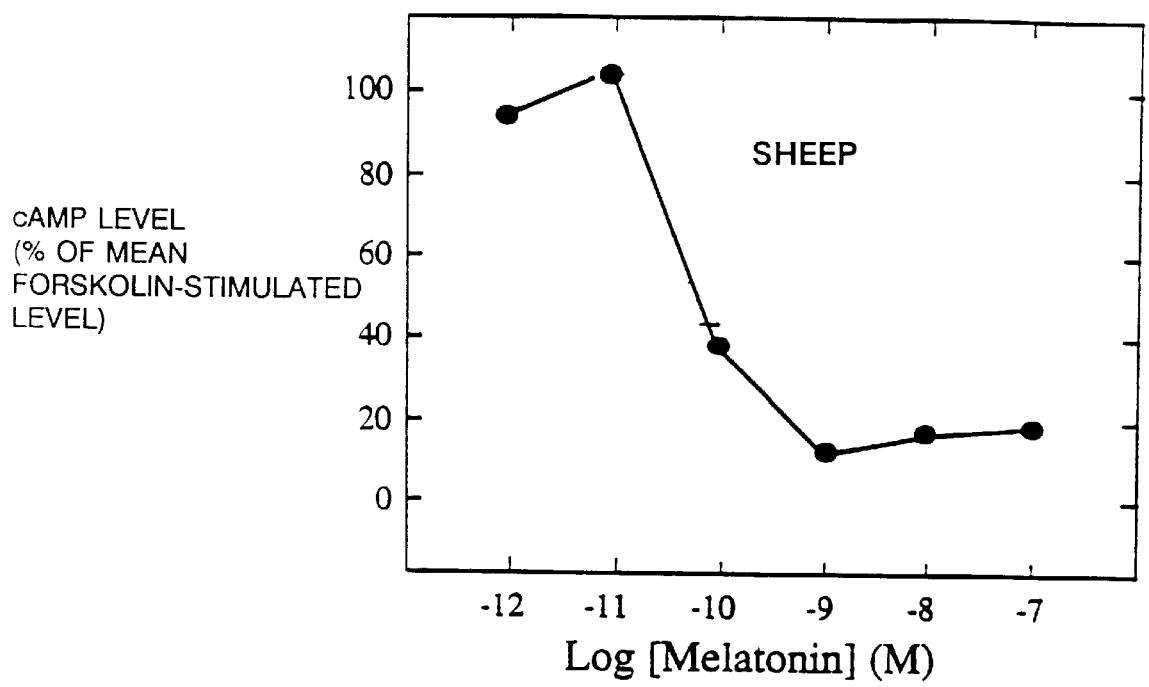
Figure 16B:
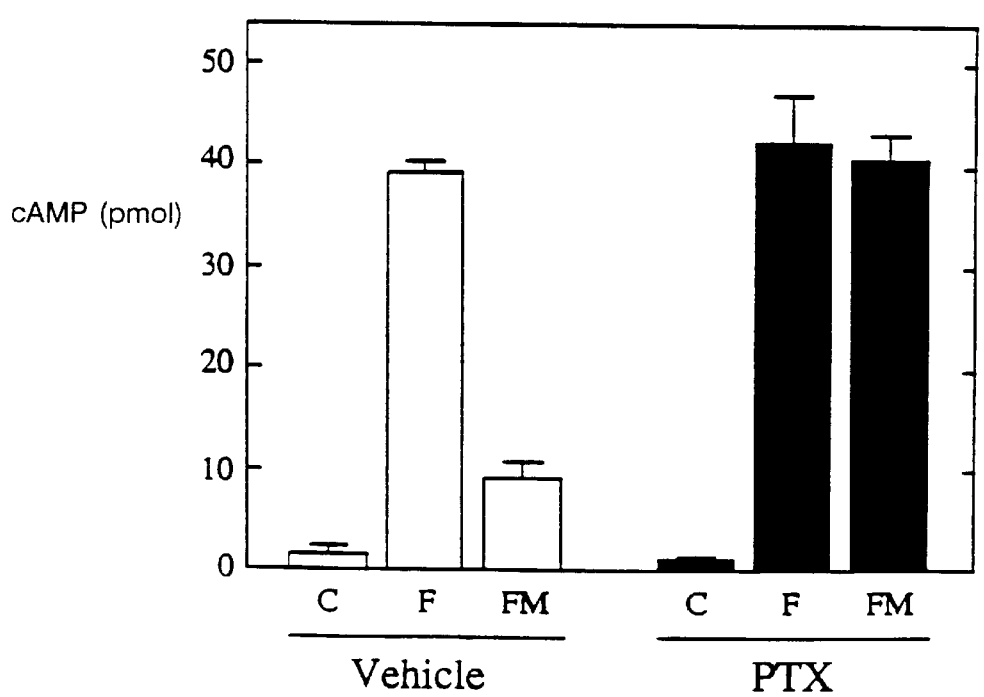

FIG. 16 is the results of studies showing that recombinant mammalian melatonin receptor couples to $G_i$. FIG. 16a shows melatonin inhibition of forskolin-stimulated cAMP accumulation in NIH 3T3 cells stably transfected with the sheep melatonin receptor cDNA (SEQ ID NO:3). The 100% value is the mean cAMP value induced with 10 μM forskolin. The data shown are representative of four experiments. FIG. 16b shows that pertussis toxin blocks the ability of melatonin to inhibit forskolin-stimulated cAMP accumulation in NIH 3T3 cells stably transfected with the sheep melatonin receptor cDNA (SEQ ID NO:3). Cells were preincubated with either vehicle or pertussis toxin for 18 hours (PTX: 100 ng/ml; pertussis toxin was purchased from List, Campbell, Calif.). C, Basal levels; F, 10 μM forskolin alone; FM, 10 μM forskolin plus 1 μM melatonin. Data are the mean plus standard deviation for 3 plates for each treatment. The data shown are representative of three experiments.

Figures 17A, 17B, 17C:
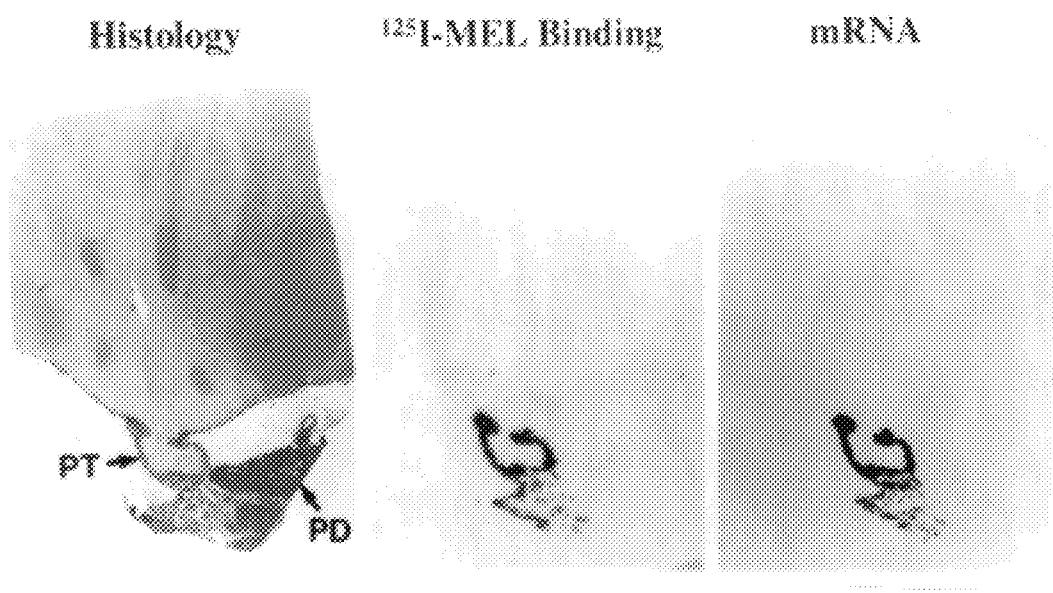

FIG. 17 shows a coronal section through the base of the sheep brain and pituitary. FIG. 17a is a histographic staining of the tissue section showing the pars tuberalis (PT) and the pars distalis (PD). FIG. 17b is a film autoradiographic image produced from a section to which [$^{125}$I]MEL binding is observed in the PT. FIG. 17c is a film autoradiographic image produced from an in situ hybridization of a tissue section using a sheep high-affinity melatonin receptor riboprobe derived from the cloned receptor sequence. The hybridization pattern shows that mRNA which hybridizes to the sheep high-affinity melatonin receptor riboprobe exhibits the same pattern of expression as the endogenous receptor protein.

Figure 18A:
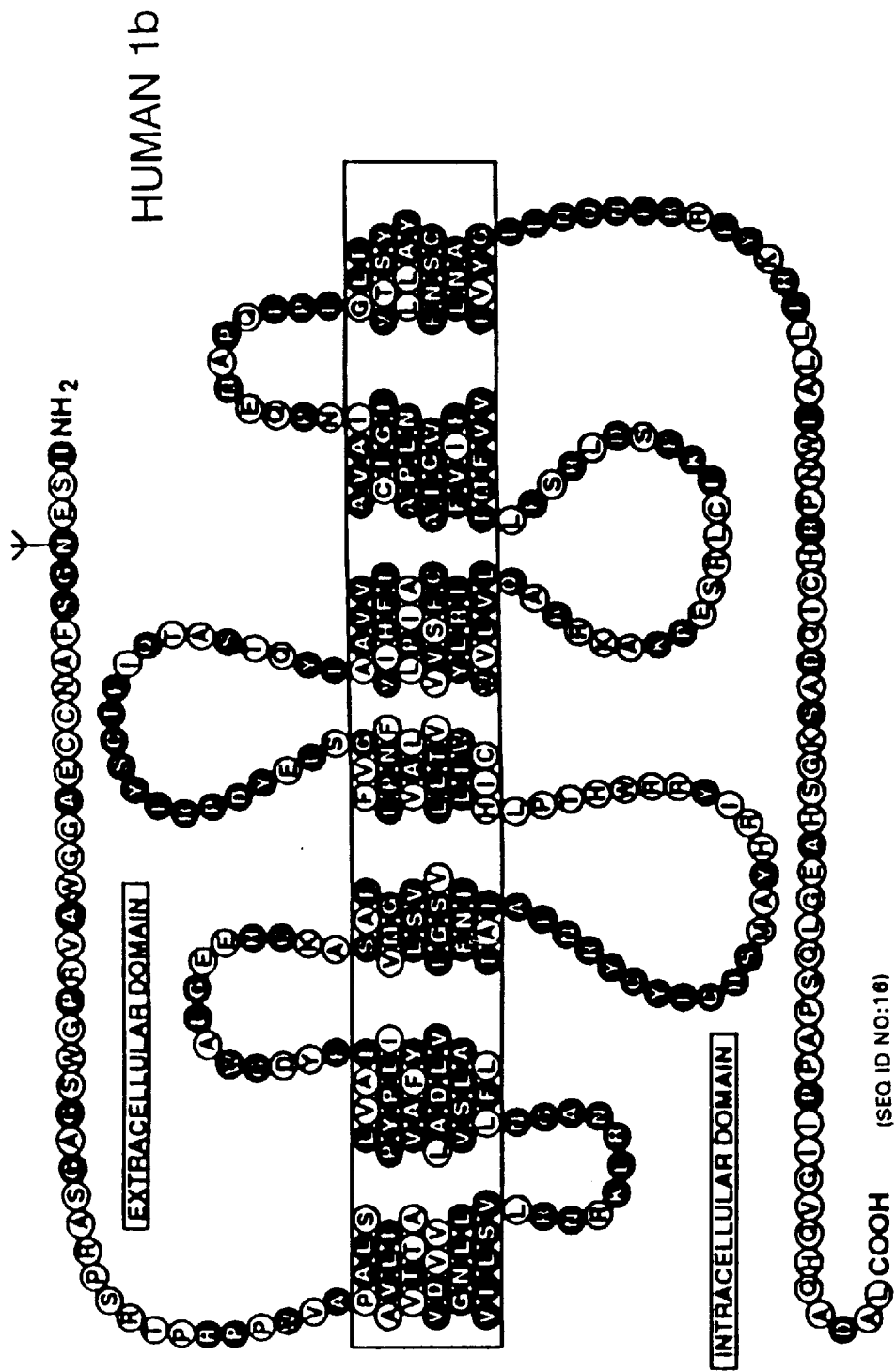

FIG. 18 is a diagram of the structure of the human Mel-1b receptor protein. FIG. 18a is the predicted membrane topology of the human Mel-1b receptor protein. Y, Potential N-linked glycosylation site. Amino acids that are shaded are identical between human Mel-1b and the human Mel-1a melatonin receptors. FIG. 18b is a comparison of the deduced amino acid sequence of human Mel-1b and the human Mel-1a melatonin receptor (GenBank accesssion no. U14109) and the Xenopus melatonin receptor (U09561). To maximize homologies, gaps (dots) have been introduced into the three sequences. The seven presumed transmembrane domains (I–VII) are overlined. Consensus sites for N-linked glycosylation are underlined. The human melaton 1b receptor sequence has been deposited in GenBank under accession number U25341.

Figure 19:
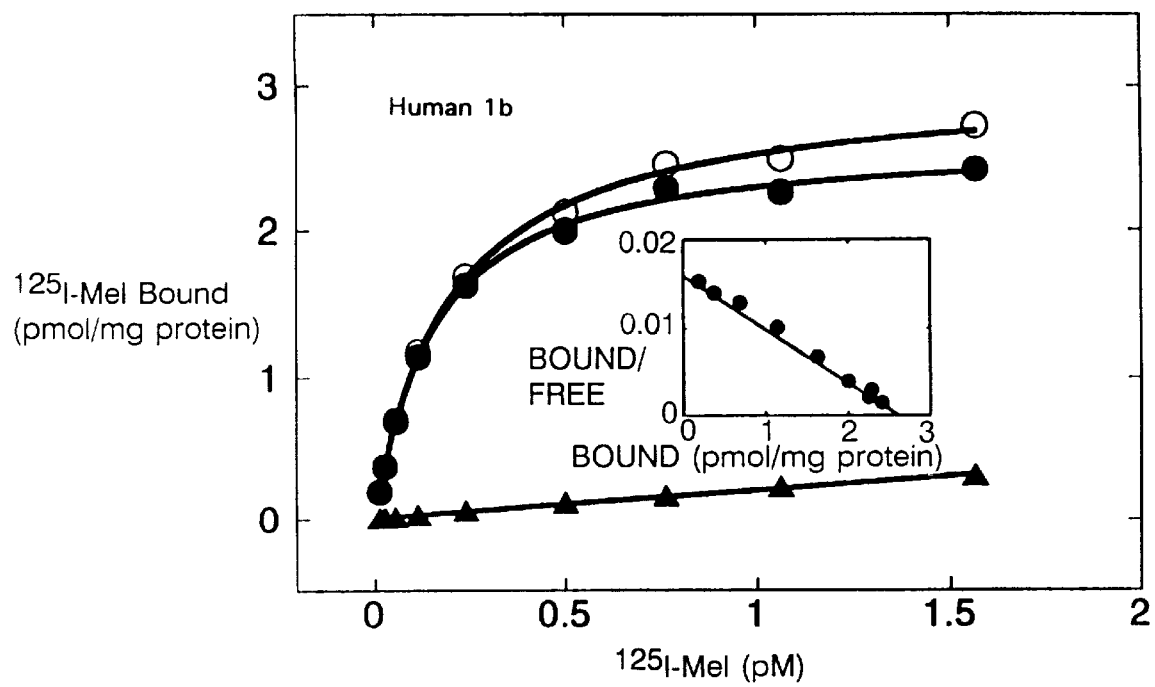

FIG. 19 is a plot of human Mel-1b receptor expression in COS-1 cells assayed by $^{125}$I-Mel binding. ○, total binding; ●, specific binding; ▲, nonspecific binding (determined in the presence of 10 μM melatonin). Inset: Scatchard plot of saturation data. The $K_d$ value depicted is 1.5×$10^{-10}$M. The $B_{max}$ value is 2.62 pmol/mg membrane protein. Data shown are representative of five experiments.

Figure 20:
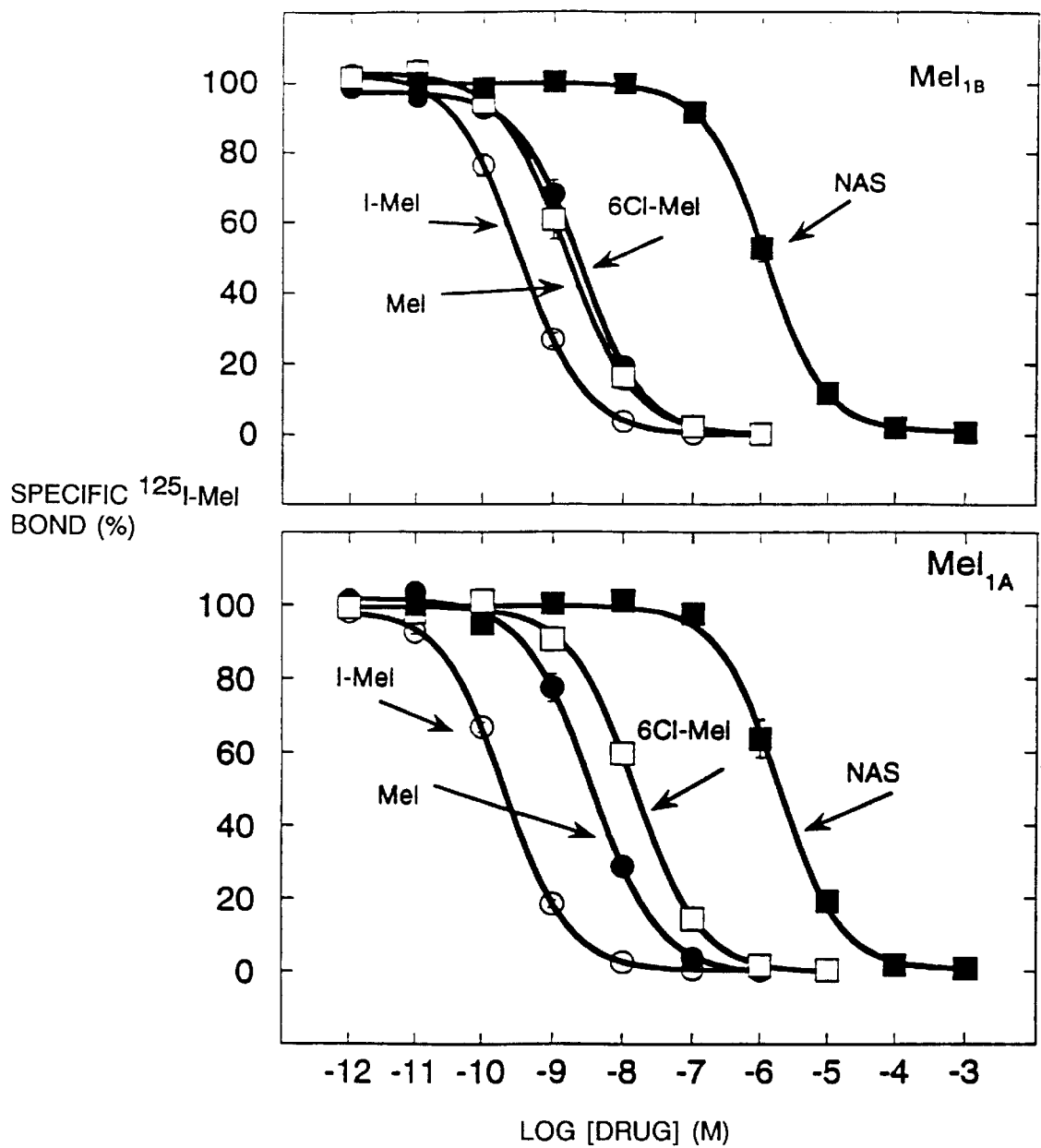

FIG. 20 is a graphical representation of competition by various ligands for $^{125}$I-Mel binding in COS-1 cells transfected with either human Mel-1b or human Mel-1a melatonin receptor cDNA. Cells were incubated with 200 pM (Mel-1b receptor) or 100 pM $^{125}$I-Mel (Mel-1a receptor) and various concentrations of 2-iodomelatonin (I-Mel), melatonin (Mel), 6-chloromelatonin (6Cl-Mel), or N-acetyl-5--hydroxytryptamine (NAS). Nonspecific binding was determined in the presence of 10 μM melatonin. The data shown are mean values of three to five experiments for each drug. $K_i$ values are listed in Table 1.

Figure 21:
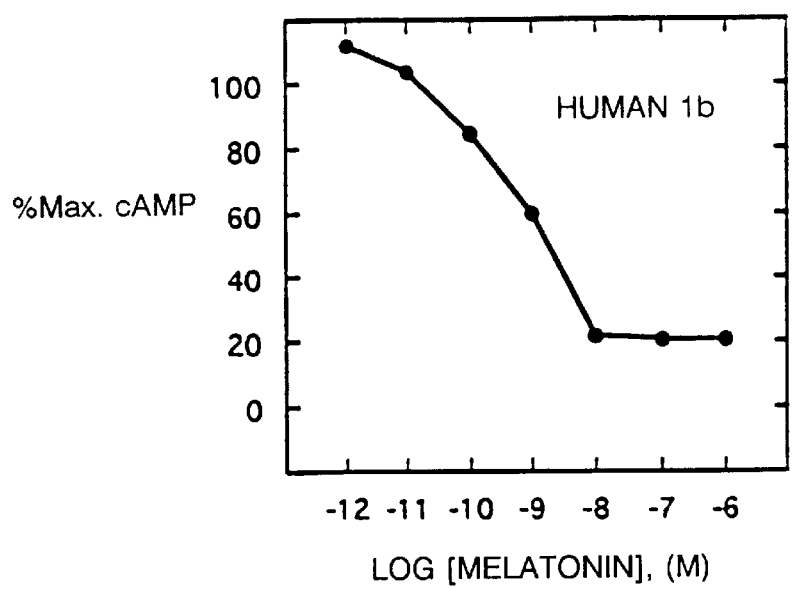

FIG. 21 is a graphical representation of melatonin inhibition of forskolin-stimulated cAMP accumulation in NIH 3T3 cells stably transfected with human Mel-1b receptor. The 100% value is the mean cAMP value induced with 10 μM forskolin. The data shown are mean values of two experiments.

Figure 22:
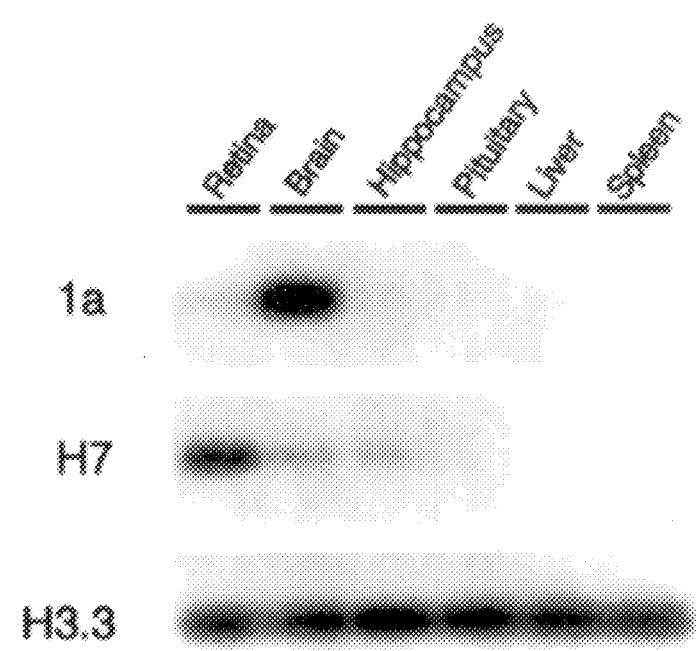

FIG. 22 is a comparative RT-PCR analysis of Mel-1b and Mel-1a receptor gene expression in six human tissues. Brain refers to analysis of whole brain. H3.3 is histone H3.3.

Figure 23:
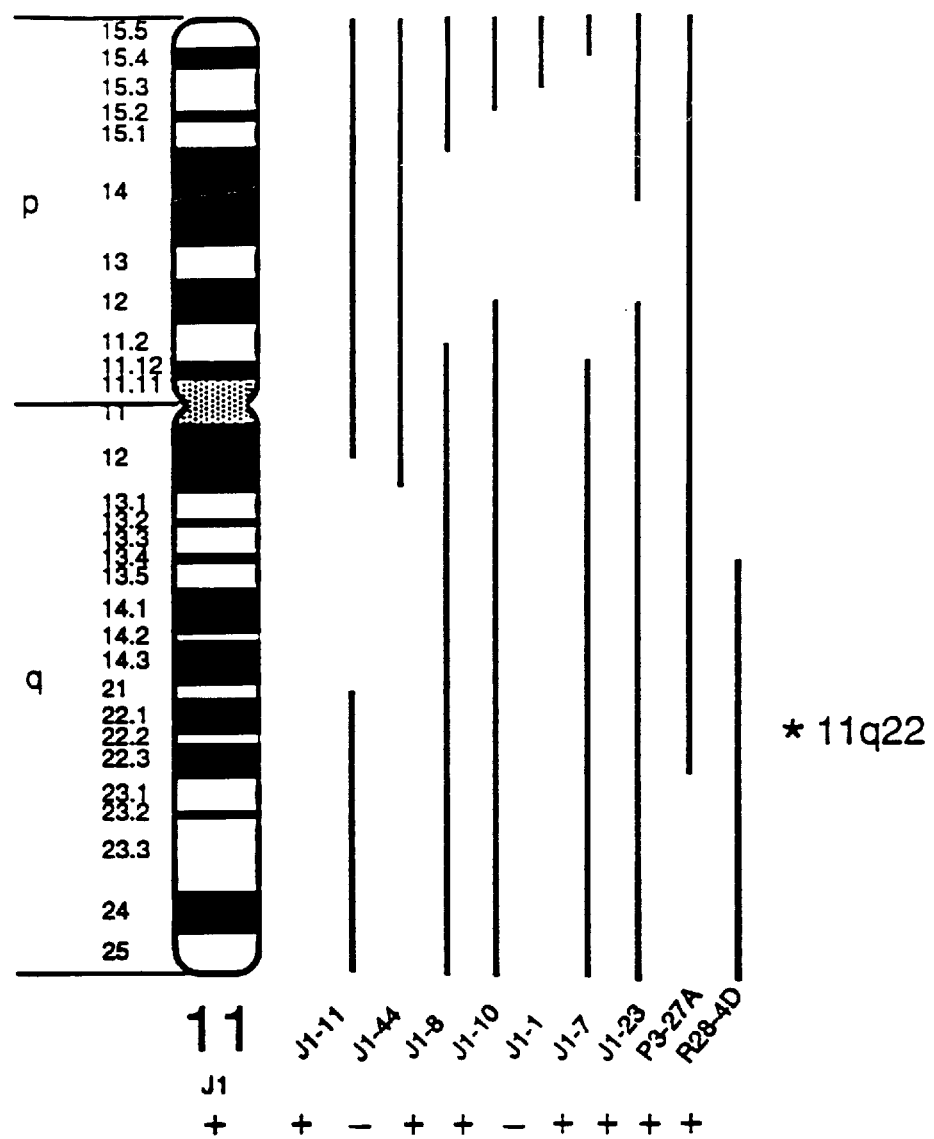

FIG. 23 is a diagram showing the chromosomal location of the Mel-1b receptor gene. The idiogram of human chromosome 11 illustrates the chromosomal content of the somatic cell hybrids used to localize the Mel-1b melatonin receptor gene (MTNR1 B), to 11q21-22.

There now follows a description of the cloning and characterization of the high-affinity melatonin receptor cDNA from *Xenopus laevis*, the high-affinity melatonin 1a receptor from sheep, mouse, and human as well as the high affinity melatonin 1b receptor from human useful in the instant invention. Transformed cells containing and expressing the cDNA of the invention are also described. This example is provided for the purpose of illustrating the invention, and should not be construed as limiting.

Molecular Cloning of a High-Affinity Melatonin Receptor from *Xenopus laevis*

Melatonin receptors are present in the dermal melanophores of amphibians (Bagnara, J. T. and Hadley, M. E., *Am. Zoologist* (1970) 10:201–216). The action of melatonin, mediated through the high-affinity melatonin receptor coupled to $G_i$ protein (Abe, K. et al., *Endocrinology* (1969) 85:674–682; White, B. H. et al., *J. Comp. Physiol.* (1987) B 157:153–159) results in melanin aggregation in the dermal melanophores. mRNA from Xenopus dermal melanophores was used to clone the Xenopus high-affinity melatonin receptor cDNA (Ebisawa, T. et al., PNAS USA (1994) 91:6133–6137). Either primary cells or immortalized cells may be used for the purpose of mRNA isolation. Cloning of the Xenopus high-affinity melatonin receptor cDNA was accomplished as a useful initial step toward cloning of the high-affinity melatonin receptors of higher eukaryotes.

The immortalized cell line used for mRNA isolation was found to express a high level of $^{125}$I-melatonin binding ($\geq$100 fmol/mg total cell protein using 50 pM $^{125}$I-melatonin). The cells were cultured by the method of Daniolos et al. (*Pigment Cell Res.* (1990) 3:38–43). Using standard techniques, total cellular RNA was isolated from melanophores by extraction with guanidinium thiocyanate followed by centrifugal separation in a cesium chloride density gradient (Sambrook et al., *Molecular Cloning: A Laboratory Manual* (Cold Spring Harbour Lab. Press, Plainview, N.Y.), (1989) 2nd Ed.). Removal of melanosomes prior to separation on the cesium chloride density gradient was performed as described by Karne et al. (*J. Biol. Chem.* (1993) 268:19126–19133). Poly(A)$^+$RNA was isolated using established methods as described in Rivkees et al. (*P.N.A.S. USA* (1989) 84:3916–3920).

The poly(A)$^+$RNA from Xenopus dermal melanophores was used as a template for the construction of a random primed cDNA library (cDNA Synthesis Kit, Pharmacia Biotech Inc., Piscataway, N.J.). Cohesive ends were produced on the double stranded cDNA by ligating with BstX1 and EcoR1 adaptors (InVitrogen, San Diego, Calif.). The cDNA was size-fractionated on an agarose gel, and cDNA having a length equal to or greater than 2 kilobase pairs (kb) was recovered by electroelution. The size-selected cDNA was ligated into the expression vector pcDNAI (InVitrogen, San Diego, Calif.) and introduced into *E. coli* strain MC1061/P3 by electroporation.

A total of $4 \times 10^5$ recombinants were obtained from 5 μg of poly(A)$^+$RNA and divided into 54 pools, each containing approximately 7400 clones. Plasmid DNA was prepared from each pool by the alkaline lysis method and transfected into COS-7 cells by the DEAE-dextran method (Cullen, B. R., *Methods Enzymol.* (1987) 152:684–704). COS-7 cells were grown as monolayers in Dulbecco's modified Eagle's medium supplemented with 10% fetal calf serum, penicillin (50 U/ml), and streptomycin (50 μg/ml), in 5% $CO_2$ at 37° C. Three days after transfection, cells were incubated with 90 pM $^{125}$I-melatonin Tris-HCl pH 7.4, containing 100 mM NaCl, 5 mM KCl, 2 mM $CaCl_2$, and 5% Nu-Serum I (Collaborative Biomedical Products, Bedford, Mass.), for 2 hr at room temperature. Cells were washed, air dried, and exposed to X-ray film for 14 days. A pool of clones which showed positive signals was subdivided, and the transfection procedure was repeated. This subdividing process was continued until a single clone was identified that conferred specific $^{125}$I-melatonin binding to COS-7 cells.

This clone, which contained a 2.2 kb cDNA, insert was isolated and both strands of the coding region were sequenced (SEQ ID NO:1). Nucleotide sequences were analyzed by the dideoxynucleotide chain termination method of Sanger, F. et al. (*P.N.A.S. USA* (1977) 74:5463–5467) using Sequenase® (United States Biochemical, Cleveland, Ohio). The sequencing template was double-stranded plasmid DNA. Sequencing primers were synthetic oligonucleotides that were either vector specific or derived from sequence information.

The isolated Xenopus cDNA encodes a protein of 420 amino acids (FIG. 1) (SEQ ID NO:2) with an estimated molecular mass of 47,424. The flanking DNA sequence of the first two methionine codons in this reading frame both displayed a Kozak consensus sequence for the initiation of translation (Kozak, M., *Nucleic Acids Res.* (1987) 15:8125–8148). Hydropathy analysis (Kyte, J. and Doolittle, R. F., *J. Mol. Biol.* (1982) 157:195–232) of the predicted amino acid sequence revealed the presence of seven hydrophobic domains (see FIGS. 4 and 5) which likely represent the transmembrane regions of a G protein-coupled receptor. The amino terminus contains a consensus site for N-linked glycosylation, a feature typical of most G protein-coupled receptors (Pearson, W. R., *Methods Enzymol.* (1990) 183:63–98). The melatonin receptor protein is not similar in identity to any one particular group of G protein-coupled receptors, but is similar to a wide range of receptors; the highest amino acid sequence identity scores were approximately 25% for both the mu opioid and type 2 somatostatin receptors. Using a G protein-coupled receptor database (Kornfeld, R. and Kornfeld, D., *Ann. Rev. Biochem.* (1985) 54:631–664), the melatonin receptor appears to form a group that is distinct from other known biogenic amine and peptide receptors. No sequence homology was identified between the melatonin receptor and the metabotropic glutamate or parathyroid hormone/calcitonin/secretin receptor gene families (Masu et al., *Nature* (1991) 349:760–765; Juppner, et al., *Science* (1991) 254:1024–1026; Lin et al., *Science* (1991) 254:1022–1024).

The melatonin receptor has some general structural features in common with amine and peptide receptors. For example, it contains a single cysteine residue in each of the first two extracellular loops that, based on mutagenesis studies of opsin and amine receptors (Dixon et al., *EMBO J.* (1987) 6:3269–3275; Karnic et al., *P.N.A.S. USA* (1988) 85:8459–8463), are believed to form a disulfide bridge which stabilizes receptor structure. Furthermore, proline residues are present in transmembrane domains IV, V and VI (FIG. 7 and FIG. 8) which have been suggested to introduce kinks in the alpha-helices that may be important in forming the ligand binding pocket (Findlay, J. and Eliopoulos, E., *Trends Pharmacol. Sci.* (1990) 11:492–499; Hibert, M. F. et al., *Mol. Pharmacol.* (1991) 40:8–15). The proline in the NPXXY (SEQ ID NO:7) motif that is found in transmembrane domain 7 of virtually all other G protein-coupled receptors is replaced by an alanine in the melatonin receptor.

The carboxyl tail of the melatonin receptor is 119 amino acid residues long and contains several consensus sites for protein kinase C phosphorylation which may be involved in receptor regulation (Sibley et al., *Cell* (1987) 48:913–922).

Binding Studies of the Recombinant Xenopus High-Affinity Melatonin Receptor.

To establish the binding characteristics of the encoded Xenopus receptor (SEQ ID NO:2), the cDNA in pcDNAI was transiently expressed in COS-7 cells. Three days after transfection, medium was removed, the culture dishes were washed with PBS, and the cells were harvested. The cells were then pelleted (2500 rpm; 10 min, 4° C.) and stored at −80° C. Whole cell binding studies were performed by thawing the cells and resuspending them in binding buffer (50 mM Tris-HCl, pH 7.4, with 5 mM $MgCl_2$) at a concentration of 456 μg protein/ml. The cell suspension was incubated with $^{125}$I-melatonin (90 pm) in a total reaction volume of 0.2 ml binding buffer in the presence or absence of a melatonin agonist or antagonist; the suspension was incubated in a shaker bath for 1.5 hr at 25° C. Protein determinations were performed using the Pierce BCA Protein Assay (The Pierce Chemical Co., Rockford, Ill.). Binding data were analyzed by computer using the LIGAND Program of Munson and Rodbard ((1980) supra). The results are shown in FIGS. 8 and 9.

To further establish the binding characteristics of the encoded Xenopus receptor (SEQ ID NO:2), the cDNA in pcDNAI was transiently expressed in COS-7 cells. Three days after transfection, saturation studies were performed using increasing concentrations of $^{125}$I-melatonin (5 to 1280 pM) (FIG. 10*a*). Scatchard analysis (FIG. 10*b*) revealed that transfected COS-7 cells bound $^{125}$I-melatonin with high affinity ($K_d$=63±3×10$^{-12}$; n=3 experiments). The $B_{max}$ value using the whole cell binding assay was 67±7 fmol/mg of protein. No specific binding of $^{125}$I-melatonin was found in mock-transfected COS-7 cells.

The pharmacological characteristics of specific $^{125}$I-melatonin binding in acutely transfected COS-7 cells was next examined (FIG. 11). The order of inhibition of specific $^{125}$I-melatonin binding of Xenopus recombinant melatonin receptor by six ligands was characteristic of a high-affinity melatonin receptor (Dubocovich, M. L. and Takahasi, J. (1987) supra; Rivkees et al. (1989) supra), with relative binding affinities having the order: 2-iodomelatonin>melatonin>6-chloromelatonin>6-hydroxymelatonin>n-acetyl-5-hydroxytryptamine>5-hydroxytryptamine. Thus, the isolated Xenopus laevis cDNA of the instant invention encodes a protein with the affinity and pharmacological properties expected of a high-affinity melatonin receptor.

The endogenous high-affinity melatonin receptor in Xenopus dermal melanophores is coupled to inhibition of adenylyl cyclase (Abe, K. et al. (1969) supra; White, B. H. et al. (1987) supra). To determine whether the receptor encoded by the recombinant cDNA (SEQ ID NO:1) of Xenopus was coupled to the adenylyl cyclase regulatory system, a clonal line of CHO (ATCC; Cat. No. CCL 61 cells) was stably transfected with the recombinant receptor cDNA and the melatonin-induced inhibition of forskolin-stimulated cAMP accumulation was determined.

Transformed CHO cells were plated on 35 mm culture dishes. After 48 hours, the cells were washed twice with Ham's F-12 (Life Technologies, Bethesda, Md.). Cells were then incubated in the presence or absence of melatonin analogs (diluted in F-12) for 10 min at 37° C. Following treatment, the medium was aspirated and 1 ml of 50 mM acetic acid was added to the culture dish. The cells were collected, transferred to an Eppendorf tube, boiled for 5 min, and centrifuged (13,750 rpm for 15 min). The supernatant was collected and assayed for cAMP. All determinations were performed in triplicate. Cyclic AMP levels were determined in duplicate by radioimmunoassay (New England Nuclear, Boston, Mass.).

Induction of cAMP concentration increase by 10 μM forskolin was inhibited by melatonin in a dose dependent manner (FIG. 12); the maximal inhibition of the mean forskolin-stimulated cAMP concentration was 68% at 1×10$^{-8}$M melatonin. An $IC_{50}$ value of approximately 8×10$^{-10}$M was determined by manual curve fitting of the data in FIG. 12. This value was very similar to the computer-generated $K_i$ value (1.3×10$^{-9}$M) determined for melatonin inhibition of specific $^{125}$I-melatonin binding shown in FIG. 11. Melatonin, alone, (1×10$^{-6}$M) was found not to alter basal cAMP levels in stably transfected CHO cells. Further, melatonin (1×10$^{-6}$M) did not inhibit the forskolin-stimulated increase in cAMP levels in CHO cells stably transfected with vector lacking the Xenopus cDNA. Thus, the recombinant melatonin receptor is negatively coupled to the cAMP regulatory system.

Expression of Xenopus Melatonin Receptor Transcripts

Northern blot analysis (see below) of Xenopus dermal melanophores revealed at least 3 hybridizing transcripts between 2.4 and 4.4 kb under conditions of high stringency (see below) (FIG. 13). The presence of multiple hybridizing bands may represent posttranscriptional modifications of the same gene, or the presence of transcripts from different, but structurally similar genes.

Northern analysis was performed using standard techniques (see, e.g., Ausubel et al., *Current Protocols in Molecular Biology*, John Wiley & Sons, New York, (1989)). Poly(A)$^+$RNA was subjected to electrophoresis through a 1% agarose-formaldehyde gel, blotted onto GeneScreen (New England Nuclear, Boston, Mass.), and hybridized with a fragment of the coding region of the receptor cDNA labeled with [α—$^{32}$P]dCTP (2000 Ci/mmol) by the method of random priming (Promega, Madison, Wis.). Hybridizing conditions were 50% formamide, 1M sodium chloride, 1% SDS, 10% dextran sulfate, and 100 μg/ml denatured salmon sperm DNA, at 42° C. overnight. The final washing of the blot was in 0.2X SSC/0.1% SDS at 65° C. for 40 min. Blots were exposed at −80° C. to X-ray film with an intensifying screen.

Isolation of Sheer High-Affinity Melatonin Receptor

To clone the high-affinity melatonin receptor from sheep using standard methods, fully degenerate primers were designed based on, for example, the peptide sequences 5' AIAINRY (SEQ ID NO:8) (residues 125–131) and 3' FAVCWAPL (SEQ ID NO:9) (residues 252–259) of the Xenopus sequence (SEQ ID NO:1) (FIG. 1). Using these populations of degenerate primers, RT PCR of sheep pars tuberalis mRNA amplified an approximately 400 bp cDNA fragment that was 65% identical at the amino acid level with the corresponding region of the Xenopus melatonin receptor.

To isolate a longer cDNA sequence, this fragment was labeled (e.g., with [$^{32}$P]dCTP by random priming) producing a probe, and hybridization (under high stringency conditions) was carried out on a sheep pars tuberalis cDNA library constructed in the ZAP II vector (Stratagene, La Jolla, Calif.) using standard hybridization techniques (see e.g., Ausubel et al., *Current Protocols in Molecular Biology*, supra). From 1×10$^6$ recombinants screened, two hybridizing clones were isolated and plaque purified using standard techniques. Both clones contained the entire 3' coding region, downstream from the predicted site of the third transmembrane domain. One clone extended 5' into the amino terminus region, upstream from the first transmembrane domain, but did not contain the entire 5' end of the coding region. A 160 bp fragment of the 5' end of this cDNA clone was labelled (e.g., radiolabelled) by standard techniques (see e.g., Ausubel et al., supra) and used to probe (e.g., by the standard techniques described, supra) a sheep genomic library (in EMBL-3, catalog number UL 1001d, Clontech, Palo Alto, Calif.). One clone was isolated and found to contain the remaining 5' sequence of the coding region using standard sequencing techniques. A 150 bp fragment of this genomic clone, containing a methionine with a consensus sequence for the initiation of translation was isolated and ligated using standard techniques (see e.g., Sambrook (1989), supra) into a vector (e.g., pcDNAI, InVitrogen, San Diego, Calif.) in frame with the corresponding downstream coding region of the cDNA. The ligated construct encodes a protein of 366 amino acids (SEQ ID NO:4) which binds [$^{125}$I]MEL with high affinity.

Binding Studies of the Recombinant Sheep High-Affinity Melatonin Receptor

The sheep high-affinity melatonin 1a receptor (SEQ ID NO:3) DNA cloned into pcDNAI was transiently expressed in COS-7 cells. For ligand binding studies, the sheep receptor cDNA (SEQ ID NO:3) in pcDNAI was introduced into COS-7 cells using the DEAE-dextran method (Cullen, B. R. Methods Enzymol. (1987) 152:684–704). Approximately two to three days after transfection, cell culture medium was removed, the cultures dishes were washed with PBS, and the cells were harvested. The cells were then pelleted (2500 rpm; 10 min, 4° C.) and stored at −80° C. Whole cell binding studies were performed by thawing the cells and resuspending them in binding buffer (50 mM Tris-HCl, pH 7.4, with 5 mM $MgCl_2$) at a concentration of 200–500 μg protein/ml. The cell suspension was incubated with $^{125}$I-Mel with or without drugs in a total reaction volume of 0.2 ml binding buffer; the suspension as incubated in a shaker bath for 1.5 hr at 25° C. All determinations were done in either duplicate or triplicate. Protein measurements were performed using the Pierce BCA Protein Assay. Binding data were analyzed by computer using the LIGAND Program of Munson and Rodbard (1980).

Scatchard analysis (performed as described above for the Xenopus clone) revealed that COS-7 cells transfected with the sheep Mel-1a receptor clone bound $^{125}$I-melatonin with high affinity ($K_d=3.6\pm0.1\times10^{-11}$M; mean ±SE, n=3 experiments). The $B_{max}$ value for the sheep receptor clone using the whole cell binding assay was greater than 112±5 fmol/mg of protein (FIG. 14a). No specific binding of $^{125}$I-melatonin was found in mock-transfected COS-7 cells.

The sheep Mel-1a receptor pharmacologic profile of relative binding affinities of melatonin derivatives was shown to be similar to Xenopus using the same assay techniques as described for Xenopus. Competitive binding of six ligands to sheep melatonin receptor expressed by acutely transfected COS-7 cells showed that the rank order of inhibition of specific $^{125}$I-Mel binding by the six ligands was 2-iodomelatonin>melatonin=6-chloromelatonin>6-hydroxymelatonin>N-acetyl-5-hydroxytryptamine>5-hydroxytryptamine (FIG. 14b).

The receptor encoded by the recombinant sheep melatonin 1a receptor was tested to determine whether it is coupled to inhibitory G protein ($G_i$), as has been shown with the endogenous receptor of several mammals, including sheep (Carlson, et al., (1989) supra; Morgan et al., (1990) supra). Clonal NIH 3T3 cells stably transfected with the sheep receptor CDNA (SEQ ID NO:3) subcloned into pcDNAI NEO (Invitrogen, San Diego, Calif.) and exhibiting high levels of melatonin receptor binding (>10 fmol/60 mm dish of cells using 100 pM $^{125}$I-Mel) were used. Transformed NIH 3T3 cells were plated on 35 mm dishes. After forty-eight hours, the cells were washed twice with DMEM, and then incubated with or without drugs (diluted in DMEM) for 10 min at 37° C. At the end of treatment, the medium was aspirated and 1 ml of 50 mM acetic acid was added. The cells were collected, transferred to an Eppendorf tube, boiled for 5 min, and centrifuged (13,750 rpm for 15 min). The supernatant was collected and assayed for cAMP. All determinations were done in triplicate. Cyclic AMP levels were determined in duplicate by radioimmunoassay by standard techniques.

Although melatonin did not alter basal cAMP levels in the stably transfected lines, it did cause a dose-dependent inhibition of the cAMP increase induced by 10 μM forskolin (FIG. 16a). The estimated $IC_{50}$ value for melatonin was $1\times10^{-10}$M, comparable to the $K_i$ value for melatonin inhibition of specific $^{125}$I-Mel binding ($2.4\times10^{-10}$M; see FIG. 14b). Importantly, melatonin (1 μM) did not inhibit forskolin-stimulated cAMP accumulation in NIH 3T3 cells stably transfected with the vector (pcDNAI NEO) lacking the sheep Mel-1a receptor cDNA.

Pertussis toxin pretreatment (PTX; 100 ng/ml) of receptor-transfected NIH 3T3 cells for 18 hours completely abolished the ability of 1 μM melatonin to inhibit the forskolin-stimulated increase in cAMP (FIG. 16b). Thus, like the endogenous high-affinity melatonin receptor of vertebrates (Carlson et al., (1989) supra; Morgan et al., (1990) supra; White et al., (1987) supra), the recombinant sheep Mel-1a receptor inhibits adenylyl cyclase through a pertussis-toxin sensitive mechanism.

Northern blot analysis of sheep PT revealed a major hybridizing transcript of greater than 9.5 kb and a minor transcript at 4.2 kb. No hybridizing signals were found in pars distalis (data not shown). Using antisense cRNA probes prepared using sheep melatonin 1a receptor cDNA, in situ hybridization of endogenous mRNA revealed a strong hybridization signal that was visible in film autoradiographs of the sheep PT (FIG. 17); no signal was detected in pars distalis. The mRNA distribution in PT was identical to that found for the receptor protein using $^{125}$I-Mel in vitro autoradiography. The SCN region of sheep was not examined for melatonin receptor mRNA because high-affinity melatonin receptors have not been identified in sheep SCN using $^{125}$I-Mel in in vitro autoradiography (Bittman, E. L. and Weaver, D. R., Biol. Reprod. (1990) 43:986–993).

Brain tissue of Siberian hamster and rat were examined to illustrate the distribution of melatonin receptor in brain of other species in which melatonin is known to have affects on reproductive and circadian rhythms (Bartness, T. J. et al., J. Pineal Res. (1993) 15:161–190; Margraf, R. R. and Lynch, G. R., Am. J. Physiol. (1993) 264:R615-R621; and Cassone, V. M., Trends Neurosci. (1990) 13:457–464). The major sites of specific $^{125}$I-Mel binding and receptor transcript hybridization in Siberian hamster brain are the PT, SCN and paraventricular nucleus of the thalamus as examined in adjacent sections by in vitro autoradiography (data not shown; see also Weaver, D. R. et al., J. Neurosci. (1989) 9:2582–2588). Thus, in this species, the distribution of melatonin 1a receptor mRNA and protein are identical and restricted to just a few sites in brain. The PT and SCN regions exhibited receptor transcript hybridization and $^{125}$I-Mel binding in adult and developing rats (data not shown). The distribution of melatonin 1a receptor mRNA was coincident to that of $^{125}$I-Mel binding throughout the SCN in both rat and hamster.

In all non-human mammals we have examined, including the sheep (FIG. 15), Siberian hamster, Syrian hamster, and rat, in situ hybridization studies have readily detected mRNA for the high-affinity melatonin 1a receptor in PT. The PT currently appears to be an important site through which melatonin mediates photoperiodic effects on reproductive function. The PT is the only site containing melatonin 1a receptors (as detected with $^{125}$I-Mel in vitro autoradiography) in all seasonally breeding mammals examined to date (Weaver et al., (1991) supra). The mechanisms by which the PT processes the daily melatonin signal and communicates that information to influence hypothalamic neurosecretion are unknown. High-affinity melatonin receptors have not been consistently detected in the human PT by $^{125}$I-Mel in vitro autoradiography, suggesting that neuroendocrine responses to melatonin in humans may occur through fundamentally different mechanisms than those that underlie the regulation of reproduction in seasonally breeding species (Weaver, D. R. et al., *J. Clin. Endocrinol. Metab.* (1993) 76:295–301.

Isolation of the Mouse High-Affinity Melatonin Receptor

Degenerate primers were designed using regions conserved amoung other mammalian Mel-1a receptor cDNAs such as those from sheep (see FIG. 2). Polymerase chain reaction (PCR) of mouse genomic DNA yielded a 466 bp fragment that was 94% identical at the amino acid level to the rat and Djungarian hamster Mel-1a receptor cDNAs. In situ hybridization of adult C57BL/6J mouse brain using the PCR-generated fragment produced a hybridization pattern consistent with that expected for the Mel-1a melatonin receptor. Hybridization signal was most intense in the hypophyseal pars tuberalis. Southern blot analysis of genomic DNA indicated a single-copy gene. RNA was isolated from a murine cell line (RT2-2) which expresses the Mel-1a receptor. Northern analysis of poly(A)$^+$RNA indicated a transcript length of approximately 1.9 kb. RT-PCR was used to generate the full length coding region (1059 bp) of the receptor, which showed 84% amino acid identity to the human Mel-1a receptor. RNase protection analysis, 5' and 3' RACE cloning, and screening of a BALB/c mouse EMBL3 SP6/T7 genomic library revealed that the receptor gene consists of 2 exons divided by a large (>8 kb) intron. The 3' untranslated region is 444 bp long, and includes the polyadenylation signal AUUAAA. RNase protection assays suggest that a major transcription start site is located approximately 100 bp upstream of the initiation codon. The nucleotide sequence and deduced amino acid sequence of the mouse Mel-1a receptor are shown in FIG. 3.

The recombinant mouse Mel-1a receptor expressed on COS-7 cells bound melatonin with high affinity comparable to the binding affinity of sheep and human Mel-1a receptors.

Isolation of a Fragment of the Human High-Affinity Mel-1a Receptor

To clone the human high-affinity melatonin receptor, the degenerate primers based on the peptide sequences 5' AIAINRY (SEQ ID NO:8) (residues 125–131 of the Xenopus deduced amino acid sequence (SEQ ID NO:2)) and 3' FAVCWAPL (SEQ ID NO:9) (residues 252–259 of the Xenopus deduced amino acid sequence (SEQ ID NO:2)) were used as described above. Human genomic DNA was amplified by standard PCR techniques using the degenerate primers and an approximately 400 bp fragment was isolated and sequenced by standard techniques. The deduced amino acid sequence of the 400 bp fragment was 65% identical at the amino acid level with the corresponding portion of the Xenopus high-affinity melatonin receptor. The 400 bp fragment was labelled (e.g., by random primer labelling; see e.g., Ausubel, supra) and used to screen a human genomic library (in vector EMBL-3, Clontech, Palo Alto, Calif., catalog number HL1067J) under high stringency conditions using standard hybridization techniques (see, e.g., Ausubel, supra). Several positively hybridizing clones were identified from 1×10$^6$ recombinant clones screened. The clones were plaque purified by standard techniques, digested with appropriate restriction enzymes and subcloned in to a convenient vector for sequencing (e.g., pBluescript®, Stratagene, La Jolla, Calif.). The human insert DNA (SEQ ID NO:5) of one clone was sequenced using standard techniques. Using the sheep (SEQ ID NO:3) and Xenopus (SEQ ID NO:1) nucleotide and deduced amino acid sequences (SEQ ID NO:4 and SEQ ID NO:2, respectively) for comparison (see FIG. 7 and FIG. 8), the human insert DNA was found to contain a portion of the coding region from the "GNXFVV (SEQ ID NO:10) motif" just downstream from the first transmembrane domain (see FIGS. 7 and 8) and extends through the 3' end of the coding region. The human DNA of the sequenced clone is approximately 82% identical to the sheep nucleotide sequence (SEQ IN NO:5) of the corresponding region. The sheep and human deduced amino acid sequences (SEQ IN NO:4 and SEQ IN NO:6, respectively) are approximately 80% identical in the corresponding regions. Thus the human DNA fragment (SEQ IN NO:5) isolated by the above techniques encodes a protein with strong identity to the corresponding portion of high-affinity melatonin receptor in another mammal, sheep.

The human genomic DNA contains an intron (>2.0 kb in length) upstream of the "GNXFVV motif" (SEQ IN NO:10). To obtain the 5' portion of the coding region of the human receptor, the 160 bp fragment of the coding region of the sheep receptor immediately upstream from this GNXFVV motif was used to reprobe the human genomic library at low stringency (for exemplary low stringency hybridization conditions see e.g., Ausubel et al. (1989), supra). One positively hybridizing clone was isolated and found by standard sequence analysis to contain the 5' end of the coding region. RT-PCR (see e.g., Reppert, et al., *Mol. Endocrinol.* (1991) 5:1037–1048) of mRNA from human hypothalamus using specific primers directed at the 5' and 3' ends of the putative coding region amplified the expected CDNA, containing the coding region of the human melatonin receptor. The cDNA was subcloned into pcDNAI for sequence analysis and transient expression of the receptor polypeptide.

The sequencing results show that cDNAs cloned in the instant invention encode a high-affinity melatonin receptor from Xenopus sheep, and human. Overall, the coding regions of the sheep receptor and complete human receptor are about 60% identical with that of the Xenopus melatonin receptor. Within the transmembrane domains, the identity is 77%. The most dissimilar regions between the mammalian and frog receptors was in the amino and carboxyl terminal regions. The amino terminus of the mammalian receptors contains two consensus sites for N-linked glycosylation, compared to one site in the frog receptor. Furthermore, the carboxyl tail of the sheep and human receptors is 65 amino acid residues shorter than the Xenopus receptor tail. The complete human high-affinity melatonin receptor DNA shows strong identity (approximately 82% at the nucleotide level and approximately 80% at the amino acid level) to the sheep high-affinity melatonin receptor with 87% amino acid identity when comparison is limited to the transmembrane domains. This high structural homology suggests that the human and sheep clones are species homologs of the same receptor.

Binding Studies of the Recombinant Human High-Affinity Mel-1a Receptor

The complete human high-affinity melatonin 1a receptor (SEQ ID NO:11) DNA cloned into pcDNAI was transiently expressed in COS-7 cells and binding studies were performed as described for the sheep receptor, supra. Scatchard analysis (performed as described above for the Xenopus and sheep clones) revealed that COS-7 cells transfected with the complete human receptor clone (containing DNA of SEQ ID NO:11) bound $^{125}$I-melatonin with high affinity ($K_d$=2.6 and 2.3×10$^{-11}$M; n=2 experiments). The $B_{max}$ value using the whole cell binding assay was 210 and 220 fmol/mg protein for the human receptor in two experiments (FIG. 15). No specific binding of $^{125}$I-melatonin was found in mock-transfected COS-7 cells. For the human clone, the rank order of inhibition was identical to that for sheep, except that 6-chloromelatonin was 10-fold less potent in inhibiting specific $^{125}$I-Mel binding ($k_i$ values listed in legend of FIG. 13b). Thus, the recombinant sheep and human receptors bind $^{125}$I-Mel with high affinity and exhibit the appropriate pharmacological characteristics of a high-affinity melatonin receptor (Dubocovich and Takahashi, (1987) supra; Morgan et al., (1989) *J. Endocrinol.* 1:1–4; Rivkees et al., *PNAS USA* (1989) 86:3883–3886; Vanecek, J., *J. Neurochem.* (1988) 51:1436–1440).

Isolation of a Human High-Affinity Mel-1b Receptor.

To clone melatonin receptor subtypes, PCR was used to amplify human genomic DNA with degenerate oligonucleotide primers based on conserved amino acid residues in the third and sixth transmembrane domains of the Xenopus melatonin receptor and mammalian Mel-1a melatonin receptors.

For PCR with degenerate primers, genomic DNA was subjected to 30 cycles of amplification with 200 nM (final concentration) each of two oligonucleotide primers. Each reaction cycle consisted of incubations at 94° C. for 45 sec, 45° C. for 2 min and 72° C. for 2 min, with AmpiTaq DNA polymerase (Perkin-Elmer Cetus). The amplified DNA was separated on an agarose gel. DNA bands were subcloned into pCRTMII using a TA Cloning Kit (Invitrogen), and recombinant clones were sequenced. For PCR with specific primers, either genomic DNA or first-strand cDNA reverse transcribed from RNA was subjected to 25 to 35 cycles of amplification using incubations at 94° C. for 45 sec, 60° C. for 45 sec and 72° C. for 2 or 3 min. The amplified DNA was separated on an agarose gel. DNA bands were subcloned into pcDNA3 (Invitrogen) for expression studies and sequence analysis, or subjected to Southern anlaysis for the comparative reverse transcription polymerase chain reaction (RT-PCR) assay (described herein below).

A human genomic library in EMBL-3 SP6/T7 (Clontech) was plated and transferred to Colony Plaque Screen filters (New England Nuclear). The filters were screened under conditions of either high or reduced stringency. High stringency consisted of overnight hybridization in 50% formamide, 1M sodium chloride, 1% SDS, 10% dextran sulfate, 100 μg/ml denatured salmon sperm at 42° C., with filters being washed in 2x SSC, 1% SDS at 65° C. for 1 hr. Reduced stringency consisted of the same hybridization solution at 42° C., except the formamide concentration was 25%; the filters were washed in 2x SSC, 1% SDS at 55° C. for 1 hr. Lambda phage that hybridized to the probe were plaque-purified.

A novel cDNA fragment (364 bp) was found by sequence analysis using standard techniques to be 60% identical at the amino acid level with either the human Mel-1a receptor or the Xenopus melatonin receptor. This PCR-fragment was labeled by a standard random priming technique and used to probe a human genomic library at high stringency. From 1×10$^6$ recombinants, seven positively hydridizing clones were identified and plaque purified. A 6 kb SacI-fragment of one of the genomic clones which hybridized to the PCR-generated cDNA fragment was subcloned and partially sequenced. This fragment contained the 3' end of the putative coding region and extended 5' to the GN motif in the first cytoplasmic loop, in which an apparent intron occurred; a consensus intron splice site occurs at an identical location in the human and sheep Mel-1a receptor genes (SEQ ID NO:11 and SEQ ID NO:3, respectively; Reppert, S. M., Weaver, D. R. & Ebisawa, T. (1994) Neuron 13: 1177–1185). To obtain the 5' portion of the coding region, a 160 bp fragment encoding the first transmembrane domain of the sheep Mella-melatonin receptor was used to reprobe the seven positive genomic clones at reduced stringency (Reppert, S. M. et al. (1994), supra). A 2.3 kb SacI-fragment of one of the genomic clones which hybridized to the sheep receptor fragmentd was subcloned and sequenced by standard techniques. This SacI-fragment contained the apparent 5' end of the coding region which includes an upstream, in-frame methionine with a consensus sequence for the initiation of translation (Kozak, M. (1987) Nudeic Acids Res. 15: 8125–8148) and a consensus site for N-linked glycosylation. RT-PCR of RNA from human brain using specific primers directed at the 5' and 3' ends of the putative coding region amplified the expected cDNA with the appropriate splicing predicted from genomic analysis, indicating that the putative receptor gene is transcribed. A PCR-generated construct of the coding region of human Mel-1b receptor was subcloned into pcDNA3 for expression studies and sequence analysis. The deduced amino acid sequence of human Mel-1b receptor was identical with the corresponding sequence of the SacI-genomic fragments.

Human melatonin-1b receptor encodes a protein of 362 amino acids (SEQ ID NO:16) with a predicted molecular mass of 40,188, not including posttranslational modifications (FIG. 6). Human Mel-1b is a member of a newly described melatonin receptor group that is distinct from the other receptor groups (e.g., biogenic amine, neuropeptide, and photopigment receptors) that comprise the prototypic G protein-coupled receptor family (Ebisawa, et al. (1994) Proc. Natl. Acad Sci. USA 91, 6133–6137; Reppert, S. M. et al. (1994), supra). Unique features of this group include a NRY motif just downstream from the third transmembrane domain (rather than DRY) and a NAXXY motif (SEQ ID NO:17) in transmembrane 7 (rather than NPXXY (SEQ ID NO:7)) (FIG. 18). In addition, the human Mel-1b receptor, the mammalian Mel-1a receptors, and the Xenopus melatonin receptor all have a CYICHS motif (SEQ ID NO:18) immediately downstream from NRY in the third cytoplasmic loop which is a consensus site for cytochrome c family heme binding (Mathews, F. S. (1985) Prog. Biophys. Mol. Biol. 45: 1–56). Pair-wise comparisons of the human Mel-1b receptor, the human Mel-1a receptor and the Xenopus melatonin receptor reveal approximately 60% amino acid identity for any pair of the three sequences (FIG. 18). Within the transmembrane domains the amino acid identity among any two of the three sequences is 73%. The most dissimilar regions among any two of the three receptors are in the amino- and carboxy-terminal regions and in the second and third cytoplasmic loops. Within the amino terminus there is one consensus site for N-linked glycosylation for the Xenopus melatonin receptor and the human Mel-1b receptor, while there are two sites in the amino terminus of the human Mel-1a receptor (FIG. 18, lower). The possibility of additional upstream translation start sites cannot be excluded.

Binding Studies of the Recombinant Human High-Affinity Mel-1b Receptor

Binding and pharmacological properties of the human Mel-1b receptor were examined by transiently expressing the receptor CDNA in COS-1 cells.

Expression studies were performed as follows. COS-1 and NIH 3T3 cells were grown as monolayers in Dulbecco's modified Eagle's medium (DMEM) supplemented with 10% fetal calf serum, penicillin (50 U/ml), and streptomycin (50 µg/ml), in 5% $CO_2$ at 37° C. For ligand binding studies, melatonin receptor cDNAs in pcDNA3 were introduced into COS-1 cells using the DEAE-dextran method (Cullen, B. (1987) Methods Enzymol. 152, 684–704). Three days after transfection, medium was removed, and the dishes were washed with PBS. The cells were harvested in Hank's balanced salt solution and centrifuged (1400×g; 10 min, 4° C.). The resultant pellets were stored at –80° C. Crude membrane homogenates were prepared by thawing the pellets on ice and resuspending them in TME buffer (pH 7.4) consisting of 50 mM Tris base, 12.5 mM MgCl2, 1 mM EDTA, and supplemented with 10 µg/ml aprotinin and leupeptin, and 100 µM phenylmethylsulfonylfluoride. The cells were then homogenized using a dounce homogenizer and centrifuged (45,000×g; 15 min at 4° C.). The resulting pellet was resuspended with a dounce homogenizer in. TME and frozen at 80° C. in aliquots.

Binding assays were performed in duplicate in a final volume of 200 µl, consisting of 20 µl radioligand, 20 µl TME containing either melatonin or displacer, and 160 µl membrane homogenates. Incubations were initiated by the addition of the membrane preparation and were conducted at 37° C. for 60 min. Nonspecific binding was defined by 10 µM melatonin. All determinations were done in either duplicate or triplicate.

Protein measurements were performed by the method of Bradford (Bradford, M. M. (1976) Anal. Biochem. 72, 248–254), using bovine serum albumin as the standard. Binding data were analyzed by computer using the LIGAND Program of Munson and Rodbard (Munson, P. J. and Rodbard, D. (1980) Anal. Biochem. 107, 220–239).

For comparison, binding and pharmacology of COS-1 cells transiently expressing the human Mel-1a receptor were assessed in parallel. Scatchard transformation of the saturation data showed that COS-1 cells transfected with either receptor bind $^{125}$I-Mel with high affinity. The $K_d$ of human Mel-1b receptor was $1.6\pm0.3\times10^{-1}$M (mean+SE; n=5 experiments) (FIG. 19). This value represents a 4-fold lower affinity than that of the human Mel-1a receptor ($K_d$= $6.5\pm0.6\times10^{-11}$M; n=3) found in parallel experiments. The $B_{max}$ values were 2.7±0.1 pmol/mg membrane protein for human Mel-1b receptor and 2.8±0.4 pmol/mg membrane protein for the human Mel-1a receptor. The pharmacological characteristics for inhibition of specific $^{125}$IMel binding in acutely transfected COS-1 cells were next examined for Mel-1b receptor and compared with those of the human Mel-1a receptor (FIG. 20; Table 1).

TABLE 1

Competition of various ligands for specific $^{125}$I-Mel binding in COS-1 cells transfected with either human Mel-1b or the Mel-1a receptor cDNA

| Compound | $K_i$ (nM) Mel-1b | $K_i$ (nM) Mel-1a | Ratio (Mel-1a/Mel-1b) |
|---|---|---|---|
| 2-iodomelatonin | 0.17 ± 0.02 | 0.09 ± 0.01 | 0.5 |
| 2-phenylmelatonin | 0.26 ± 0.06 | 0.21 ± 0.06 | 0.8 |
| S20098 | 0.23 ± 0.04 | 0.72 ± 0.11 | 3.1 |
| 6-chloromelatonin | 0.66 ± 0.04 | 6.78 ± 0.91 | 10.3 |
| melatonin | 1.11 ± 0.13 | 1.48 ± 0.21 | 1.3 |
| NAS | 595 ± 127 | 986 ± 137 | 1.6 |
| 5-HT | >10,000 | >10,000 | — |
| prazosin | >10,000 | >10,000 | — |

$K_i$ values are mean ± SE of 3–5 experiments for each drug. NAS: N-acetyl-5-hydroxytryptamine. 5-HT: 5-hydroxytryptamme. S20098, a melatonin analog was obtained from Bristol-Myers Squibb, Princeton, NJ.

For human Mel-1b, the rank order of inhibition of specific $^{125}$I-Mel binding by six ligands was 2-iodomelatonin>2-phenylmelatonin>S-20098>6-chloromelatonin>melatonin>N-acetyl-5-hydroxytryptamine (FIG. 20a; Table 1). Micromolar concentrations of prazosin or 5-hydroxytryptamine did not inhibit specific $^{125}$I-Mel binding. The rank order of inhibition of specific $^{125}$I-Mel binding for human Mel-1b receptor was very similar to that found in parallel experiments for the human Mel-1a melatonin receptor, except that 6chloromelatonin was 10-fold more potent in inhibiting specific $^{125}$I-Mel binding in cells expressing human Mel-1b receptor (FIG. 20b; Table 1). Thus, human Mel-1b receptor cDNA encodes a protein with $^{125}$I-Mel binding characteristics that are quite similar to those of the Mel-1a melatonin receptor.

Melatonin Inhibits cAMP Accumulation in Mel-1b-expressing Cells.

The recombinant Mel-1b receptor is coupled to inhibition of adenylyl cyclase as is the Mel-1a melatonin receptor (Reppert, S. M. et al. (1994), supra).

For these studies, we used clonal lines of NIH 3T3 cells stably transfected with the receptor cDNA in pcDNA3. COS-1 and NIH 3T3 cells were grown as monolayers in Dulbecco's modified Eagle's medium (DMEM) supplemented with 10% fetal calf serum, penicillin (50 U/ml), and streptomycin (50 µg/ml), in 5% $CO_2$ at 37° C.

For ligand binding studies, melatonin receptor cDNAs in pcDNA3 were introduced into COS-1 cells using the DEAE-dextran method (Cullen, B. (1987) supra). Three days after transfection, medium was removed, and the dishes were washed with PBS. The cells were harvested in Hank's balanced salt solution and centAfuged (1400×g; 10 min, 4° C.). The resultant pellets were stored at –80° C. Crude membrane homogenates were prepared by thawing the pellets on ice and resuspending them in TME buffer (pH 7.4) consisting of 50 mM Tris base, 12.5 mM MgCl2, 1 mM EDTA, and supplemented with 10 µg/ml aprotinin and leupeptin, and 100 µM phenylmethylsulfonylfluoride. The cells were then homogenized using a dounce homogenizer and centrifuged (45,000×g; 15 min at 4° C.). The resulting pellet was resuspended with a dounce homogenizer in TME and frozen at –80° C. in aliquots. Binding assays were performed in duplicate in a final volume of 200 µl, consisting of 20 µl radioligand, 20 µl TME containing either melatonin or displacer, and 160 µl membrane homogenates. Incubations were initiated by the addition of the membrane preparation and were conducted at 37° C. for 60 min. Nonspecific binding was defined by 10 µM melatonin. All determinations were done in either duplicate or triplicate.

Protein measurements were performed by the method of Bradford (Bradford, M. M. (1976) supra), using bovine serum albumin as the standard. Binding data were analyzed by computer using the LIGAND Program of Munson and Rodbard (Munson, P. J. & Rodbard, D. (1980) supra). For cAMP studies, the receptor cDNA in pcDNA3 was introduced into NIH 3T3 cells using Lipofectamine (GIBCO/BRL). Transformed NIH 3T3 cells resistant to Geneticin, G418 (at 1.0 mg/ml; Gibco/BRL) were isolated and single colonies expressing melatonin receptor binding (>200 fmol/mg total cellular protein) were isolated.

Transformed NIH 3T3 cells were plated in triplicate on 35 mm dishes. Forty-eight hours later, the cells were washed (2X) with DMEM and preincubated with 250 uM 3-isobutyl-1-methylxanthine (IBMX) in DMEM for 10 min at 37° C. Cells were then incubated with or without drugs in DMEM with 250 AM IBMX for 10 min at 37° C. At the end of treatment, the medium was aspirated and 0.5 ml of 50 mM acetic acid was added. The cells were collected, transferred to an Eppendorf tube, boiled for 5 min, and centrifuged (13,750 rpm for 15 min). The supernatant was collected and assayed for cAMP. All determinations were done in triplicate. Cyclic AMP levels were determined in duplicate by radioimmunoassay (New England Nuclear). $^{125}$I-Mel was purchased from New England Nuclear. All drugs used in competition studies were purchased from Sigma, Research Biochemicals or were synthesized by standard methods. All other chemicals were purchased from Sigma.

Results of these studies showed that melatonin (1 $\mu$M) did not increase basal cAMP levels in stably transfected NIH 3T3 cells. Melatonin did cause a dose-dependent inhibition of the increase in cAMP accumulation induced by 10 $\mu$M forskolin (FIG. 21); the maximal inhibition of the mean forskolin stimulated cAMP value was at $10^{-8}$M melatonin. The estimated IC$_{50}$ value of this response (ca. $1\times10^{-9}$M) was very similar to the computer generated K$_i$ value ($1.11\pm0.13\times10^{-9}$M) determined for melatonin inhibition of specific $^{125}$I-Mel binding (FIG. 20; Table 1). Thus, the recombinant melatonin-1b receptor is negatively coupled to the cAMP regulatory system.

Characteristics of the Human High Affinity Mel-1b Receptor Gene and its Expression Restriction endonuclease mapping and PCR analysis of genomic clones showed that the portion of the gene that encodes the coding region of human Mel-1b receptor is comprised of two exons, separated by an intron that is approximately 9.0 kb in length. Southern analysis of human genomic DNA digested with several different restriction endonucleases was performed using a PCR-fragment of the second exon of human Mel-1b DNA as a hybridization probe. Under high stringency conditions, a pattern of single bands was observed, suggesting that human Mel-1b receptor is encoded by a single copy gene.

To localize the gene for human Mel-1b, an intronic PCR assay was developed that would amplify only the human Mel-1b receptor gene. A panel of 43 human-rodent somatic cell hybrids that contained defined overlapping subsets of human chromosomes was screened (Geissler, E. N., Liao, M., Brook, J. D., Martin, F. H., Zsebo, K. M., Housman, D. E. & Galli, S. J. (1991) Somatic Cell Genet. 17, 207–214; Pelletier, J., Brook, D. J. & Housman, D. E. (1991) Genomics 10, 1079–1082; NIGMS Mapping Panel #2, Coriell Institute, Camden, N.J.). Using primer 5'-CTGTGCCTCTAAGAGCCACTTGGTTTC-3' (SEQ ID NO:19) and primer 5'TATTGAAGACAGAGCCGAT-GACGCTCA3' (SEQ ID NO:29), PCR amplified a single band only in those cell lines containing human chromosome 11. The Mel-1b receptor gene was further localized to band 11q21-22 by PCR screening of a panel of somatic cell hybrids containing various deletion fragments of human chromosome 11 (Glaser, T., Housman, D., Lewis, W. H., Gerhard, D. & Jones, C. (1989) Somat. Cell. Mol. Genet. 15, 477–501; FIG. 23). The gene encoding human Mel-1b receptor has been given the designation MTNR1 B.

To assess the tissue distribution of human Mel-1b mRNA, comparative RT-PCR analysis was performed using a modification of a previously described procedure (Kelly, M. R., Jurgens, J. K., Tentler, J., Emanuele, N. V., Blutt, S. E., Emanuele, M. A. (1993) Alcohol 10: 185–189). Poly(A)$^+$ RNA was purchased from Clontech and 2 $\mu$g from each tissue was primed with random hexamers and reverse transcribed as previously described (Reppert, S. M., Weaver D. R., Stehle, J. H. & Rivkees, S. A. (1991) Mol. Endocrinol. 5:1037–1048). The cDNA was subjected to 25 cycles of amplification with 200 nm each of two specific primers.

The Mel-1b and Mel-1a receptor primers were designed so that they would amplify cDNA across the intron splice sites in the first cytoplasmic loop. Since the introns for both the Mel-1b and Mel-1a receptor genes are large (>8 kb), amplification of the appropriate sized cDNA fragments would eliminate the possibility of amplification of genomic DNA. The human Mel-1b receptor primers were 5'-TCCTGGTGATCCTCTCCGTGCTCA-3' (SEQ ID NO:20) and 5'-AGCCAGATGAGGCAGATGTGCAGA-3' (SEQ ID NO:21), and amplified a band of 321 bp. The Mel-1a receptor primers were 5'-TCCTGGTCATCCTGTCGGTGTATC-3' (SEQ ID NO:22) and 5'-CTGCTGTACAGTTTGTCGTACTTG-3' (SEQ ID NO:23), and amplified a band of 285 bp. Histone-H3.3 served as a control to verify the amount of template for each sample. The histone H3.3 primers were 5'-GCAAGAGTGCGCCCTCTACTG-3' (SEQ ID NO:24) and 5'-GGCCTCACTTGCCTCCTGCAA-3' (SEQ ID NO:25), and amplified a band of 217 bp.

After PCR, the reaction products were subjected to electrophoresis through a 1.5% agarose gel and blotted onto GeneScreen (New England Nuclear). To increase the specificity of the assay, blots were hybridized with 25-mer oligonucleotides, labeled with [$\gamma$-32P]ATP by T4 polynucleotide kinase. For each primer pair, the oligonucleotide probes were specific for a sequence of the amplified fragment between the primers. Oligonucleotide sequences were 5'-CTAATCCTCGTGGCCAATCTTCTATG-3' (SEQ ID NO:26) for human Mel-1b receptor; 5'-TTGGTGCTGATGTCGATATTTAACA-3' (SEQ ID NO:27) for the human Mel-1a receptor; and 5'-CACTGAACTTCTGATTCGCAAACTT-3' (SEQ ID NO:28) for histoneH3.3. Hybridizing conditions were 45° C. overnight in 0.5M NaPO$_4$ (pH 7.2), 7% SDS, 1% BSA and 1 mM EDTA. The blots were washed twice in 0.2M NaPO$_4$, 1% SDS and 1 mM EDTA at 45° C. for 30 min.

A 364 bp fragment of the rat homolog of the human Mel-1b receptor cDNA was cloned by RT-PCR from rat brain RNA; the rat cDNA fragment was 81% identical at the amino acid level with human Mel-1b receptor. The rat fragment was used to probe a Northern blot containing 5 $\mu$g poly(A)$^+$RNA from each of 20 different rat tissues. No positive hybridization signals were found. Furthermore, In situ hybridization using an antisense cRNA probe to the rat fragment did not reveal a hybridization signal in PT or SCN, sites which gave a positive hybridization signal in the same in situ run using an antisense cRNA probe to the Mel-1a receptor (Reppert, S. M., Weaver, D. R. & Ebisawa, T. (1994) Neuron 13, 1177–1185).

Because of the apparent low level of receptor transcripts, a comparative RT-PCR assay was used to examine the expression of human Mel-1b and Mel-1a receptor genes in 6 human tissues (FIG. 22). Human Mel-1b receptor was expressed in retina, with much lower expression in whole brain and hippocampus. The human Mel-1a receptor was clearly expressed in whole brain, with just detectable expression in retina and hippocampus. Neither Mel-1b nor Mel-1a receptor mRNA was detected in pituitary, liver of spleen. To ensure consistency in the amount of RNA reverse transcribed and the efficiency of the reverse transcription reactions among the tissues examined, the histone H3.3 cDNA was amplified from each tissue examined; very comparable amplifications occurred among the six tissues (FIG. 22).

Relative Characteristics of the Human High Affinity Mel-1a and Mel-1b Receptors

One feature that distinguishes the Mel1b-receptor from the Mel-1a receptor is its tissue distribution. The substantially greater expression of the Mel-1b receptor in retina suggests that melatonin may exert its effects on mammalian retinal physiology through this receptor. Melatonin inhibits the $Ca^{+2}$-dependent release of dopamine in rabbit retina through activation of receptors with pharmacologic specificity comparable with that reported here for the Mel-1b receptor (Dubocovich, M. L. & Takahashi, J. (1987) Proc. Natl. Acad. Sci. USA 84, 3916–3920; Dubocovich, M. L. (1983) Nature 306, 782–4). Melatonin appears to act in the retina to affect several light-dependent functions, including photopigment disc shedding and phagocytosis (Besharse, J. C. & Dunis, D. A. (1983) Science 219:1341–1343; Cahill, G. M., Grace, M. S. & Besharse, J. C. (1991) Cell. Mol. Neurobiol. 11:529–560).

The discovery of the Mel-1b receptor which has similar binding and functional characteristics to those of the Mel-1a receptor make it conceivable that the Mel-1b receptor also participates in the circadian and/or reproductive actions of melatonin. Even though Mel-1b receptor mRNA is not detectable by in situ hybridization in rat SCN or PT, it may be present and functional in these or other neural sites at levels not detectable using standard detection methods.

A second distinguishing feature of the Mel-1b receptor is its chromosome location. The Mel-1b melatonin receptor maps to human chromosome 11q21-22, a region syntenic to mouse chromosome 9 in the region of the $D_2$-dopamine receptor (Drd2) and thymus cell antigen 1 (Thy1) loci (Goldsborough et al. (1993) Nucl. Acids Res. 21:127–132; Seldin, M. F., Saunders, A. M., Rochelle, J. M. and Howard, T. A. (1991) Genomics 9:678–685). This contrasts with the Mel-1a receptor which maps to human chromosome 4q35.1 and mouse chromosome 8. Thus, these two structurally and functionally related melatonin receptors did not merely evolve by simple tandem duplication of an ancestral gene, but suggests that other mechanisms, such as chromosomal rearrangement and duplication, were involved.

The discovery of a new member of the G protein-coupled, melatonin receptor family shows that at least two distinct genes have evolved to subserve melatonin's functions. The development of a method of identifying pharmacological agents which selectively affect Mel-1a and Mel-1b receptor function is an important therapeutic application made available by the disclosed invention.

Relative Characteristics of the Xenopus and Mammalian Melatonin-1a High-Affinity Receptors Acute transfection of COS-7 cells with the Xenopus melatonin receptor and the sheep Mel-1a receptor clones results in transient expression of receptors that bind $^{125}$I-melatonin with high affinity (FIG. 9 and FIG. 12b). Additionally, specific $^{125}$I-melatonin binding to Xenopus receptor transiently expressed in cells is inhibited by six ligands in a rank order that is identical to that reported for the endogenous Mel-1a receptor in reptiles, birds, and mammals (FIG. 9) (Dubocovich et al. (1987), supra; Rivkees et al. (1989), supra; Morgan, P. J. et al. (1989) supra). The ability of the recombinant Xenopus high-affinity melatonin receptor to inhibit the forskolin-stimulated increase in cAMP accumulation in stably transfected CHO cells is consistent with studies of the endogenous receptor which show that a major signal transduction pathway for the high-affinity Mel -1a receptor is inhibition of adenylyl cyclase (Abe, K. et al. (1969), supra; White et al. (1987), supra). Finally, Xenopus melatonin receptor mRNA is moderately expressed in the cells whose RNA was used to generate the cDNA library. Thus, the cloned receptor likely mediates the potent effects of melatonin on pigment aggregation in frog melanophores. Structurally, the protein encoded by the melatonin receptor cDNA defines a new receptor group within the large superfamily of G protein-coupled receptors.

Previous studies using quantitative $^{125}$I-Mel autoradiography in the human SCN have generally shown high affinity for melatonin and 6-chloromelatonin and very low affinity for serotonin (Reppert et al., (1988) supra), all consistent with the pharmacological characteristics of the recombinant human receptor (FIG. 15). The pharmacological characteristics of the recombinant sheep Mel-1a receptor are virtually identical to those of the endogenous melatonin 1a receptor in sheep PT (Morgan et al., J. Endocrinol. (1989) 1:1–4). The difference between the sheep and human Mel-1a receptors in their affinities for 6-chloromelatonin is reproducible and equally apparent when the sheep and human Mel-1a receptors are examined in the same assay run.

Polypeptide Expression

Polypeptides according to the invention may be produced by transformation of a suitable host cell with all or part of a high-affinity melatonin receptor-encoding cDNA fragment (e.g., the cDNAs described above) in a suitable expression vehicle, and expression of the receptor.

Those skilled in the field of molecular biology will understand that any of a wide variety of expression systems may be used to provide the recombinant receptor protein. The precise host cell used is not critical to the invention. The receptor may be produced in a prokaryotic host (e.g., E. coli) or in a eukaryotic host (e.g., Saccharomyces cerevisiae or mammalian cells, e.g., COS-6M, COS-7 NIH/3T3, or Chinese Hamster Ovary cells). Such cells are available from a wide range of sources (e.g., the American Type Culture Collection, Rockville, Md.). The method of transfection and the choice of expression vehicle will depend on the host system selected. Transformation and mammalian cell transfection methods are described, e.g., in Ausubel et al. (Current Protocols in Molecular Biology, John Wiley & Sons, New York, (1989)); expression vehicles may be chosen from those provided, e.g., in Cloning Vectors: A Laboratory Manual (Pouwels, P. H. et al., (1985), Supp. 1987).

One particularly preferred expression system is the Chinese hamster ovary (CHO) cell (ATCC Accession No. CCL 61) transfected with a pcDNAI/NEO expression vector (InVitrogen, San Diego, Calif.). pcDNAI/NEO provides an SV40 origin of replication which allows replication in mammalian systems, a selectable neomycin gene, and SV40 splicing and polyadenylation sites. DNA encoding the human, sheep, or Xenopus high-affinity melatonin receptor or an appropriate receptor fragment or analog (as described above) would be inserted into the pcDNAI/NEO vector in an orientation designed to allow expression. Other preferable host cells which may be used in conjunction with the pcDNAI/NEO expression vehicle include NIH/3T3 cells (ATCC Accession No. 1658). The expression may be used in a screening method of the invention (described below) or, if desired, the recombinant receptor protein may be isolated as described below.

Alternatively, the high-affinity melatonin receptor (or receptor fragment or analog) is expressed by a stably-transfected mammalian cell line.

A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the receptor (or receptor fragment or analog) is cloned into an expression vector which includes the dihydrofolate reductase (DHFR) gene. Integration of the plasmid and, therefore, the high-affinity melatonin receptor-encoding gene into the host cell chromosome is selected for by inclusion of 0.01–300 µM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

One particularly preferred stable expression system is a CHO cell (ATCC) stably transfected with a pcDNAI/NEO (InVitrogen, San Diego, Calif.) expression vector.

Expression of the recombinant receptor (e.g., produced by any of the expression systems described herein) may be assayed by immunological procedures, such as Western blot or immunoprecipitation analysis of recombinant cell extracts, or by immunofluorescence of intact recombinant cells (using, e.g, the methods described in Ausubel et al., supra). Recombinant receptor protein is detected using an antibody directed to the receptor. Described below are methods for producing high-affinity melatonin receptor antibodies using, as an immunogen, the intact receptor or a peptide which includes a suitable high-affinity melatonin receptor epitope. To detect expression of a high-affinity melatonin receptor fragment or analog, the antibody is preferably produced using, as an immunogen, an epitope included in the fragment or analog.

Once the recombinant high-affinity melatonin receptor protein (or fragment or analog, thereof) is expressed, it is isolated, e.g., using immunoaffinity chromatography. In one example, an anti-high-affinity melatonin receptor antibody may be attached to a column and used to isolate intact receptor or receptor fragments or analogs. Lysis and fractionation of receptor-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, (1980)).

Receptors of the invention, particularly short receptor fragments, can also be produced by chemical synthesis (e.g., by the methods described in *Solid Phase Peptide Synthesis,* (1984) 2nd ed., The Pierce Chemical Co., Rockford, Ill.).

Assays for High-Affinity Melatonin Receptor Function

Useful receptor fragments or analogs in the invention are those which interact with melatonin. Such an interaction may be detected by an in vitro functional assay (e.g., the cAMP accumulation assay described herein). This assay includes, as components, forskolin for induced cAMP accumulations, melatonin, and a recombinant high-affinity melatonin receptor (or a suitable fragment or analog) configured to permit melatonin binding (e.g., those polypeptides described herein). Melatonin and forskolin may be obtained from Sigma (St. Louis, Mo.) or similar supplier.

Preferably, the high-affinity melatonin receptor component is produced by a cell that naturally presents substantially no receptor on its surface, e.g., by engineering such a cell to contain nucleic acid encoding the receptor component in an appropriate expression system. Suitable cells are, e.g., those discussed above with respect to the production of recombinant receptor, such as CHO cells or COS-7 cells.

Screening For High-Affinity Melatonin Receptor Antagonists and Agonists

As discussed above, one aspect of the invention features screening for compounds that antagonize the interaction between melatonin and the high-affinity melatonin receptor, thereby preventing or reducing the cascade of events that are mediated by that interaction. The elements of the screen are forskolin to induce intracellular accumulation of cAMP, melatonin, and recombinant high-affinity receptor (or a suitable receptor fragment or analog, as outlined above) configured to permit detection of melatonin function. As described above, melatonin and forskolin may be purchased from Sigma, and a full-length sheep Mel-1a receptor or Xenopus high-affinity elatonin receptor, or a human high-affinity melatonin 1a or 1b receptor (or a melatonin-binding fragment or analog of the Xenopus, sheep or human receptors) may be produced as described herein. Preferably, such a screening assay is carried out using cell lines stably transfected with the high-affinity melatonin receptor. Most preferably, the untransfected cell line presents substantially no receptor on its cell surface.

Activation of the heterologous high-affinity melatonin receptor with melatonin or an agonist (see above) leads to reduction of intracellular cAMP concentration, providing a convenient means for measuring melatonin or agonist activity. Such an agonist may be expected to be a useful therapeutic agent for circadian rhythm disorders such as jet lag, day/night cycle disorders in humans or mating cycle alterations in animals such as sheep. Appropriate candidate agonists include melatonin analogs or other agents which mimic the action of melatonin.

Inclusion of potential antagonists in the screening assay along with melatonin allows for the screening and identification of authentic receptor antagonists as those which decrease melatonin-mediated intracellular cAMP reduction. Receptor bearing cells incubated with forskolin (for initial induction cAMP concentration) or melatonin (alone, i.e., in the absence of inhibitor) are used as a "control" against which antagonist assays are measured.

Appropriate candidate antagonists include high-affinity melatonin receptor fragments, particularly, fragments of the protein predicted to be extracellular (see FIG. 7) and therefore likely to bind melatonin; such fragments would preferably including five or more amino acids. Other candidate antagonists include melatonin analogs as well as other peptide and non-peptide compounds and anti-high-affinity melatonin receptor antibodies.

Another aspect of the invention features screening for compounds that act as high-affinity melatonin receptor agonists; such compounds are identified as those which bind a high-affinity melatonin receptor and mimic the cascade of events that are normally mediated by that interaction. This screen requires recombinant cells expressing recombinant high-affinity melatonin receptor (or a suitable receptor fragment or analog, as outlined herein) configured to permit detection of high-affinity melatonin receptor function. In one example, a candidate agonist is added to CHO cells stably expressing recombinant receptor and intracellular cAMP levels are measured (as described above). An agonist useful in the invention is one which imitates the normal melatonin-mediated signal transduction pathway leading, e.g., to an decrease in intracellular cAMP concentration.

Appropriate candidate agonists include melatonin analogs or other chemical agents capable of mimicking the action of melatonin.

Preparation of a Transgenic Animal Containing Recombinant Melatonin-1a and/or Melatonin-1b Genes There are several means by which transgenic animals can be made. A transgenic animal (such as a mammal) may be constructed by one of several techniques, including targeted insertion of an exogenous melatonin receptor gene into the endogenous gene of the animal, or other methods well known to those skilled in the art.

A transgenic mammal whose germ cells and somatic cells contain an exogenous melatonin-1a or melatonin-1b receptor gene is produced by methods known in the art. See, for example, U.S. Pat. No. 4,736,866 describing production of a transgenic mammal, herein incorporated by reference. Generally, the DNA sequence encoding an exogenous melatonin-1a or -1b receptor gene is introduced into the animal, or an ancestor of the animal, at an embryonic stage (preferably the one-cell, or fertilized oocyte, stage, and generally not later than about the 8-cell stage). There are several methods known to the art of introducing a foreign gene into an animal embryo to achieve stable expression of the foreign gene. One method is to transfect the embryo with the gene as it occurs naturally, and select transgenic animals in which the foreign gene has integrated into the genome at a locus which results in its expression. Other methods involve modifying the foreign gene or its control sequences prior to introduction into the embryo. For example, the melatonin-1a or -1b receptor gene may be modified with an enhanced, inducible, or tissue-specific promoter.

Tissues of transgenic mammals are analyzed for the presence of exogenous melatonin-1a or -1b receptor, either by directly analyzing mRNA, or by assaying the tissue for exogenous melatonin-1a or -1b receptor.

Using the Transgenic Mammal to Determine Melatonin Agonist- or Antagonist-Related Effects The animals described above can be used to determine whether candidate compounds are melatonin antagonists or agonists for the Mel-1a or Mel-1b receptors.

Assessing Melatonin Agonists or Antagonists in vivo

One aspect of the invention features screening for compounds that agonize or antagonize melatonin activity in vivo. The elements of the screen are a Mel-1a or Mel-1b transgenic mammal and a potential melatonin agonist or antagonist in a suitable formulation for administration to the mammal. Detection of a change in the phenotype of interest (e.g., sleep/wake cycle or reproductive cycle) relative to a control transgenic mammal to which no agonist or antagonist has been administered indicates a potentially useful candidate compound.

Anti-High-Affinity Melatonin Receptor Antibodies

High-affinity melatonin receptor (or immunogenic receptor fragments or analogs) may be used to raise antibodies useful in the invention. As described above, receptor fragments preferred for the production of antibodies are those fragments deduced or shown experimentally to be extracellular.

Antibodies directed to high-affinity melatonin receptor peptides are produced as follows. Peptides corresponding to all or part of the putative extracellular loops or the extracellular N-terminal domain are produced using a peptide synthesizer, by standard techniques. The peptides are coupled to KLH with m-maleimide benzoic acid N-hydroxysuccinimide ester. The KLH-peptide is mixed with Freund's adjuvant and injected into animals, e.g. guinea pigs or goats, to produce polyclonal antibodies. Monoclonal antibodies may be prepared using the high-affinity melatonin polypeptides described above and standard hybridoma technology (see, e.g., Kohler et al., *Nature* (1975) 256:495, 1975; Kohler et al., *Eur. J. Immunol.* (1976) 6:292; Kohler et al., *Eur. J. Immunol.* (1976) 6:511; Hammerling et al., in *Monoclonal Antibodies and T Cell Hybridomas*, Elsevier, N.Y., (1981); and Ausubel et al., supra). Antibodies are purified by peptide antigen affinity chromatography.

Once produced, antibodies are tested for specific high-affinity melatonin receptor recognition by Western blot or immunoprecipitation analysis (by the methods described in Ausubel et al., supra).

Antibodies which specifically recognize the high-affinity melatonin receptor are considered to be likely candidates for useful antagonists; such candidates are further tested for their ability to specifically interfere with the interaction between melatonin and its receptor (using the functional antagonist assays described herein). Antibodies which antagonize melatonin: high-affinity melatonin receptor binding or high-affinity melatonin receptor function are considered to be useful as antagonists in the invention.

Therapy

Particularly suitable therapeutics for the treatment of circadian rhythm disorders in humans as well as for regulating changes in the reproductive cycle of seasonally breeding animals are the agonists and antagonists described above formulated in an appropriate buffer such as physiological saline. Where it is particularly desirable to mimic a receptor fragment conformation at the membrane interface, the fragment may include a sufficient number of adjacent transmembrane residues. In this case, the fragment may be associated with an appropriate lipid fraction (e.g., in lipid vesicles or attached to fragments obtained by disrupting a cell membrane). Alternatively, anti-high-affinity melatonin receptor antibodies produced as described above may be used as a therapeutic. Again, the antibodies would be administered in a pharmaceutically-acceptable buffer (e.g., physiological saline). If appropriate, the antibody preparation may be combined with a suitable adjuvant.

The therapeutic preparation is administered in accordance with the condition to be treated. Ordinarily, it will be administered intravenously, at a dosage, of a duration, and with the appropriate timing to elicit the desired response. Appropriate timing refers to the time in the natural circadian rhythm at which administration of therapeutic preparation elicits the desired response. Alternatively, it may be convenient to administer the therapeutic orally, nasally, or topically, e.g., as a liquid or a spray. Again, the dosages are as described above. Treatment may be repeated as necessary for alleviation of disease symptoms.

High-affinity melatonin receptor agonists can be used to reentrain the endogenous melatonin rhythm of humans; alleviate jet lag symptoms in humans; phase shift the sleep/ wake cycle of some blind people, reinforce entrainment of endogenous melatonin rhythm using low intensity light/dark cycle; control ovulation in humans; and alter reproductive cycles in seasonally breeding animals. Antagonists may be useful in controlling the initiation or timing of puberty in humans.

The methods of the invention may be used to screen therapeutic receptor agonists and antagonists for their effectiveness in reducing intracellular cAMP production in vitro; in altering circadian rythmn; or in altering reproductive cycles by the assays described above. Where a non-human mammal is treated or where a therapeutic for a non-human animal is screened, the high-affinity melatonin receptor or receptor fragment or analog or the antibody employed is preferably specific for that species.

Other Embodiments

Polypeptides according to the invention include any high-affinity melatonin receptors (as described herein). Such receptors may be derived from any source, but are preferably derived from a vertebrate animal, e.g., a human, a sheep, or a frog. These polypeptides are used, e.g., to screen for antagonists which disrupt, or agonists which mimic, a melatonin:receptor interaction (see above).

Polypeptides of the invention also include any analog or fragment of a high-affinity melatonin receptor capable of interacting with melatonin (e.g., those derived from the high-affinity melatonin receptor extracellular domains). Such analogs and fragments may also be used to screen for high-affinity melatonin receptor antagonists or agonists. In addition, that subset of receptor fragments or analogs which bind melatonin and are, preferably, soluble (or insoluble and formulated in a lipid vesicle) may be used as antagonists to reduce the amplitude of the endogenous melatonin cycle possibly providing for the induction of puberty in humans. The efficacy of a receptor analog or fragment is dependent upon its ability to interact with melatonin; such an interaction may be readily assayed using high-affinity melatonin receptor functional assays (e.g., those described herein).

Specific receptor analogs of interest include full-length or partial receptor proteins including an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy the receptors' ability to signal melatonin-mediated reduction in intracellular cAMP concentration (e.g., as assayed above).

Specific receptor fragments of interest include any portion of the high-affinity melatonin receptor which is capable of interacting with melatonin, for example, all or part of the extracellular domains (described above). Such fragments may be useful as antagonists (as described above), and are also useful as immunogens for producing antibodies which neutralize the activity of the high-affinity melatonin receptor in vivo (e.g., by interfering with the interaction between the receptor and melatonin; see below).

Extracellular regions of novel high-affinity melatonin receptors may be identified by comparison with related proteins of similar structure (e.g., other members of the G-protein-coupled receptor superfamily); useful regions are those exhibiting homology to the extracellular domains of well-characterized members of the family.

Alternatively, from the primary amino acid sequence, the secondary protein structure and, therefore, the extracellular domain regions may be deduced semi-empirically using a hydrophobicity/hydrophilicity calculation such as the Chou-Fasman method (see, e.g., Chou and Fasman, *Ann. Rev. Biochem.* (1978) 47:251). Hydrophilic domains, particularly ones surrounded by hydrophobic stretches (e.g., transmembrane domains) present themselves as strong candidates for extracellular domains. Finally, extracellular domains may be identified experimentally using standard enzymatic digest analysis, e.g., tryptic digest analysis.

Candidate fragments (e.g., any extracellular fragment) are tested for interaction with melatonin by the assays described herein (e.g., the assay described above). Such fragments are also tested for their ability to antagonize the interaction between melatonin and its endogenous receptor using the assays described herein. Analogs of useful receptor fragments (as described above) may also be produced and tested for efficacy as screening components or antagonists (using the assays described herein); such analogs are also considered to be useful in the invention.

Other embodiments are within the claims.

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 1320 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Coding Sequence
        ( B ) LOCATION: 32...1291
        ( D ) OTHER INFORMATION:

( x i ) SEQUENCE DESCRIPTION: SEQ ID NO:1:

```
TGCCTATCTC CCTTTGCCAG GGGGCAGAGA A ATG ATG GAG GTG AAT AGC ACT        52
                                   Met Met Glu Val Asn Ser Thr
                                    1                   5

TGC TTG GAT TGC AGG ACA CCT GGT ACC ATA CGA ACA GAG CAG GAT GCA       100
Cys Leu Asp Cys Arg Thr Pro Gly Thr Ile Arg Thr Glu Gln Asp Ala
            10              15                  20

CAG GAC AGC GCA TCT CAG GGA CTC ACC TCT GCC CTG GCG GTG GTT CTT       148
Gln Asp Ser Ala Ser Gln Gly Leu Thr Ser Ala Leu Ala Val Val Leu
        25              30                  35

ATA TTC ACC ATT GTT GTG GAT GTC CTG GGC AAT ATA TTG GTC ATT TTG       196
Ile Phe Thr Ile Val Val Asp Val Leu Gly Asn Ile Leu Val Ile Leu
40                  45                  50                  55

TCT GTC CTG AGG AAC AAG AAG CTG CAG AAT GCT GGA AAT CTC TTT GTT       244
Ser Val Leu Arg Asn Lys Lys Leu Gln Asn Ala Gly Asn Leu Phe Val
                60                  65                  70

GTC AGT TTG TCT ATT GCC GAT CTG GTT GTT GCT GTG TAT CCC TAT CCG       292
Val Ser Leu Ser Ile Ala Asp Leu Val Val Ala Val Tyr Pro Tyr Pro
            75                  80                  85

GTC ATT CTC ATA GCT ATT TTC CAG AAT GGA TGG ACG CTT GGA AAT ATC       340
Val Ile Leu Ile Ala Ile Phe Gln Asn Gly Trp Thr Leu Gly Asn Ile
                90                  95                  100

CAT TGT CAG ATC AGT GGC TTC CTG ATG GGA CTC AGC GTT ATT GGA TCA       388
His Cys Gln Ile Ser Gly Phe Leu Met Gly Leu Ser Val Ile Gly Ser
            105                 110                 115

GTC TTC AAC ATA ACA GCC ATA GCT ATC AAC AGG TAT TGC TAC ATC TGC       436
Val Phe Asn Ile Thr Ala Ile Ala Ile Asn Arg Tyr Cys Tyr Ile Cys
120                 125                 130                 135

CAC AGC CTG AGA TAT GAC AAG CTT TAT AAT CAA AGA AGC ACC TGG TGC       484
His Ser Leu Arg Tyr Asp Lys Leu Tyr Asn Gln Arg Ser Thr Trp Cys
                140                 145                 150

TAC CTT GGC CTG ACA TGG ATA CTA ACT ATA ATT GCA ATC GTG CCA AAC       532
Tyr Leu Gly Leu Thr Trp Ile Leu Thr Ile Ile Ala Ile Val Pro Asn
            155                 160                 165

TTT TTT GTT GGA TCA CTA CAG TAT GAC CCC AGG ATT TTT TCT TGC ACA       580
Phe Phe Val Gly Ser Leu Gln Tyr Asp Pro Arg Ile Phe Ser Cys Thr
                170                 175                 180

TTT GCG CAG ACA GTG AGT TCC TCA TAC ACC ATA ACA GTA GTG GTG GTG       628
Phe Ala Gln Thr Val Ser Ser Ser Tyr Thr Ile Thr Val Val Val Val
            185                 190                 195

CAT TTT ATA GTC CCT CTT AGT GTT GTG ACA TTC TGT TAC TTA AGA ATA       676
His Phe Ile Val Pro Leu Ser Val Val Thr Phe Cys Tyr Leu Arg Ile
200                 205                 210                 215

TGG GTT TTA GTG ATC CAA GTC AAA CAC AGA GTT AGA CAA GAC TTC AAG       724
Trp Val Leu Val Ile Gln Val Lys His Arg Val Arg Gln Asp Phe Lys
                220                 225                 230

CAA AAG TTG ACA CAA ACA GAC TTG AGA AAT TTC TTG ACC ATG TTT GTG       772
Gln Lys Leu Thr Gln Thr Asp Leu Arg Asn Phe Leu Thr Met Phe Val
            235                 240                 245

GTC TTT GTA CTT TTT GCA GTT TGC TGG GCC CCC TTA AAC TTT ATC GGC       820
Val Phe Val Leu Phe Ala Val Cys Trp Ala Pro Leu Asn Phe Ile Gly
                250                 255                 260

CTT GCT GTG GCC ATT AAT CCG TTT CAT GTG GCA CCA AAG ATT CCA GAA       868
Leu Ala Val Ala Ile Asn Pro Phe His Val Ala Pro Lys Ile Pro Glu
            265                 270                 275

TGG CTG TTT GTT TTA AGC TAT TTC ATG GCC TAT TTT AAC AGT TGT CTC       916
Trp Leu Phe Val Leu Ser Tyr Phe Met Ala Tyr Phe Asn Ser Cys Leu
280                 285                 290                 295

AAT GCT GTT ATA TAT GGT GTG CTA AAT CAA AAC TTC CGC AAG GAG TAC       964
Asn Ala Val Ile Tyr Gly Val Leu Asn Gln Asn Phe Arg Lys Glu Tyr
                300                 305                 310
```

```
AAA AGA ATA CTG ATG TCC TTA TTG ACT CCA AGA CTG TTG TTT CTT GAC          1012
Lys Arg Ile Leu Met Ser Leu Leu Thr Pro Arg Leu Leu Phe Leu Asp
            315                 320                 325

ACA TCT AGA GGA GGA ACT GAG GGA TTG AAA AGT AAG CCT TCG CCA GCT          1060
Thr Ser Arg Gly Gly Thr Glu Gly Leu Lys Ser Lys Pro Ser Pro Ala
        330                 335                 340

GTA ACC AAC AAC AAT CAA GCA GAT ATG CTA GGA GAA GCA AGG TCA CTG          1108
Val Thr Asn Asn Asn Gln Ala Asp Met Leu Gly Glu Ala Arg Ser Leu
        345                 350                 355

TGG CTG AGC AGG AGA AAT GGT GCG AAA ATG GTG ATC ATC ATC AGG CCA          1156
Trp Leu Ser Arg Arg Asn Gly Ala Lys Met Val Ile Ile Ile Arg Pro
360                 365                 370                 375

AGA AAA GCA CAA ATT GCA ATC ATC CAT CAA ATA TTC TGG CCT CAG AGT          1204
Arg Lys Ala Gln Ile Ala Ile Ile His Gln Ile Phe Trp Pro Gln Ser
                380                 385                 390

TCA TGG GCA ACA TGC CGT CAA GAC ACA AAG ATT ACC GGA GAA GAA GAT          1252
Ser Trp Ala Thr Cys Arg Gln Asp Thr Lys Ile Thr Gly Glu Glu Asp
            395                 400                 405

GGC TGC CGT GAA CTG TGC AAG GAC GGG ATT TCC CAA AGG TGAGACCAA TG         1303
Gly Cys Arg Glu Leu Cys Lys Asp Gly Ile Ser Gln Arg
        410                 415                 420

CACTATATCC ACATTAT                                                        1320
```

( 2 ) INFORMATION FOR SEQ ID NO:2:

( i ) SEQUENCE CHARACTERISTICS:
        ( A ) LENGTH: 420 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Met Met Glu Val Asn Ser Thr Cys Leu Asp Cys Arg Thr Pro Gly Thr
 1               5                  10                  15

Ile Arg Thr Glu Gln Asp Ala Gln Asp Ser Ala Ser Gln Gly Leu Thr
                20                  25                  30

Ser Ala Leu Ala Val Val Leu Ile Phe Thr Ile Val Val Asp Val Leu
            35                  40                  45

Gly Asn Ile Leu Val Ile Leu Ser Val Leu Arg Asn Lys Lys Leu Gln
        50                  55                  60

Asn Ala Gly Asn Leu Phe Val Val Ser Leu Ser Ile Ala Asp Leu Val
65                  70                  75                  80

Val Ala Val Tyr Pro Tyr Pro Val Ile Leu Ile Ala Ile Phe Gln Asn
                85                  90                  95

Gly Trp Thr Leu Gly Asn Ile His Cys Gln Ile Ser Gly Phe Leu Met
                100                 105                 110

Gly Leu Ser Val Ile Gly Ser Val Phe Asn Ile Thr Ala Ile Ala Ile
            115                 120                 125

Asn Arg Tyr Cys Tyr Ile Cys His Ser Leu Arg Tyr Asp Lys Leu Tyr
        130                 135                 140

Asn Gln Arg Ser Thr Trp Cys Tyr Leu Gly Leu Thr Trp Ile Leu Thr
145                 150                 155                 160

Ile Ile Ala Ile Val Pro Asn Phe Phe Val Gly Ser Leu Gln Tyr Asp
                165                 170                 175

Pro Arg Ile Phe Ser Cys Thr Phe Ala Gln Thr Val Ser Ser Ser Tyr
            180                 185                 190
```

```
Thr  Ile  Thr  Val  Val  Val  Val  His  Phe  Ile  Val  Pro  Leu  Ser  Val  Val
          195                      200                     205

Thr  Phe  Cys  Tyr  Leu  Arg  Ile  Trp  Val  Leu  Val  Ile  Gln  Val  Lys  His
     210                      215                     220

Arg  Val  Arg  Gln  Asp  Phe  Lys  Gln  Lys  Leu  Thr  Gln  Thr  Asp  Leu  Arg
225                      230                     235                          240

Asn  Phe  Leu  Thr  Met  Phe  Val  Val  Phe  Leu  Phe  Ala  Val  Cys  Trp
                    245                     250                     255

Ala  Pro  Leu  Asn  Phe  Ile  Gly  Leu  Ala  Val  Ala  Ile  Asn  Pro  Phe  His
               260                     265                     270

Val  Ala  Pro  Lys  Ile  Pro  Glu  Trp  Leu  Phe  Val  Leu  Ser  Tyr  Phe  Met
          275                     280                     285

Ala  Tyr  Phe  Asn  Ser  Cys  Leu  Asn  Ala  Val  Ile  Tyr  Gly  Val  Leu  Asn
     290                     295                     300

Gln  Asn  Phe  Arg  Lys  Glu  Tyr  Lys  Arg  Ile  Leu  Met  Ser  Leu  Leu  Thr
305                      310                     315                          320

Pro  Arg  Leu  Leu  Phe  Leu  Asp  Thr  Ser  Arg  Gly  Gly  Thr  Glu  Gly  Leu
                    325                     330                     335

Lys  Ser  Lys  Pro  Ser  Pro  Ala  Val  Thr  Asn  Asn  Asn  Gln  Ala  Asp  Met
               340                     345                     350

Leu  Gly  Glu  Ala  Arg  Ser  Leu  Trp  Leu  Ser  Arg  Arg  Asn  Gly  Ala  Lys
          355                     360                     365

Met  Val  Ile  Ile  Ile  Arg  Pro  Arg  Lys  Ala  Gln  Ile  Ala  Ile  Ile  His
     370                     375                     380

Gln  Ile  Phe  Trp  Pro  Gln  Ser  Ser  Trp  Ala  Thr  Cys  Arg  Gln  Asp  Thr
385                      390                     395                          400

Lys  Ile  Thr  Gly  Glu  Glu  Asp  Gly  Cys  Arg  Glu  Leu  Cys  Lys  Asp  Gly
                    405                     410                     415

Ile  Ser  Gln  Arg
               420
```

( 2 ) INFORMATION FOR SEQ ID NO:3:

( i ) SEQUENCE CHARACTERISTICS:
    ( A ) LENGTH: 1149 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: Coding Sequence
    ( B ) LOCATION: 49...1146
    ( D ) OTHER INFORMATION:

( x i ) SEQUENCE DESCRIPTION: SEQ ID NO:3:

```
GGGAGCTCGA  CGCTCTGGGG  ATCCACCGGC  GCCGGCCCTG  CCAGCGCG ATG GCG GGG       57
                                                         Met Ala Gly
                                                          1

CGG CTG TGG GGC TCG CCG GGC GGG ACC CCC AAG GGC AAC GGC AGC AGC           105
Arg Leu Trp Gly Ser Pro Gly Gly Thr Pro Lys Gly Asn Gly Ser Ser
     5                   10                  15

GCG CTG CTC AAC GTC TCG CAG GCG GCG CCC GGC GCC GGG GAC GGT GTG           153
Ala Leu Leu Asn Val Ser Gln Ala Ala Pro Gly Ala Gly Asp Gly Val
 20                  25                  30                  35

CGG CCG CGG CCC TCG TGG CTG GCC GCC ACC CTC GCC TCC ATC CTC ATC           201
Arg Pro Arg Pro Ser Trp Leu Ala Ala Thr Leu Ala Ser Ile Leu Ile
                 40                  45                  50
```

| | | | | | | | | | | | | | | | | |
|---|---|---|---|---|---|---|---|---|---|---|---|---|---|---|---|---|
| TTC | ACC | ATC | GTG | GTG | GAC | ATC | GTG | GGC | AAC | CTC | CTG | GTG | GTC | CTG | TCC | 249 |
| Phe | Thr | Ile | Val | Val | Asp | Ile | Val | Gly | Asn | Leu | Leu | Val | Val | Leu | Ser | |
| | | | 55 | | | | 60 | | | | | 65 | | | | |
| GTG | TAT | CGG | AAC | AAG | AAG | CTG | AGG | AAC | GCA | GGG | AAT | GTG | TTT | GTG | GTG | 297 |
| Val | Tyr | Arg | Asn | Lys | Lys | Leu | Arg | Asn | Ala | Gly | Asn | Val | Phe | Val | Val | |
| | | 70 | | | | 75 | | | | | 80 | | | | | |
| AGC | CTG | GCA | GTT | GCA | GAC | CTG | CTG | GTG | GCC | GTG | TAT | CCG | TAC | CCC | TTG | 345 |
| Ser | Leu | Ala | Val | Ala | Asp | Leu | Leu | Val | Ala | Val | Tyr | Pro | Tyr | Pro | Leu | |
| | 85 | | | | 90 | | | | | 95 | | | | | | |
| GCG | CTG | GCG | TCT | ATA | GTT | AAC | AAT | GGG | TGG | AGC | CTG | AGC | TCC | CTG | CAT | 393 |
| Ala | Leu | Ala | Ser | Ile | Val | Asn | Asn | Gly | Trp | Ser | Leu | Ser | Ser | Leu | His | |
| 100 | | | | | 105 | | | | | 110 | | | | | 115 | |
| TGC | CAA | CTT | AGT | GGC | TTC | CTG | ATG | GGC | TTG | AGC | GTC | ATC | GGG | TCC | GTT | 441 |
| Cys | Gln | Leu | Ser | Gly | Phe | Leu | Met | Gly | Leu | Ser | Val | Ile | Gly | Ser | Val | |
| | | | | 120 | | | | | 125 | | | | | 130 | | |
| TTC | AGC | ATC | ACG | GGA | ATT | GCC | ATC | AAC | CGC | TAT | TGC | TGC | ATC | TGC | CAC | 489 |
| Phe | Ser | Ile | Thr | Gly | Ile | Ala | Ile | Asn | Arg | Tyr | Cys | Cys | Ile | Cys | His | |
| | | | 135 | | | | 140 | | | | | 145 | | | | |
| AGC | CTC | AGA | TAC | GGC | AAG | CTG | TAT | AGC | GGC | ACG | AAT | TCC | CTC | TGC | TAC | 537 |
| Ser | Leu | Arg | Tyr | Gly | Lys | Leu | Tyr | Ser | Gly | Thr | Asn | Ser | Leu | Cys | Tyr | |
| | | 150 | | | | 155 | | | | | 160 | | | | | |
| GTG | TTC | CTG | ATC | TGG | ACG | CTG | ACG | CTC | GTG | GCG | ATC | GTG | CCC | AAC | CTG | 585 |
| Val | Phe | Leu | Ile | Trp | Thr | Leu | Thr | Leu | Val | Ala | Ile | Val | Pro | Asn | Leu | |
| | 165 | | | | 170 | | | | | 175 | | | | | | |
| TGT | GTG | GGG | ACC | CTG | CAG | TAC | GAC | CCG | AGG | ATC | TAT | TCC | TGT | ACC | TTC | 633 |
| Cys | Val | Gly | Thr | Leu | Gln | Tyr | Asp | Pro | Arg | Ile | Tyr | Ser | Cys | Thr | Phe | |
| 180 | | | | | 185 | | | | | 190 | | | | | 195 | |
| ACG | CAG | TCC | GTC | AGC | TCA | GCC | TAC | ACG | ATC | GCC | GTG | GTG | GTG | TTC | CAT | 681 |
| Thr | Gln | Ser | Val | Ser | Ser | Ala | Tyr | Thr | Ile | Ala | Val | Val | Val | Phe | His | |
| | | | | 200 | | | | | 205 | | | | | 210 | | |
| TTC | ATA | GTT | CCG | ATG | CTC | GTA | GTC | GTC | TTC | TGT | TAC | CTG | AGA | ATC | TGG | 729 |
| Phe | Ile | Val | Pro | Met | Leu | Val | Val | Val | Phe | Cys | Tyr | Leu | Arg | Ile | Trp | |
| | | | 215 | | | | 220 | | | | | 225 | | | | |
| GCC | CTG | GTT | CTT | CAG | GTC | AGA | TGG | AAG | GTG | AAA | CCG | GAC | AAC | AAA | CCG | 777 |
| Ala | Leu | Val | Leu | Gln | Val | Arg | Trp | Lys | Val | Lys | Pro | Asp | Asn | Lys | Pro | |
| | | 230 | | | | 235 | | | | | 240 | | | | | |
| AAA | CTG | AAG | CCC | CAG | GAC | TTC | AGG | AAT | TTT | GTC | ACC | ATG | TTT | GTG | GTT | 825 |
| Lys | Leu | Lys | Pro | Gln | Asp | Phe | Arg | Asn | Phe | Val | Thr | Met | Phe | Val | Val | |
| | 245 | | | | 250 | | | | | 255 | | | | | | |
| TTT | GTC | CTC | TTT | GCC | ATT | TGC | TGG | GCT | CCT | CTG | AAC | TTC | ATT | GGT | CTC | 873 |
| Phe | Val | Leu | Phe | Ala | Ile | Cys | Trp | Ala | Pro | Leu | Asn | Phe | Ile | Gly | Leu | |
| 260 | | | | | 265 | | | | | 270 | | | | | 275 | |
| GTT | GTG | GCC | TCG | GAC | CCC | GCC | AGC | ATG | GCA | CCC | AGG | ATC | CCC | GAG | TGG | 921 |
| Val | Val | Ala | Ser | Asp | Pro | Ala | Ser | Met | Ala | Pro | Arg | Ile | Pro | Glu | Trp | |
| | | | | 280 | | | | | 285 | | | | | 290 | | |
| CTG | TTT | GTG | GCT | AGT | TAC | TAT | ATG | GCA | TAT | TTC | AAC | AGC | TGC | CTC | AAT | 969 |
| Leu | Phe | Val | Ala | Ser | Tyr | Tyr | Met | Ala | Tyr | Phe | Asn | Ser | Cys | Leu | Asn | |
| | | | 295 | | | | 300 | | | | | 305 | | | | |
| GCG | ATC | ATA | TAT | GGA | CTA | CTG | AAC | CAA | AAT | TTC | AGG | CAG | GAA | TAC | AGA | 1017 |
| Ala | Ile | Ile | Tyr | Gly | Leu | Leu | Asn | Gln | Asn | Phe | Arg | Gln | Glu | Tyr | Arg | |
| | | 310 | | | | 315 | | | | | 320 | | | | | |
| AAA | ATT | ATA | GTC | TCA | TTG | TGT | ACC | ACC | AAG | ATG | TTC | TTT | GTG | GAT | AGC | 1065 |
| Lys | Ile | Ile | Val | Ser | Leu | Cys | Thr | Thr | Lys | Met | Phe | Phe | Val | Asp | Ser | |
| | 325 | | | | 330 | | | | | 335 | | | | | | |
| TCC | AAT | CAT | GTA | GCA | GAT | AGA | ATT | AAA | CGC | AAA | CCC | TCT | CCA | TTA | ATA | 1113 |
| Ser | Asn | His | Val | Ala | Asp | Arg | Ile | Lys | Arg | Lys | Pro | Ser | Pro | Leu | Ile | |
| 340 | | | | | 345 | | | | | 350 | | | | | 355 | |
| GCC | AAC | CAT | AAC | CTA | ATA | AAG | GTG | GAC | TCC | GTT | TAA | | | | | 1149 |
| Ala | Asn | His | Asn | Leu | Ile | Lys | Val | Asp | Ser | Val | | | | | | |
| | | | | 360 | | | | | 365 | | | | | | | |

( 2 ) INFORMATION FOR SEQ ID NO:4:

( i ) SEQUENCE CHARACTERISTICS:
    ( A ) LENGTH: 366 amino acids
    ( B ) TYPE: amino acid
    ( D ) TOPOLOGY: linear ( i i ) MOLECULE TYPE: protein ( v ) FRAGMENT TYPE: internal ( x i ) SEQUENCE DESCRIPTION: SEQ ID NO:4:

```
Met Ala Gly Arg Leu Trp Gly Ser Pro Gly Gly Thr Pro Lys Gly Asn
 1               5                  10                  15

Gly Ser Ser Ala Leu Leu Asn Val Ser Gln Ala Ala Pro Gly Ala Gly
                20                  25                  30

Asp Gly Val Arg Pro Arg Pro Ser Trp Leu Ala Ala Thr Leu Ala Ser
            35                  40                  45

Ile Leu Ile Phe Thr Ile Val Val Asp Ile Val Gly Asn Leu Leu Val
        50                  55                  60

Val Leu Ser Val Tyr Arg Asn Lys Lys Leu Arg Asn Ala Gly Asn Val
 65                 70                  75                  80

Phe Val Val Ser Leu Ala Val Ala Asp Leu Leu Val Ala Val Tyr Pro
                85                  90                  95

Tyr Pro Leu Ala Leu Ala Ser Ile Val Asn Asn Gly Trp Ser Leu Ser
            100                 105                 110

Ser Leu His Cys Gln Leu Ser Gly Phe Leu Met Gly Leu Ser Val Ile
            115                 120                 125

Gly Ser Val Phe Ser Ile Thr Gly Ile Ala Ile Asn Arg Tyr Cys Cys
        130                 135                 140

Ile Cys His Ser Leu Arg Tyr Gly Lys Leu Tyr Ser Gly Thr Asn Ser
145                 150                 155                 160

Leu Cys Tyr Val Phe Leu Ile Trp Thr Leu Thr Leu Val Ala Ile Val
                165                 170                 175

Pro Asn Leu Cys Val Gly Thr Leu Gln Tyr Asp Pro Arg Ile Tyr Ser
            180                 185                 190

Cys Thr Phe Thr Gln Ser Val Ser Ser Ala Tyr Thr Ile Ala Val Val
        195                 200                 205

Val Phe His Phe Ile Val Pro Met Leu Val Val Val Phe Cys Tyr Leu
    210                 215                 220

Arg Ile Trp Ala Leu Val Leu Gln Val Arg Trp Lys Val Lys Pro Asp
225                 230                 235                 240

Asn Lys Pro Lys Leu Lys Pro Gln Asp Phe Arg Asn Phe Val Thr Met
                245                 250                 255

Phe Val Val Phe Val Leu Phe Ala Ile Cys Trp Ala Pro Leu Asn Phe
            260                 265                 270

Ile Gly Leu Val Val Ala Ser Asp Pro Ala Ser Met Ala Pro Arg Ile
        275                 280                 285

Pro Glu Trp Leu Phe Val Ala Ser Tyr Tyr Met Ala Tyr Phe Asn Ser
    290                 295                 300

Cys Leu Asn Ala Ile Ile Tyr Gly Leu Leu Asn Gln Asn Phe Arg Gln
305                 310                 315                 320

Glu Tyr Arg Lys Ile Ile Val Ser Leu Cys Thr Thr Lys Met Phe Phe
                325                 330                 335

Val Asp Ser Ser Asn His Val Ala Asp Arg Ile Lys Arg Lys Pro Ser
            340                 345                 350
```

-continued

```
Pro  Leu  Ile  Ala  Asn  His  Asn  Leu  Ile  Lys  Val  Asp  Ser  Val
          355                 360                 365
```

( 2 ) INFORMATION FOR SEQ ID NO:5:

( i ) SEQUENCE CHARACTERISTICS:
        ( A ) LENGTH: 867 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: Coding Sequence
        ( B ) LOCATION: 1...864
        ( D ) OTHER INFORMATION:

( x i ) SEQUENCE DESCRIPTION: SEQ ID NO:5:

```
GGA  AAC  ATC  TTT  GTG  GTG  AGC  TTA  GCG  GTG  GCA  GAC  CTG  GTG  GTG  GCC       48
Gly  Asn  Ile  Phe  Val  Val  Ser  Leu  Ala  Val  Ala  Asp  Leu  Val  Val  Ala
 1                   5                        10                       15

ATT  TAT  CCG  TAC  CCG  TTG  GTG  CTG  ATG  TCG  ATA  TTT  AAC  AAC  GGG  TGG       96
Ile  Tyr  Pro  Tyr  Pro  Leu  Val  Leu  Met  Ser  Ile  Phe  Asn  Asn  Gly  Trp
               20                       25                       30

AAC  CTG  GGC  TAT  CTG  CAC  TGC  CAA  GTC  AGT  GGG  TTC  CTG  ATG  GGC  CTG      144
Asn  Leu  Gly  Tyr  Leu  His  Cys  Gln  Val  Ser  Gly  Phe  Leu  Met  Gly  Leu
          35                       40                       45

AGC  GTC  ATC  GGC  TCC  ATA  TTC  AAC  ATC  ACC  GGC  ATC  GCC  ATC  AAC  CGC      192
Ser  Val  Ile  Gly  Ser  Ile  Phe  Asn  Ile  Thr  Gly  Ile  Ala  Ile  Asn  Arg
     50                       55                       60

TAC  TGT  TAC  ATC  TGC  CAC  AGT  CTC  AAG  TGC  GAC  AAA  CTG  TAC  AGC  AGC      240
Tyr  Cys  Tyr  Ile  Cys  His  Ser  Leu  Lys  Cys  Asp  Lys  Leu  Tyr  Ser  Ser
 65                       70                       75                       80

AAG  AAC  TCC  CTC  TGC  TAC  GTG  CTC  CTC  ATA  TGG  CTC  CTG  ACG  GCG  GCC      288
Lys  Asn  Ser  Leu  Cys  Tyr  Val  Leu  Leu  Ile  Trp  Leu  Leu  Thr  Ala  Ala
                    85                       90                       95

GTC  CTG  CCC  AAC  CTC  CGT  CGT  GGG  ACT  CTC  CAG  TAC  GAG  CCG  AGG  ATC      336
Val  Leu  Pro  Asn  Leu  Arg  Arg  Gly  Thr  Leu  Gln  Tyr  Glu  Pro  Arg  Ile
               100                      105                      110

TAC  TCG  TGC  ACC  TTC  GCC  CAG  TCC  GTC  AGC  TCC  GCC  TAC  ACC  ATC  GCC      384
Tyr  Ser  Cys  Thr  Phe  Ala  Gln  Ser  Val  Ser  Ser  Ala  Tyr  Thr  Ile  Ala
          115                      120                      125

GTG  GTG  GTT  TTC  CAC  TTC  CTC  GTC  CCC  ATG  ATC  ATA  GTC  ATC  TTC  TGT      432
Val  Val  Val  Phe  His  Phe  Leu  Val  Pro  Met  Ile  Ile  Val  Ile  Phe  Cys
     130                      135                      140

TAC  CTG  AGA  ATA  TGG  ATC  CTG  GTT  CTC  CAG  GTC  AGA  CAG  AGG  GTG  AAA      480
Tyr  Leu  Arg  Ile  Trp  Ile  Leu  Val  Leu  Gln  Val  Arg  Gln  Arg  Val  Lys
145                      150                      155                      160

CCT  GAC  CGC  AAA  CCC  AAA  CTG  AAA  CCA  CAC  GAC  TTC  AGG  AAT  TTT  GTC      528
Pro  Asp  Arg  Lys  Pro  Lys  Leu  Lys  Pro  His  Asp  Phe  Arg  Asn  Phe  Val
                    165                      170                      175

ACC  ATG  TTT  GTG  GTT  TTT  GTC  CTT  TTT  GCC  ATT  TGC  TGG  GCT  CCT  CTG      576
Thr  Met  Phe  Val  Val  Phe  Val  Leu  Phe  Ala  Ile  Cys  Trp  Ala  Pro  Leu
               180                      185                      190

AAC  TTC  ATT  GGC  CTG  GCC  GTG  GCC  TCT  GAC  CCC  GCC  AGC  ATG  GTG  CCT      624
Asn  Phe  Ile  Gly  Leu  Ala  Val  Ala  Ser  Asp  Pro  Ala  Ser  Met  Val  Pro
          195                      200                      205

AGG  ATC  CCA  GAG  TGG  CTG  TTT  GTG  GCC  AGT  TAC  TAC  ATG  GCG  TAT  TTC      672
Arg  Ile  Pro  Glu  Trp  Leu  Phe  Val  Ala  Ser  Tyr  Tyr  Met  Ala  Tyr  Phe
     210                      215                      220

AAC  AGC  TGC  CTC  AAT  GCC  ATT  ATA  TCG  GGC  TAC  TGG  AAC  CAA  AAT  TTC      720
Asn  Ser  Cys  Leu  Asn  Ala  Ile  Ile  Ser  Gly  Tyr  Trp  Asn  Gln  Asn  Phe
225                      230                      235                      240
```

| AGG | AAG | GAA | TAC | AGG | AGA | ATT | ATA | GTC | TCG | CTC | GTG | ACA | GCC | AGG | GTG | 768 |
| Arg | Lys | Glu | Tyr | Arg | Arg | Ile | Ile | Val | Ser | Leu | Val | Thr | Ala | Arg | Val | |
| | | | | 245 | | | | | 250 | | | | | 255 | | |

| TTC | TTT | GTG | GAC | AGC | TCT | AAC | GAC | GTG | GCC | GAT | AGG | GTT | AAA | TGG | AAA | 816 |
| Phe | Phe | Val | Asp | Ser | Ser | Asn | Asp | Val | Ala | Asp | Arg | Val | Lys | Trp | Lys | |
| | | | 260 | | | | | 265 | | | | | 270 | | | |

| CCG | TCT | CCA | CTG | ATG | ACC | AAC | AAT | AAT | GTA | GTA | AAG | GTG | GAC | TCC | GTT | 864 |
| Pro | Ser | Pro | Leu | Met | Thr | Asn | Asn | Asn | Val | Val | Lys | Val | Asp | Ser | Val | |
| | | 275 | | | | | 280 | | | | | 285 | | | | |

TAA  867

( 2 ) INFORMATION FOR SEQ ID NO:6:

( i ) SEQUENCE CHARACTERISTICS:
        ( A ) LENGTH: 288 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:6:

```
Gly  Asn  Ile  Phe  Val  Val  Ser  Leu  Ala  Val  Ala  Asp  Leu  Val  Val  Ala
  1                 5                          10                         15

Ile  Tyr  Pro  Tyr  Pro  Leu  Val  Leu  Met  Ser  Ile  Phe  Asn  Asn  Gly  Trp
                 20                         25                    30

Asn  Leu  Gly  Tyr  Leu  His  Cys  Gln  Val  Ser  Gly  Phe  Leu  Met  Gly  Leu
            35                          40                         45

Ser  Val  Ile  Gly  Ser  Ile  Phe  Asn  Ile  Thr  Gly  Ile  Ala  Ile  Asn  Arg
 50                          55                          60

Tyr  Cys  Tyr  Ile  Cys  His  Ser  Leu  Lys  Cys  Asp  Lys  Leu  Tyr  Ser  Ser
 65                     70                          75                         80

Lys  Asn  Ser  Leu  Cys  Tyr  Val  Leu  Leu  Ile  Trp  Leu  Leu  Thr  Ala  Ala
                      85                          90                         95

Val  Leu  Pro  Asn  Leu  Arg  Arg  Gly  Thr  Leu  Gln  Tyr  Glu  Pro  Arg  Ile
                 100                         105                        110

Tyr  Ser  Cys  Thr  Phe  Ala  Gln  Ser  Val  Ser  Ser  Ala  Tyr  Thr  Ile  Ala
             115                         120                        125

Val  Val  Val  Phe  His  Phe  Leu  Val  Pro  Met  Ile  Ile  Val  Ile  Phe  Cys
130                          135                        140

Tyr  Leu  Arg  Ile  Trp  Ile  Leu  Val  Leu  Gln  Val  Arg  Gln  Arg  Val  Lys
145                          150                        155                      160

Pro  Asp  Arg  Lys  Pro  Lys  Leu  Lys  Pro  His  Asp  Phe  Arg  Asn  Phe  Val
                      165                        170                        175

Thr  Met  Phe  Val  Val  Phe  Val  Leu  Phe  Ala  Ile  Cys  Trp  Ala  Pro  Leu
                 180                        185                        190

Asn  Phe  Ile  Gly  Leu  Ala  Val  Ala  Ser  Asp  Pro  Ala  Ser  Met  Val  Pro
             195                        200                        205

Arg  Ile  Pro  Glu  Trp  Leu  Phe  Val  Ala  Ser  Tyr  Tyr  Met  Ala  Tyr  Phe
             210                        215                        220

Asn  Ser  Cys  Leu  Asn  Ala  Ile  Ile  Ser  Gly  Tyr  Trp  Asn  Gln  Asn  Phe
225                          230                        235                      240

Arg  Lys  Glu  Tyr  Arg  Arg  Ile  Ile  Val  Ser  Leu  Val  Thr  Ala  Arg  Val
                      245                        250                        255

Phe  Phe  Val  Asp  Ser  Ser  Asn  Asp  Val  Ala  Asp  Arg  Val  Lys  Trp  Lys
                 260                        265                        270
```

-continued

Pro Ser Pro Leu Met Thr Asn Asn Asn Val Val Lys Val Asp Ser Val
    275                 280                 285

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:7:

Asn Pro Xaa Xaa Tyr
 1               5

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:8:

Ala Ile Ala Ile Asn Arg Tyr
 1               5

(2) INFORMATION FOR SEQ ID NO:9:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:9:

Phe Ala Val Cys Trp Ala Pro Leu
 1               5

(2) INFORMATION FOR SEQ ID NO:10:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:10:

Gly Asn Xaa Phe Val Val
 1               5

(2) INFORMATION FOR SEQ ID NO:11:

(i) SEQUENCE CHARACTERISTICS:
        (A) LENGTH: 1085 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: Coding Sequence
        (B) LOCATION: 33...1082
        (D) OTHER INFORMATION:

(xi) SEQUENCE DESCRIPTION: SEQ ID NO:11:

```
ATGGCCCTGC GGCCGGGACG CGAACAGGGA CC ATG CAG GGC AAC GGC AGC GCG        53
                                      Met Gln Gly Asn Gly Ser Ala
                                       1               5

CTG CCC AAC GCC TCC CAG CCC GTG CTC CGC GGG GAC GGC GCG CGG CCC       101
Leu Pro Asn Ala Ser Gln Pro Val Leu Arg Gly Asp Gly Ala Arg Pro
         10              15                  20

TCG TGG CTG GCG TCC GCC CTA GCC TGC GTC CTC ATC TTC ACC ATC GTG       149
Ser Trp Leu Ala Ser Ala Leu Ala Cys Val Leu Ile Phe Thr Ile Val
     25              30              35

GTG GAC ATC CTG GGC AAC CTC CTG GTC ATC CTG TCG GTG TAT CGG AAC       197
Val Asp Ile Leu Gly Asn Leu Leu Val Ile Leu Ser Val Tyr Arg Asn
 40              45              50                          55

AAG AAG CTC AGG AAC GCA GGA AAC ATC TTT GTG GTG AGC TTA GCG GTG       245
Lys Lys Leu Arg Asn Ala Gly Asn Ile Phe Val Val Ser Leu Ala Val
             60              65                          70

GCA GAC CTG GTG GTG GCC ATT TAT CCG TAC CCG TTG GTG CTG ATG TCG       293
Ala Asp Leu Val Val Ala Ile Tyr Pro Tyr Pro Leu Val Leu Met Ser
                 75              80                  85

ATA TTT AAC AAC GGG TGG AAC CTG GGC TAT CTG CAC TGC CAA GTC AGT       341
Ile Phe Asn Asn Gly Trp Asn Leu Gly Tyr Leu His Cys Gln Val Ser
             90              95                 100

GGG TTC CTG ATG GGC CTG AGC GTC ATC GGC TCC ATA TTC AAC ATC ACC       389
Gly Phe Leu Met Gly Leu Ser Val Ile Gly Ser Ile Phe Asn Ile Thr
        105             110                 115

GGC ATC GCC ATC AAC CGC TAC TGC TAC ATC TGC CAC AGT CTC AAG TAC       437
Gly Ile Ala Ile Asn Arg Tyr Cys Tyr Ile Cys His Ser Leu Lys Tyr
120             125                 130                     135

GAC AAA CTG TAC AGC AGC AAG AAC TCC CTC TGC TAC GTG CTC CTC ATA       485
Asp Lys Leu Tyr Ser Ser Lys Asn Ser Leu Cys Tyr Val Leu Leu Ile
                140             145                 150

TGG CTC CTG ACG CTG GCG GCC GTC CTG CCC AAC CTC CGT GCA GGG ACT       533
Trp Leu Leu Thr Leu Ala Ala Val Leu Pro Asn Leu Arg Ala Gly Thr
            155             160                 165

CTC CAG TAC GAC CCG AGG ATC TAC TCG TGC ACC TTC GCC CAG TCC GTC       581
Leu Gln Tyr Asp Pro Arg Ile Tyr Ser Cys Thr Phe Ala Gln Ser Val
        170             175                 180

AGC TCC GCC TAC ACC ATC GCC GTG GTG GTT TTC CAC TTC CTC GTC CCC       629
Ser Ser Ala Tyr Thr Ile Ala Val Val Val Phe His Phe Leu Val Pro
185             190                 195

ATG ATC ATA GTC ATC TTC TGT TAC CTG AGA ATA TGG ATC CTG GTT CTC       677
Met Ile Ile Val Ile Phe Cys Tyr Leu Arg Ile Trp Ile Leu Val Leu
200             205                 210                     215

CAG GTC AGA CAG AGG GTG AAA CCT GAC CGC AAA CCC AAA CTG AAA CCA       725
Gln Val Arg Gln Arg Val Lys Pro Asp Arg Lys Pro Lys Leu Lys Pro
            220             225                 230

CAG GAC TTC AGG AAT TTT GTC ACC ATG TTT GTG GTT TTT GTC CTC TTT       773
Gln Asp Phe Arg Asn Phe Val Thr Met Phe Val Val Phe Val Leu Phe
        235             240                 245

GCC ATT TGC TGG GCT CCT CTG AAC TTC ATT GGC CTG GCC GTG GCC TCT       821
Ala Ile Cys Trp Ala Pro Leu Asn Phe Ile Gly Leu Ala Val Ala Ser
        250             255                 260

GAC CCC GCC AGC ATG GTG CCT AGG ATC CCA GAG TGG CTG TTT GTG GCC       869
Asp Pro Ala Ser Met Val Pro Arg Ile Pro Glu Trp Leu Phe Val Ala
265             270                 275

AGT TAC TAC ATG GCG TAT TTC AAC AGC TGC CTC AAT GCC ATT ATA TAC       917
Ser Tyr Tyr Met Ala Tyr Phe Asn Ser Cys Leu Asn Ala Ile Ile Tyr
280             285                 290                     295

GGG CTA CTG AAC CAA AAT TTC AGG AAG GAA TAC AGG AGA ATT ATA GTC       965
Gly Leu Leu Asn Gln Asn Phe Arg Lys Glu Tyr Arg Arg Ile Ile Val
            300             305                 310
```

| | | | | | | | | | | | | | | | | |
|---|---|---|---|---|---|---|---|---|---|---|---|---|---|---|---|---|
| TCG | CTC | TGT | ACA | GCC | AGG | GTG | TTC | TTT | GTG | GAC | AGC | TCT | AAC | GAC | GTG | 1013 |
| Ser | Leu | Cys | Thr | Ala | Arg | Val | Phe | Phe | Val | Asp | Ser | Ser | Asn | Asp | Val | |
| | | 315 | | | | | 320 | | | | | 325 | | | | |
| GCC | GAT | AGG | GTT | AAA | TGG | AAA | CCG | TCT | CCA | CTG | ATG | ACC | AAC | AAT | AAT | 1061 |
| Ala | Asp | Arg | Val | Lys | Trp | Lys | Pro | Ser | Pro | Leu | Met | Thr | Asn | Asn | Asn | |
| | | 330 | | | | | 335 | | | | | 340 | | | | |
| GTA | GTA | AAG | GTG | GAC | TCC | GTT | TAA | | | | | | | | | 1085 |
| Val | Val | Lys | Val | Asp | Ser | Val | | | | | | | | | | |
| | | 345 | | | | 350 | | | | | | | | | | |

( 2 ) INFORMATION FOR SEQ ID NO:12:

( i ) SEQUENCE CHARACTERISTICS:
        ( A ) LENGTH: 350 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:12:

| | | | | | | | | | | | | | | |
|---|---|---|---|---|---|---|---|---|---|---|---|---|---|---|
| Met | Gln | Gly | Asn | Gly | Ser | Ala | Leu | Pro | Asn | Ala | Ser | Gln | Pro | Val | Leu |
| 1 | | | | 5 | | | | | 10 | | | | | 15 |
| Arg | Gly | Asp | Gly | Ala | Arg | Pro | Ser | Trp | Leu | Ala | Ser | Ala | Leu | Ala | Cys |
| | | | 20 | | | | | 25 | | | | | 30 | |
| Val | Leu | Ile | Phe | Thr | Ile | Val | Val | Asp | Ile | Leu | Gly | Asn | Leu | Leu | Val |
| | | | 35 | | | | | 40 | | | | | 45 | |
| Ile | Leu | Ser | Val | Tyr | Arg | Asn | Lys | Lys | Leu | Arg | Asn | Ala | Gly | Asn | Ile |
| | | 50 | | | | | 55 | | | | | 60 | | |
| Phe | Val | Val | Ser | Leu | Ala | Val | Ala | Asp | Leu | Val | Val | Ala | Ile | Tyr | Pro |
| 65 | | | | | 70 | | | | | 75 | | | | | 80 |
| Tyr | Pro | Leu | Val | Leu | Met | Ser | Ile | Phe | Asn | Asn | Gly | Trp | Asn | Leu | Gly |
| | | | | 85 | | | | | 90 | | | | | 95 | |
| Tyr | Leu | His | Cys | Gln | Val | Ser | Gly | Phe | Leu | Met | Gly | Leu | Ser | Val | Ile |
| | | | 100 | | | | | 105 | | | | | 110 | | |
| Gly | Ser | Ile | Phe | Asn | Ile | Thr | Gly | Ile | Ala | Ile | Asn | Arg | Tyr | Cys | Tyr |
| | | 115 | | | | | 120 | | | | | 125 | | | |
| Ile | Cys | His | Ser | Leu | Lys | Tyr | Asp | Lys | Leu | Tyr | Ser | Ser | Lys | Asn | Ser |
| | 130 | | | | | 135 | | | | | 140 | | | | |
| Leu | Cys | Tyr | Val | Leu | Leu | Ile | Trp | Leu | Leu | Thr | Leu | Ala | Ala | Val | Leu |
| 145 | | | | | 150 | | | | | 155 | | | | | 160 |
| Pro | Asn | Leu | Arg | Ala | Gly | Thr | Leu | Gln | Tyr | Asp | Pro | Arg | Ile | Tyr | Ser |
| | | | | 165 | | | | | 170 | | | | | 175 | |
| Cys | Thr | Phe | Ala | Gln | Ser | Val | Ser | Ser | Ala | Tyr | Thr | Ile | Ala | Val | Val |
| | | | 180 | | | | | 185 | | | | | 190 | | |
| Val | Phe | His | Phe | Leu | Val | Pro | Met | Ile | Ile | Val | Ile | Phe | Cys | Tyr | Leu |
| | | 195 | | | | | 200 | | | | | 205 | | | |
| Arg | Ile | Trp | Ile | Leu | Val | Leu | Gln | Val | Arg | Gln | Arg | Val | Lys | Pro | Asp |
| | | 210 | | | | | 215 | | | | | 220 | | | |
| Arg | Lys | Pro | Lys | Leu | Lys | Pro | Gln | Asp | Phe | Arg | Asn | Phe | Val | Thr | Met |
| 225 | | | | | 230 | | | | | 235 | | | | | 240 |
| Phe | Val | Val | Phe | Val | Leu | Phe | Ala | Ile | Cys | Trp | Ala | Pro | Leu | Asn | Phe |
| | | | | 245 | | | | | 250 | | | | | 255 | |
| Ile | Gly | Leu | Ala | Val | Ala | Ser | Asp | Pro | Ala | Ser | Met | Val | Pro | Arg | Ile |
| | | | 260 | | | | | 265 | | | | | 270 | | |
| Pro | Glu | Trp | Leu | Phe | Val | Ala | Ser | Tyr | Tyr | Met | Ala | Tyr | Phe | Asn | Ser |
| | | 275 | | | | | 280 | | | | | 285 | | | |

| Cys | Leu | Asn | Ala | Ile | Ile | Tyr | Gly | Leu | Leu | Asn | Gln | Asn | Phe | Arg | Lys |
| | 290 | | | | 295 | | | | | 300 | | | | | |

| Glu | Tyr | Arg | Arg | Ile | Ile | Val | Ser | Leu | Cys | Thr | Ala | Arg | Val | Phe | Phe |
| 305 | | | | | 310 | | | | | 315 | | | | | 320 |

| Val | Asp | Ser | Ser | Asn | Asp | Val | Ala | Asp | Arg | Val | Lys | Trp | Lys | Pro | Ser |
| | | | | 325 | | | | | 330 | | | | | 335 | |

| Pro | Leu | Met | Thr | Asn | Asn | Asn | Val | Val | Lys | Val | Asp | Ser | Val |
| | | | 340 | | | | | 345 | | | | | 350 |

( 2 ) INFORMATION FOR SEQ ID NO:13:

( i ) SEQUENCE CHARACTERISTICS:
        ( A ) LENGTH: 1062 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Coding Sequence
        ( B ) LOCATION: 1...1059
        ( D ) OTHER INFORMATION:

( x i ) SEQUENCE DESCRIPTION: SEQ ID NO:13:

| ATG | AAG | GGC | AAT | GTC | AGC | GAG | CTG | CTC | AAT | GCC | ACT | CAG | CAG | GCT | CCA | 48 |
| Met | Lys | Gly | Asn | Val | Ser | Glu | Leu | Leu | Asn | Ala | Thr | Gln | Gln | Ala | Pro | |
| 1 | | | | 5 | | | | | 10 | | | | | 15 | | |

| GGC | GGC | GGG | GAG | GGA | GGG | AGA | CCA | CGA | CCG | TCC | TGG | ATG | GCC | TCT | ACA | 96 |
| Gly | Gly | Gly | Glu | Gly | Gly | Arg | Pro | Arg | Pro | Ser | Trp | Met | Ala | Ser | Thr | |
| | | | 20 | | | | | 25 | | | | | 30 | | | |

| CTG | GCC | TTC | ATC | CTC | ATC | TTT | ACC | ATC | GTG | GTG | GAC | ATT | CTG | GGC | AAC | 144 |
| Leu | Ala | Phe | Ile | Leu | Ile | Phe | Thr | Ile | Val | Val | Asp | Ile | Leu | Gly | Asn | |
| | | | 35 | | | | | 40 | | | | | 45 | | | |

| CTG | CTG | GTC | ATC | CTG | TCT | GTG | TAC | CGC | AAC | AAG | AAG | CTC | AGG | AAC | TCA | 192 |
| Leu | Leu | Val | Ile | Leu | Ser | Val | Tyr | Arg | Asn | Lys | Lys | Leu | Arg | Asn | Ser | |
| | 50 | | | | | 55 | | | | | 60 | | | | | |

| GGG | AAT | ATA | TTT | GTG | GTG | AGT | TTA | GCT | GTG | GCA | GAC | CTC | GTG | GTG | GCT | 240 |
| Gly | Asn | Ile | Phe | Val | Val | Ser | Leu | Ala | Val | Ala | Asp | Leu | Val | Val | Ala | |
| 65 | | | | | 70 | | | | | 75 | | | | | 80 | |

| GTT | TAC | CCT | TAT | CCC | TTG | GTG | CTG | ACA | TCT | ATC | CTT | AAC | AAC | GGA | TGG | 288 |
| Val | Tyr | Pro | Tyr | Pro | Leu | Val | Leu | Thr | Ser | Ile | Leu | Asn | Asn | Gly | Trp | |
| | | | | 85 | | | | | 90 | | | | | 95 | | |

| AAT | CTG | GGA | TAT | CTA | CAC | TGT | CAA | GTC | AGC | GCA | TTT | CTA | ATG | GGC | TTG | 336 |
| Asn | Leu | Gly | Tyr | Leu | His | Cys | Gln | Val | Ser | Ala | Phe | Leu | Met | Gly | Leu | |
| | | | | 100 | | | | | 105 | | | | | 110 | | |

| AGT | GTC | ATC | GGC | TCG | ATA | TTG | AAC | ATC | ACG | GGG | ATC | GCT | ATG | AAC | CGT | 384 |
| Ser | Val | Ile | Gly | Ser | Ile | Leu | Asn | Ile | Thr | Gly | Ile | Ala | Met | Asn | Arg | |
| | | | 115 | | | | | 120 | | | | | 125 | | | |

| TAC | TGC | TAC | ATT | TGC | CAC | AGC | CTC | AAG | TAC | GAC | AAA | ATA | TAC | AGT | AAC | 432 |
| Tyr | Cys | Tyr | Ile | Cys | His | Ser | Leu | Lys | Tyr | Asp | Lys | Ile | Tyr | Ser | Asn | |
| | 130 | | | | | 135 | | | | | 140 | | | | | |

| AAG | AAC | TCG | CTC | TGC | TAC | GTG | TTC | CTG | ATA | TGG | ATG | CTG | ACA | CTC | ATC | 480 |
| Lys | Asn | Ser | Leu | Cys | Tyr | Val | Phe | Leu | Ile | Trp | Met | Leu | Thr | Leu | Ile | |
| 145 | | | | | 150 | | | | | 155 | | | | | 160 | |

| GCC | ATC | ATG | CCC | AAC | CTG | CAA | ACC | GGA | ACA | CTC | CAG | TAC | GAT | CCC | CGG | 528 |
| Ala | Ile | Met | Pro | Asn | Leu | Gln | Thr | Gly | Thr | Leu | Gln | Tyr | Asp | Pro | Arg | |
| | | | | 165 | | | | | 170 | | | | | 175 | | |

| ATC | TAC | TCC | TGT | ACC | TTC | ACC | CAG | TCT | GTC | AGC | TCA | GCG | TAC | ACG | ATA | 576 |
| Ile | Tyr | Ser | Cys | Thr | Phe | Thr | Gln | Ser | Val | Ser | Ser | Ala | Tyr | Thr | Ile | |
| | | | 180 | | | | | 185 | | | | | 190 | | | |

| GCA | GTG | GTG | GTT | TTC | CAT | TTC | ATC | GTG | CCT | ATG | ATT | ATT | GTC | ATC | TTC | 624 |

| | | | | | | | | | | | | | | |
|---|---|---|---|---|---|---|---|---|---|---|---|---|---|---|
| Ala | Val | Val 195 | Val | Phe | His | Phe | Ile 200 | Val | Pro | Met | Ile | Ile 205 | Val | Ile | Phe |

| | | | | | | | | | | | | | | |
|---|---|---|---|---|---|---|---|---|---|---|---|---|---|---|
| TGC | TAC | TTA | AGG | ATA | TGG | GTC | CTG | GTC | CTT | CAG | GTC | AGA | CGG | AGG | GTG | 672 |
| Cys | Tyr 210 | Leu | Arg | Ile | Trp | Val 215 | Leu | Val | Leu | Gln | Val 220 | Arg | Arg | Arg | Val |

| | | | | | | | | | | | | | | |
|---|---|---|---|---|---|---|---|---|---|---|---|---|---|---|
| AAA | CCC | GAC | AAC | AAG | CCC | AAA | CTG | AAG | CCC | CAG | GAC | TTC | AGG | AAC | TTT | 720 |
| Lys 225 | Pro | Asp | Asn | Lys | Pro 230 | Lys | Leu | Lys | Pro | Gln 235 | Asp | Phe | Arg | Asn | Phe 240 |

| | | | | | | | | | | | | | | |
|---|---|---|---|---|---|---|---|---|---|---|---|---|---|---|
| GTC | ACC | ATG | TTC | GTA | GTT | TTT | GTA | CTT | TTT | GCC | ATT | TGT | TGG | GCC | CCA | 768 |
| Val | Thr | Met | Phe | Val 245 | Val | Phe | Val | Leu | Phe 250 | Ala | Ile | Cys | Trp | Ala 255 | Pro |

| | | | | | | | | | | | | | | |
|---|---|---|---|---|---|---|---|---|---|---|---|---|---|---|
| CTC | AAC | CTC | ATA | GGT | CTT | ATT | GTG | GCC | TCA | GAC | CCT | GCC | ACC | ATG | GTC | 816 |
| Leu | Asn | Leu | Ile 260 | Gly | Leu | Ile | Val | Ala 265 | Ser | Asp | Pro | Ala | Thr 270 | Met | Val |

| | | | | | | | | | | | | | | |
|---|---|---|---|---|---|---|---|---|---|---|---|---|---|---|
| CCC | AGG | ATC | CCA | GAG | TGG | CTG | TTC | GTG | GCT | AGT | TAC | TAC | CTG | GCG | TAC | 864 |
| Pro | Arg | Ile 275 | Pro | Glu | Trp | Leu | Phe 280 | Val | Ala | Ser | Tyr | Tyr 285 | Leu | Ala | Tyr |

| | | | | | | | | | | | | | | |
|---|---|---|---|---|---|---|---|---|---|---|---|---|---|---|
| TTC | AAC | AGC | TGC | CTC | AAC | GCA | ATT | ATA | TAC | GGA | CTA | CTG | AAT | CAG | AAT | 912 |
| Phe | Asn 290 | Ser | Cys | Leu | Asn | Ala 295 | Ile | Ile | Tyr | Gly | Leu 300 | Leu | Asn | Gln | Asn |

| | | | | | | | | | | | | | | |
|---|---|---|---|---|---|---|---|---|---|---|---|---|---|---|
| TTC | AGA | AAG | GAA | TAC | AAA | AAG | ATT | ATT | GTC | TCG | TTG | TGC | ACA | GCC | AAG | 960 |
| Phe | Arg | Lys | Glu | Tyr 310 | Lys | Lys | Ile | Ile | Val 315 | Ser | Leu | Cys | Thr | Ala | Lys 320 |
| 305 |

| | | | | | | | | | | | | | | |
|---|---|---|---|---|---|---|---|---|---|---|---|---|---|---|
| ATG | TTC | TTT | GTG | GAG | AGT | TCA | AAT | GAA | GAA | GCA | GAT | AAG | ATT | AAA | TGT | 1008 |
| Met | Phe | Phe | Val | Glu 325 | Ser | Ser | Asn | Glu | Glu 330 | Ala | Asp | Lys | Ile | Lys 335 | Cys |

| | | | | | | | | | | | | | | |
|---|---|---|---|---|---|---|---|---|---|---|---|---|---|---|
| AAG | CCC | TCT | CCA | CTA | ATA | CCC | AAT | AAT | AAC | TTC | CTC | CCG | GTG | GAC | TCT | 1056 |
| Lys | Pro | Ser | Pro 340 | Leu | Ile | Pro | Asn | Asn 345 | Asn | Phe | Leu | Pro | Val 350 | Asp | Ser |

| | |
|---|---|
| GTT | TAA | 1062 |
| Val | |

( 2 ) INFORMATION FOR SEQ ID NO:14:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:14:

| | | | | | | | | | | | | | | |
|---|---|---|---|---|---|---|---|---|---|---|---|---|---|---|
| Met 1 | Lys | Gly | Asn | Val 5 | Ser | Glu | Leu | Leu | Asn 10 | Ala | Thr | Gln | Gln | Ala 15 | Pro |

| | | | | | | | | | | | | | | |
|---|---|---|---|---|---|---|---|---|---|---|---|---|---|---|
| Gly | Gly | Gly | Glu 20 | Gly | Gly | Arg | Pro | Arg 25 | Pro | Ser | Trp | Met | Ala 30 | Ser | Thr |

| | | | | | | | | | | | | | | |
|---|---|---|---|---|---|---|---|---|---|---|---|---|---|---|
| Leu | Ala | Phe 35 | Ile | Leu | Ile | Phe | Thr 40 | Ile | Val | Val | Asp | Ile 45 | Leu | Gly | Asn |

| | | | | | | | | | | | | | | |
|---|---|---|---|---|---|---|---|---|---|---|---|---|---|---|
| Leu | Leu 50 | Val | Ile | Leu | Ser | Val 55 | Tyr | Arg | Asn | Lys | Lys 60 | Leu | Arg | Asn | Ser |

| | | | | | | | | | | | | | | |
|---|---|---|---|---|---|---|---|---|---|---|---|---|---|---|
| Gly 65 | Asn | Ile | Phe | Val | Val 70 | Ser | Leu | Ala | Val | Ala 75 | Asp | Leu | Val | Val | Ala 80 |

| | | | | | | | | | | | | | | |
|---|---|---|---|---|---|---|---|---|---|---|---|---|---|---|
| Val | Tyr | Pro | Tyr | Pro 85 | Leu | Val | Leu | Thr | Ser 90 | Ile | Leu | Asn | Asn | Gly 95 | Trp |

| | | | | | | | | | | | | | | |
|---|---|---|---|---|---|---|---|---|---|---|---|---|---|---|
| Asn | Leu | Gly | Tyr 100 | Leu | His | Cys | Gln | Val 105 | Ser | Ala | Phe | Leu | Met 110 | Gly | Leu |

| | | | | | | | | | | | | | | |
|---|---|---|---|---|---|---|---|---|---|---|---|---|---|---|
| Ser | Val | Ile 115 | Gly | Ser | Ile | Leu | Asn 120 | Ile | Thr | Gly | Ile | Ala 125 | Met | Asn | Arg |

```
Tyr  Cys  Tyr  Ile  Cys  His  Ser  Leu  Lys  Tyr  Asp  Lys  Ile  Tyr  Ser  Asn
          130                 135                140

Lys  Asn  Ser  Leu  Cys  Tyr  Val  Phe  Leu  Ile  Trp  Met  Leu  Thr  Leu  Ile
145                      150                 155                           160

Ala  Ile  Met  Pro  Asn  Leu  Gln  Thr  Gly  Thr  Leu  Gln  Tyr  Asp  Pro  Arg
                    165                 170                           175

Ile  Tyr  Ser  Cys  Thr  Phe  Thr  Gln  Ser  Val  Ser  Ser  Ala  Tyr  Thr  Ile
               180                 185                           190

Ala  Val  Val  Val  Phe  His  Phe  Ile  Val  Pro  Met  Ile  Ile  Val  Ile  Phe
               195                 200                      205

Cys  Tyr  Leu  Arg  Ile  Trp  Val  Leu  Val  Leu  Gln  Val  Arg  Arg  Arg  Val
          210                 215                 220

Lys  Pro  Asp  Asn  Lys  Pro  Lys  Leu  Lys  Pro  Gln  Asp  Phe  Arg  Asn  Phe
225                      230                 235                           240

Val  Thr  Met  Phe  Val  Val  Phe  Val  Leu  Phe  Ala  Ile  Cys  Trp  Ala  Pro
                    245                 250                      255

Leu  Asn  Leu  Ile  Gly  Leu  Ile  Val  Ala  Ser  Asp  Pro  Ala  Thr  Met  Val
               260                 265                      270

Pro  Arg  Ile  Pro  Glu  Trp  Leu  Phe  Val  Ala  Ser  Tyr  Tyr  Leu  Ala  Tyr
          275                 280                 285

Phe  Asn  Ser  Cys  Leu  Asn  Ala  Ile  Ile  Tyr  Gly  Leu  Leu  Asn  Gln  Asn
     290                      295                      300

Phe  Arg  Lys  Glu  Tyr  Lys  Lys  Ile  Ile  Val  Ser  Leu  Cys  Thr  Ala  Lys
305                      310                 315                           320

Met  Phe  Phe  Val  Glu  Ser  Ser  Asn  Glu  Glu  Ala  Asp  Lys  Ile  Lys  Cys
                    325                 330                      335

Lys  Pro  Ser  Pro  Leu  Ile  Pro  Asn  Asn  Asn  Phe  Leu  Pro  Val  Asp  Ser
               340                 345                      350

Val
```

( 2 ) INFORMATION FOR SEQ ID NO:15:

( i ) SEQUENCE CHARACTERISTICS:
        ( A ) LENGTH: 1105 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: Coding Sequence
        ( B ) LOCATION: 13...1098
        ( D ) OTHER INFORMATION:

( x i ) SEQUENCE DESCRIPTION: SEQ ID NO:15:

```
GGAGAGTCTG CG ATG TCA GAG AAC GGC TCC TTC GCC AAC TGC TGC GAG GCG        51
              Met Ser Glu Asn Gly Ser Phe Ala Asn Cys Cys Glu Ala
               1               5                  10

GGC GGG TGG GCA GTG CGC CCG GGC TGG TCG GGG GCT GGC AGC GCG CGG          99
Gly Gly Trp Ala Val Arg Pro Gly Trp Ser Gly Ala Gly Ser Ala Arg
         15              20                  25

CCC TCC AGG ACC CCT CGA CCT CCC TGG GTG GCT CCA GCG CTG TCC GCG         147
Pro Ser Arg Thr Pro Arg Pro Pro Trp Val Ala Pro Ala Leu Ser Ala
 30              35              40                      45

GTG CTC ATC GTC ACC ACC GCC GTG GAC GTC GTG GGC AAC CTC CTG GTG         195
Val Leu Ile Val Thr Thr Ala Val Asp Val Val Gly Asn Leu Leu Val
             50                  55                      60

ATC CTC TCC GTG CTC AGG AAC CGC AAG CTC CGG AAC GCA GGT AAT TTG         243
Ile Leu Ser Val Leu Arg Asn Arg Lys Leu Arg Asn Ala Gly Asn Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 65  |     |     |     |     | 70  |     |     |     |     | 75  |     |     |      |
| TTC | TTG | GTG | AGT | CTG | GCA | TTG | GCT | GAC | CTG | GTG | GTG | GCC | TTC | TAC | CCC | 291  |
| Phe | Leu | Val | Ser | Leu | Ala | Leu | Ala | Asp | Leu | Val | Val | Ala | Phe | Tyr | Pro |      |
|     |     | 80  |     |     |     |     | 85  |     |     |     |     | 90  |     |     |     |      |
| TAC | CCG | CTA | ATC | CTC | GTG | GCC | ATC | TTC | TAT | GAC | GGC | TGG | GCC | CTG | GGG | 339  |
| Tyr | Pro | Leu | Ile | Leu | Val | Ala | Ile | Phe | Tyr | Asp | Gly | Trp | Ala | Leu | Gly |      |
|     | 95  |     |     |     |     | 100 |     |     |     |     | 105 |     |     |     |     |      |
| GAG | GAG | CAC | TGC | AAG | GCC | AGC | GCC | TTT | GTG | ATG | GGC | CTG | AGC | GTC | ATC | 387  |
| Glu | Glu | His | Cys | Lys | Ala | Ser | Ala | Phe | Val | Met | Gly | Leu | Ser | Val | Ile |      |
| 110 |     |     |     |     | 115 |     |     |     |     | 120 |     |     |     |     | 125 |      |
| GGC | TCT | GTC | TTC | AAT | ATC | ACT | GCC | ATC | GCC | ATT | AAC | CGC | TAC | TGC | TAC | 435  |
| Gly | Ser | Val | Phe | Asn | Ile | Thr | Ala | Ile | Ala | Ile | Asn | Arg | Tyr | Cys | Tyr |      |
|     |     |     |     | 130 |     |     |     |     | 135 |     |     |     |     | 140 |     |      |
| ATC | TGC | CAC | AGC | ATG | GCC | TAC | CAC | CGA | ATC | TAC | CGG | CGC | TGG | CAC | ACC | 483  |
| Ile | Cys | His | Ser | Met | Ala | Tyr | His | Arg | Ile | Tyr | Arg | Arg | Trp | His | Thr |      |
|     |     |     | 145 |     |     |     |     | 150 |     |     |     |     | 155 |     |     |      |
| CCT | CTG | CAC | ATC | TGC | CTC | ATC | TGG | CTC | CTC | ACC | GTG | GTG | GCC | TTG | CTG | 531  |
| Pro | Leu | His | Ile | Cys | Leu | Ile | Trp | Leu | Leu | Thr | Val | Val | Ala | Leu | Leu |      |
|     |     | 160 |     |     |     |     | 165 |     |     |     |     | 170 |     |     |     |      |
| CCC | AAC | TTC | TTT | GTG | GGG | TCC | CTG | GAG | TAC | GAC | CCA | CGC | ATC | TAT | TCC | 579  |
| Pro | Asn | Phe | Phe | Val | Gly | Ser | Leu | Glu | Tyr | Asp | Pro | Arg | Ile | Tyr | Ser |      |
|     | 175 |     |     |     |     | 180 |     |     |     |     | 185 |     |     |     |     |      |
| TGC | ACC | TTC | ATC | CAG | ACC | GCC | AGC | ACC | CAG | TAC | ACG | GCG | GCA | GTG | GTG | 627  |
| Cys | Thr | Phe | Ile | Gln | Thr | Ala | Ser | Thr | Gln | Tyr | Thr | Ala | Ala | Val | Val |      |
| 190 |     |     |     |     | 195 |     |     |     |     | 200 |     |     |     |     | 205 |      |
| GTC | ATC | CAC | TTC | CTC | CTC | CCT | ATC | GCT | GTC | GTG | TCC | TTC | TGC | TAC | CTG | 675  |
| Val | Ile | His | Phe | Leu | Leu | Pro | Ile | Ala | Val | Val | Ser | Phe | Cys | Tyr | Leu |      |
|     |     |     |     | 210 |     |     |     |     | 215 |     |     |     |     | 220 |     |      |
| CGC | ATC | TGG | GTG | CTG | GTG | CTT | CAG | GCC | CGC | AGG | AAA | GCC | AAG | CCA | GAG | 723  |
| Arg | Ile | Trp | Val | Leu | Val | Leu | Gln | Ala | Arg | Arg | Lys | Ala | Lys | Pro | Glu |      |
|     |     |     | 225 |     |     |     |     | 230 |     |     |     |     | 235 |     |     |      |
| AGC | AGG | CTG | TGC | CTG | AAG | CCC | AGC | GAC | TTG | CGG | AGC | TTT | CTA | ACC | ATG | 771  |
| Ser | Arg | Leu | Cys | Leu | Lys | Pro | Ser | Asp | Leu | Arg | Ser | Phe | Leu | Thr | Met |      |
|     |     | 240 |     |     |     |     | 245 |     |     |     |     | 250 |     |     |     |      |
| TTT | GTG | GTG | TTT | GTG | ATC | TTT | GCC | ATC | TGC | TGG | GCT | CCA | CTT | AAC | TGC | 819  |
| Phe | Val | Val | Phe | Val | Ile | Phe | Ala | Ile | Cys | Trp | Ala | Pro | Leu | Asn | Cys |      |
|     | 255 |     |     |     |     | 260 |     |     |     |     | 265 |     |     |     |     |      |
| ATC | GGC | CTC | GCT | GTG | GCC | ATC | AAC | CCC | CAA | GAA | ATG | GCT | CCC | CAG | ATC | 867  |
| Ile | Gly | Leu | Ala | Val | Ala | Ile | Asn | Pro | Gln | Glu | Met | Ala | Pro | Gln | Ile |      |
| 270 |     |     |     |     | 275 |     |     |     |     | 280 |     |     |     |     | 285 |      |
| CCT | GAG | GGG | CTA | TTT | GTC | ACT | AGC | TAC | TTA | CTG | GCT | TAT | TTC | AAC | AGC | 915  |
| Pro | Glu | Gly | Leu | Phe | Val | Thr | Ser | Tyr | Leu | Leu | Ala | Tyr | Phe | Asn | Ser |      |
|     |     |     |     | 290 |     |     |     |     | 295 |     |     |     |     | 300 |     |      |
| TGC | CTG | AAT | GCC | ATT | GTC | TAT | GGG | CTC | TTG | AAC | CAA | AAC | TTC | CGC | AGG | 963  |
| Cys | Leu | Asn | Ala | Ile | Val | Tyr | Gly | Leu | Leu | Asn | Gln | Asn | Phe | Arg | Arg |      |
|     |     |     | 305 |     |     |     |     | 310 |     |     |     |     | 315 |     |     |      |
| GAA | TAC | AAG | AGG | ATC | CTC | TTG | GCC | CTT | TGG | AAC | CCA | CGG | CAC | TGC | ATT | 1011 |
| Glu | Tyr | Lys | Arg | Ile | Leu | Leu | Ala | Leu | Trp | Asn | Pro | Arg | His | Cys | Ile |      |
|     |     | 320 |     |     |     |     | 325 |     |     |     |     | 330 |     |     |     |      |
| CAA | GAT | GCT | TCC | AAG | GGC | AGC | CAC | GCG | GAG | GGG | CTG | CAG | AGC | CCA | GCT | 1059 |
| Gln | Asp | Ala | Ser | Lys | Gly | Ser | His | Ala | Glu | Gly | Leu | Gln | Ser | Pro | Ala |      |
|     | 335 |     |     |     |     | 340 |     |     |     |     | 345 |     |     |     |     |      |
| CCA | CCC | ATC | ATT | GGT | GTG | CAG | CAC | CAG | GCA | GAT | GCT | CTC | TAGCCTG |     |     | 1105 |
| Pro | Pro | Ile | Ile | Gly | Val | Gln | His | Gln | Ala | Asp | Ala | Leu |     |     |     |      |
| 350 |     |     |     |     | 355 |     |     |     |     | 360 |     |     |     |     |     |      |

( 2 ) INFORMATION FOR SEQ ID NO:16:

( i ) SEQUENCE CHARACTERISTICS:
        ( A ) LENGTH: 362 amino acids
        ( B ) TYPE: amino acid -continued ( D ) TOPOLOGY: linear ( i i ) MOLECULE TYPE: protein ( v ) FRAGMENT TYPE: internal ( x i ) SEQUENCE DESCRIPTION: SEQ ID NO:16:

```
Met  Ser  Glu  Asn  Gly  Ser  Phe  Ala  Asn  Cys  Cys  Glu  Ala  Gly  Gly  Trp
 1              5                        10                       15
Ala  Val  Arg  Pro  Gly  Trp  Ser  Gly  Ala  Gly  Ser  Ala  Arg  Pro  Ser  Arg
               20                        25                  30
Thr  Pro  Arg  Pro  Pro  Trp  Val  Ala  Pro  Ala  Leu  Ser  Ala  Val  Leu  Ile
               35                   40                       45
Val  Thr  Thr  Ala  Val  Asp  Val  Val  Gly  Asn  Leu  Leu  Val  Ile  Leu  Ser
 50                            55                       60
Val  Leu  Arg  Asn  Arg  Lys  Leu  Arg  Asn  Ala  Gly  Asn  Leu  Phe  Leu  Val
 65                       70                       75                       80
Ser  Leu  Ala  Leu  Ala  Asp  Leu  Val  Val  Ala  Phe  Tyr  Pro  Tyr  Pro  Leu
                    85                        90                       95
Ile  Leu  Val  Ala  Ile  Phe  Tyr  Asp  Gly  Trp  Ala  Leu  Gly  Glu  Glu  His
                   100                       105                  110
Cys  Lys  Ala  Ser  Ala  Phe  Val  Met  Gly  Leu  Ser  Val  Ile  Gly  Ser  Val
               115                       120                  125
Phe  Asn  Ile  Thr  Ala  Ile  Ala  Ile  Asn  Arg  Tyr  Cys  Tyr  Ile  Cys  His
     130                       135                  140
Ser  Met  Ala  Tyr  His  Arg  Ile  Tyr  Arg  Arg  Trp  His  Thr  Pro  Leu  His
145                       150                       155                      160
Ile  Cys  Leu  Ile  Trp  Leu  Leu  Thr  Val  Ala  Leu  Leu  Pro  Asn  Phe
                    165                       170                  175
Phe  Val  Gly  Ser  Leu  Glu  Tyr  Asp  Pro  Arg  Ile  Tyr  Ser  Cys  Thr  Phe
               180                       185                  190
Ile  Gln  Thr  Ala  Ser  Thr  Gln  Tyr  Thr  Ala  Ala  Val  Val  Val  Ile  His
          195                       200                       205
Phe  Leu  Leu  Pro  Ile  Ala  Val  Val  Ser  Phe  Cys  Tyr  Leu  Arg  Ile  Trp
     210                       215                       220
Val  Leu  Val  Leu  Gln  Ala  Arg  Arg  Lys  Ala  Lys  Pro  Glu  Ser  Arg  Leu
225                       230                       235                      240
Cys  Leu  Lys  Pro  Ser  Asp  Leu  Arg  Ser  Phe  Leu  Thr  Met  Phe  Val  Val
               245                       250                       255
Phe  Val  Ile  Phe  Ala  Ile  Cys  Trp  Ala  Pro  Leu  Asn  Cys  Ile  Gly  Leu
               260                       265                  270
Ala  Val  Ala  Ile  Asn  Pro  Gln  Glu  Met  Ala  Pro  Gln  Ile  Pro  Glu  Gly
               275                       280                  285
Leu  Phe  Val  Thr  Ser  Tyr  Leu  Leu  Ala  Tyr  Phe  Asn  Ser  Cys  Leu  Asn
     290                       295                  300
Ala  Ile  Val  Tyr  Gly  Leu  Leu  Asn  Gln  Asn  Phe  Arg  Arg  Glu  Tyr  Lys
305                       310                       315                      320
Arg  Ile  Leu  Leu  Ala  Leu  Trp  Asn  Pro  Arg  His  Cys  Ile  Gln  Asp  Ala
                    325                       330                  335
Ser  Lys  Gly  Ser  His  Ala  Glu  Gly  Leu  Gln  Ser  Pro  Ala  Pro  Pro  Ile
               340                       345                  350
Ile  Gly  Val  Gln  His  Gln  Ala  Asp  Ala  Leu
               355                       360
```

( 2 ) INFORMATION FOR SEQ ID NO:17:

( i ) SEQUENCE CHARACTERISTICS:
 ( A ) LENGTH: 5 amino acids
 ( B ) TYPE: amino acid
 ( D ) TOPOLOGY: linear ( i i ) MOLECULE TYPE: peptide ( x i ) SEQUENCE DESCRIPTION: SEQ ID NO:17:

Asn Ala Xaa Xaa Tyr
 1               5

( 2 ) INFORMATION FOR SEQ ID NO:18:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:18:

Cys Tyr Ile Cys His Ser
 1               5

( 2 ) INFORMATION FOR SEQ ID NO:19:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:19:

CTGTGCCTCT AAGAGCCACT TGGTTTC          27

( 2 ) INFORMATION FOR SEQ ID NO:20:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:20:

TCCTGGTGAT CCTCTCCGTG CTCA          24

( 2 ) INFORMATION FOR SEQ ID NO:21:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:21:

AGCCAGATGA GGCAGATGTG CAGA          24

( 2 ) INFORMATION FOR SEQ ID NO:22:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:22:

TCCTGGTCAT CCTGTCGGTG TATC 24

( 2 ) INFORMATION FOR SEQ ID NO:23:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:23:

CTGCTGTACA GTTTGTCGTA CTTG 24

( 2 ) INFORMATION FOR SEQ ID NO:24:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:24:

GCAAGAGTGC GCCCTCTACT G 21

( 2 ) INFORMATION FOR SEQ ID NO:25:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:25:

GGCCTCACTT GCCTCCTGCA A 21

( 2 ) INFORMATION FOR SEQ ID NO:26:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:26:

CTAATCCTCG TGGCCAATCT TCTATG 26

( 2 ) INFORMATION FOR SEQ ID NO:27:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:27:

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

CACTGAACTT CTGATTCGCA AACTT    25

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

TATTGAAGAC AGAGCCGATG ACGCTCA    27

What is claimed is:

1. Isolated DNA comprising the coding sequence of SEQ ID NO:1, or a degenerate variant thereof, and encoding the amino acid sequence of (SEQ ID No.2).

2. Isolated DNA comprising the coding sequence of SEQ ID NO:3, or a degenerate variant thereof, and encoding the amino acid sequence of SEQ ID NO:4.

3. Isolated DNA comprising the coding sequence of SEQ ID NO:5, or a degenerate variant thereof, and encoding an amino acid sequence comprising the amino acid sequence of SEQ ID NO.6.

4. Isolated DNA comprising the coding sequence of SEQ ID NO:11, or a degenerate variant thereof, and encoding an amino acid sequence comprising the amino acid sequence of SEQ ID NO:12.

5. Isolated DNA comprising the coding sequence of SEQ ID NO:13, or a degenerate variant thereof, and encoding an amino acid sequence comprising the amino acid sequence of SEQ ID NO:14.

6. Isolated DNA comprising the coding sequence of SEQ ID NO:15, or a degenerate variant thereof, and encoding an amino acid sequence comprising the amino acid sequence of SEQ ID NO:16.

7. Isolated DNA which hybridizes to the DNA sequence of FIG. 1 (SEQ ID NO:1) under conditions of high stringency.

8. Isolated DNA which hybridizes to the DNA sequence of FIG. 2 (SEQ ID NO:3) under conditions of high stringency.

9. Isolated DNA which hybridizes to the DNA sequence of FIG. 4 (SEQ ID NO:5) under conditions of high stringency.

10. Isolated DNA which hybridizes to the DNA sequence of FIG. 5 (SEQ ID NO:11) under conditions of high stringency.

11. Isolated DNA which hybridizes to the DNA sequence of FIG. 3 (SEQ ID NO:13) under conditions of high stringency.

12. Isolated DNA which hybridizes to the DNA sequence of FIG. 6 (SEQ ID NO:15) under conditions of high stringency.

13. A vector comprising the DNA of claim 4.
14. A vector comprising the DNA of claim 10.
15. A vector comprising the DNA of claim 11.
16. A vector comprising the DNA of claim 12.
17. A cell which contains the DNA of claim 10.
18. A cell which contains the DNA of claim 11.
19. A cell which contains the DNA of claim 12.

* * * * *